(12) United States Patent
Yoneda et al.

(10) Patent No.: US 7,217,492 B2
(45) Date of Patent: May 15, 2007

(54) ONIUM SALT COMPOUND AND RADIATION-SENSITIVE RESIN COMPOSITION

(75) Inventors: Eiji Yoneda, Tokyo (JP); Yong Wang, Tokyo (JP); Yukio Nishimura, Tokyo (JP)

(73) Assignee: JSR Corporation, Tokyo (JP)

( * ) Notice: Subject to any disclaimer, the term of this patent is extended or adjusted under 35 U.S.C. 154(b) by 75 days.

(21) Appl. No.: 10/743,809

(22) Filed: Dec. 24, 2003

(65) Prior Publication Data

US 2005/0053861 A1   Mar. 10, 2005

(30) Foreign Application Priority Data

Dec. 25, 2002 (JP) .............................. 2002-373531
Dec. 25, 2002 (JP) .............................. 2002-373625
Jun. 26, 2003 (JP) .............................. 2003-182089
Sep. 8, 2003 (JP) .............................. 2003-315010

(51) Int. Cl.
G03F 7/038 (2006.01)
G03F 7/039 (2006.01)
C07C 303/00 (2006.01)
C07C 307/00 (2006.01)
C07C 315/00 (2006.01)

(52) U.S. Cl. ............... 430/270.1; 430/914; 430/921; 522/31; 564/84; 564/92; 564/95; 564/99; 568/30; 568/34; 568/35

(58) Field of Classification Search ............ 430/914, 430/921, 270.1; 522/31; 564/84, 92, 95, 564/99; 568/30, 34, 35
See application file for complete search history.

(56) References Cited

U.S. PATENT DOCUMENTS 4,374,066 A * 2/1983 Crivello et al. ............. 556/80

FOREIGN PATENT DOCUMENTS

| JP | 59-45439 | 3/1984 |
| JP | 63-36332 | 2/1988 |
| JP | 08027209 | * 1/1996 |
| JP | 2003307839 | * 10/2003 |

OTHER PUBLICATIONS

CA abstract DN 124:292462, JP 8-27209, Jan. 1996.*
CA abstract DN 139-343479, JP 2003-307839, Oct. 2003.*
Crivello, et al., "Complex Triarylsulfonium Salt Photoinitiators. II. The Preparation of Several New Complex Triarylsulfonium Salts and the Influence of Their Structure in Photoinitiated Cationic Polymerization", Journal of Polymer Science, vol. 18, pp. 2697-2714, 1980.
Hattori, et al., "Successive Beckmann Rearrangement-Alkylation Sequence by Organoaluminum Reagents. A Simple Route to dl-Pumiliotoxin C", J. Am. Chem. Soc., vol. 103, pp. 7368-7370, 1981.
Alemagna, et al., "$S_NAr$ Nucleophilic Substitutions of $Cr(CO)_3$-Complexed Aryl Halides with Thiolates under Phase-Transfer Conditions", J. Org. Chem., vol. 48, pp. 605-607, 1983.
Migita, et al., "The Palladium Catalyzed Nucleophilic Substitution of Aryl Halides by Thiolate Anions", Bull. Chem. Soc. Jpn., vol. 53, pp. 1385-1389, 1980.

* cited by examiner

Primary Examiner—Richard L. Schilling
(74) Attorney, Agent, or Firm—Merchant & Gould, P.C.; Christopher W. Raimund

(57) ABSTRACT

An onium salt compound having a cation moiety of the following formula (1) is disclosed.

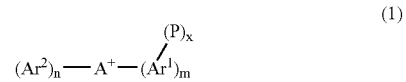

wherein A represents I or S, m is 1 or 2, n is 0 or 1, x is 1–10, and Ar1 and Ar2 are (substituted) aromatic hydrocarbon group, and P represents —O—$SO_2$R, —O—S(O)R, or —$SO_2$R, wherein R represents a hydrogen atom, a (substituted) alkyl group, or a (substituted) alicyclic hydrocarbon group. The onium salt compound is suitable as a photoacid generator for photoresists of a positive-tone radiation-sensitive resin composition. The positive-tone radiation-sensitive resin composition containing this compound is useful as a chemically-amplified photoresist exhibiting high resolution at high sensitivity, responsive to various radiations, and having outstanding storage stability.

15 Claims, 36 Drawing Sheets

ONIUM SALT COMPOUND AND RADIATION-SENSITIVE RESIN COMPOSITION

TECHNOLOGICAL BACKGROUND OF THE INVENTION

1. Field of the Invention

The present invention relates to a novel onium salt compound having an —$SO_2$ structure, —$OSO_2$— structure, or —O—S(O)$R^2$ structure bonded to an aromatic hydrocarbon group or a heterocyclic group, a photoacid generator comprising the onium salt compound, and a positive-tone radiation-sensitive resin composition comprising the photoacid generator useful for microfabrication represented by the manufacture of integrated circuit devices.

2. Description of Background Art

In the field of microfabrication represented by the manufacture of integrated circuit devices, lithographic technology enabling microfabrication with a line width of 0.30 μm or less has been demanded in order to increase the degree of integration in recent years. In a conventional lithographic process, near ultraviolet rays such as i-line radiation have been generally used. However, it is difficult to perform microfabrication with a line width of sub-quarter micron using near ultraviolet rays. Therefore, in order to enable microfabrication with a line width of 0.30 μm or less, utilization of radiation with a shorter wavelength has been studied.

As radiation with a shorter wavelength, deep ultraviolet rays represented by a line spectrum of a mercury lamp and an excimer laser, X-rays, electron beams, and the like can be given. Of these, deep ultraviolet rays such as a KrF excimer laser (wavelength: 248 nm), an ArF excimer laser (wavelength: 193 nm), an $F_2$ excimer laser (wavelength: 157 nm), or EUV (wavelength 13 nm), and electron beams have attracted attention.

As a radiation sensitive resin composition applicable to short wavelength radiations, a number of compositions utilizing a chemical amplification effect between a component having an acid functional group protected with an acid-dissociable group and a photoacid generator which generates an acid upon irradiation (hereinafter referred to as "exposure") has been proposed. Such a composition is hereinafter referred to as a chemically-amplified radiation sensitive composition. For example, Japanese Patent Application Laid-open No. 59-45439 discloses a chemically-amplified radiation-sensitive composition containing a polymer of which the carboxyl group or phenolic hydroxyl group is protected with a t-butoxycarbonyl group and a photoacid generator. This composition utilizes the effect of the polymer to release the t-butoxycarbonyl group by the action of an acid generated by exposure to form an acidic functional group such as a carboxylic group or a phenolic hydroxyl group, which renders an exposed area on a resist film readily soluble in an alkaline developer.

However, most of the photoacid generators currently used for conventional chemically-amplified radiation-sensitive compositions have only insufficient sensitivity. A sulfonium salt compound, which has been regarded as having the highest sensitivity, exhibits only very low base resistance, posing a serious problem of storage stability of the composition. The type of acid diffusion inhibitor, which is a basic additive for improving process stability as a resist, is also limited.

Therefore, development of a highly sensitive, more excellent photoacid generator exhibiting superior base resistance and excellent storage stability is strongly desired.

Japanese Patent Application Laid-open No. 63-36332 and J. of Polymer Sci., Polymer Chemistry Edition, Vol. 18, p. 2697–2714 (1980) disclose that a sulfonium salt compound having a sulfonyl structure bonded with an aromatic ring is useful as a photoinitiator due to a cation mechanism. However, no sulfonium salt compound having a sulfonyl structure bonded with an alicyclic ring has been synthesized heretofore.

The present invention has been completed in view of the above situation and has an object of providing a novel onium salt compound responsive to active radiations such as deep ultraviolet rays represented by a KrF excimer laser, ArF excimer laser, $F_2$ excimer laser, and EUV, as well as to electron beams, having superior storage stability, suitable for a photoacid generator used for a radiation-sensitive resin composition as a high sensitivity, high resolution chemically-amplified photo resist, a photoacid generator comprising the onium salt compound, and a positive-tone radiation-sensitive resin composition comprising the photoacid generator.

SUMMARY OF THE INVENTION

The above object can be achieved in the present invention by an onium salt compound having a cation moiety of the following formula (1),

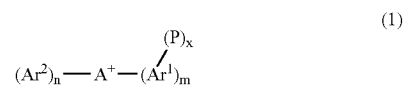

(1)

wherein A represents an iodine atom or a sulfur atom, when A is an iodine atom, m is 1 or 2 and n is 0 or 1, provided that (m+n)=2, and x is an integer of 1–10, and when A is a sulfur atom, m is 1–3 and n is 0–2, provided that (m+n)=3, and x is an integer of 1–15; $Ar^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), $Ar^2$ represents a substituted or unsubstituted monovalent aromatic hydrocarbon group having 6–20 carbon atoms or a substituted or unsubstituted monovalent heterocyclic group having 3–20 atoms, or $Ar^1$ and $Ar^2$ mutually bond together with $A^+$ in the formula to form a group possessing a cyclic structure with 3–8 atoms; and the x-number of P groups bonding to one or more of the m-number of $Ar^1$ groups individually represent —O—$SO_2R^1$, —O—S(O)$R^2$, or —$SO_2R^3$, wherein $R^1$, $R^2$, and $R^3$ individually represent a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group —N(R')$_2$, wherein R' individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or two R' groups form, in combination and together with the nitrogen atom in the formula, a group having a cyclic structure with 3–8 atoms. This compound is hereinafter referred to as onium salt compound (1).

Of the above onium salt compounds, the compounds having a sulfur atom for the group A in formula (1) are preferable.

In addition, among the above onium salt compounds, a compound having the cationic moiety of the following formula (2), that is, the compounds having $-O-SO_2-CF_2-R^4$ for the group P in formula (1), is preferable.

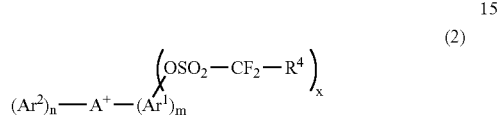

(2)

wherein A, $Ar^1$, m, $Ar^2$, n, and x are the same as A, $Ar^1$, m, $Ar^2$, n, and x in the formula (1) and $R^4$ represents a hydrogen atom, fluorine atom, nitro group, cyano group, or a monovalent organic group having 1–20 carbon atoms. This compound is hereinafter referred to as onium salt compound (2).

Of the above onium salt compounds, the compounds having a sulfur atom for the group A in formula (2) are preferable.

Among the above onium salt compounds (2), a compound of the formula (2), wherein $R^4$ represents the following group (3), is also preferable.

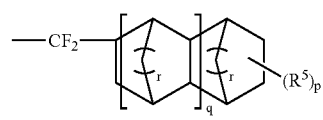

(3)

wherein $R^5$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, a substituted or unsubstituted monovalent heterocyclic group having 3–20 atoms, or a group $-N(R^{2'})_2$, wherein $R^{2'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or two $R^{2'}$ groups form, in combination and together with the nitrogen atom in the formula, a group having a cyclic structure with 3–8 atoms, p is an integer of 0–16, q is an integer of 0–8, and r is an integer of 1–3. This compound is hereinafter referred to as onium salt compound (3).

An onium salt compound of the formula (3), wherein both p and q are 0 and both r's are 1 is particularly preferable.

An onium salt compound having the cationic moiety of the following formula (4), that is, the compound of the formula (1), wherein the group P is represented by the following formula is also preferable.

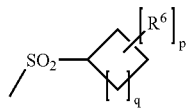

wherein $R^6$, p, and q are respectively the same as $R^6$, p, and q in the formula (4).

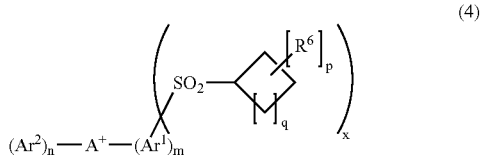

(4)

wherein A, $Ar^1$, m, $Ar^2$, n, and x are respectively the same as A, $Ar^1$, m, $Ar^2$, n, and x in the formula (1), p and q are the same as p and q in the formula (3), and $R^6$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group $-N(R^{3'})_2$, wherein $R^{3'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted, monovalent heterocyclic group having 3–20 atoms, or two $R^{3'}$ groups form, in combination and together with the nitrogen atom in the formula, a group having a cyclic structure with 3–8 atoms. This compound is hereinafter referred to as onium salt compound (4).

An onium salt compound having the cationic moiety of the following formula (5), that is, the compound of the formula (1), wherein the group P is represented by the following formula is also preferable.

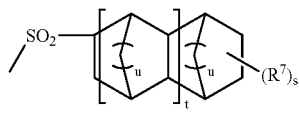

wherein $R^7$, s, t, and u are respectively the same as $R^7$, s, t, and u defined in the formula (5).

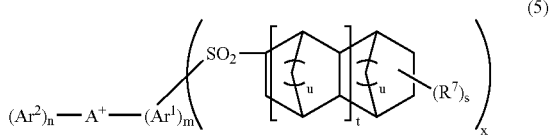

(5)

wherein A, Ar¹, m, Ar², n, and x are respectively the same as A, Ar¹, m, Ar², n, and x defined in the formula (1), $R^7$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group $-N(R^{4'})_2$, wherein $R^{4'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted, monovalent heterocyclic group having 3–20 atoms, or two $R^{4'}$ groups form, in combination and together with the nitrogen atom in the formula, a group having a cyclic structure with 3–8 atoms, s is an integer of 0–6, t is an integer of 0–5, and u is an integer of 1–3. This compound is hereinafter referred to as onium salt compound (5).

An onium salt compound having the cationic moiety of the following formula (6), that is, the compound of the formula (1), wherein the group P is represented by the following formula is also preferable.

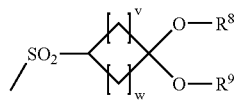

wherein $R^8$, $R^9$, v, and w are respectively the same as $R^8$, $R^9$, v, and w defined in the formula (6).

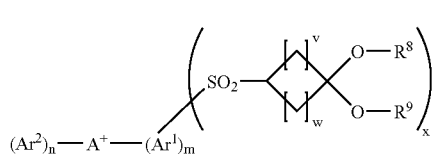

(6)

wherein A, Ar¹, m, Ar², n, and x are respectively the same as A, Ar¹, m, Ar², n, and x defined in the formula (1), $R^8$ and $R^9$ individually represent a substituted or unsubstituted alkyl group having 1–20 carbon atoms or a substituted or unsubstituted monovalent alicyclic group having 3–20 carbon atoms, or $R^8$ and $R^9$ may form, in combination and together with one carbon atom and two oxygen atoms in the formula, a group having a cyclic structure with 4–10 atoms; and v and w are respectively the integers of 0–5, satisfying the formula $(v+w) \geq 1$. This compound is hereinafter referred to as onium salt compound (6)

The above object can further be achieved in the present invention by an onium salt compound of which the cation moiety is represented by the following general formula (7):

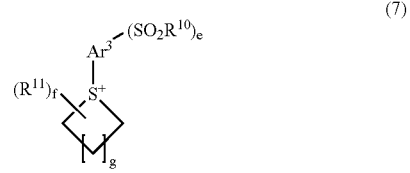

wherein $Ar^3$ represents a substituted or unsubstituted divalent aromatic hydrocarbon group having 6–20 carbon atoms or a substituted or unsubstituted divalent heterocyclic group having 3–20 atoms, $R^{10}$ and $R^{11}$ individually represent a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group $-N(R^{5'})_2$, wherein $R^{5'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted, monovalent heterocyclic group having 3–20 atoms, or two $R^{5'}$ groups form, in combination and together with the nitrogen atom in the formula, a group having a cyclic structure with 3–8 atoms, e is an integer of 1–10, f is an integer of 0–6, and g is an integer of 0–3. This compound is hereinafter referred to as onium salt compound (7).

Among the onium salt compound (7), an onium salt compound having the cationic moiety of the following formula (8), that is, the compound of the formula (7), wherein the group $Ar^3$ is represented by the following formula is also preferable.

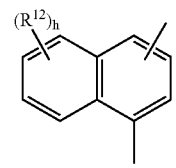

wherein $R^{12}$ and h are respectively the same as $R^{12}$ and h defined in the formula (8).

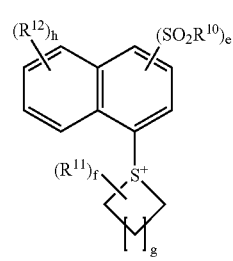

wherein $R^{10}$, e, $R^{11}$, f, and g are respectively the same as $R^{10}$, e, $R^{11}$, f, and g defined for the above formula (7), $R^{12}$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group —N($R^{6'}$)$_2$, wherein $R^{6'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted, monovalent heterocyclic group having 3–20 atoms, or two $R^{6'}$ groups form, in combination and together with the nitrogen atom in the formula, a group having a cyclic structure with 3–8 atoms, and h is an integer of 0–4. This compound is hereinafter referred to as onium salt compound (8).

An onium salt compound having the cationic moiety of the following formula (9), that is, the compound of the formula (7), wherein the group $Ar^3$ is represented by the following formula is also preferable.

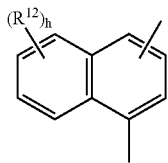

wherein $R^{12}$ and h are respectively the same as $R^{12}$ and h defined in the formula (8).

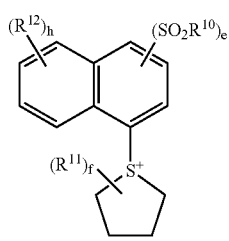

(9)

wherein $R^{10}$, e, $R^{11}$, f, $R^{12}$, and h are the same respectively as $R^{10}$, e, $R^{11}$, f, $R^{12}$, and h defined for the above formula (8). This compound is hereinafter referred to as onium salt compound (9).

An onium salt compound having the cationic moiety of the following formula (10), that is, the compound of the formula (7), wherein the group $Ar^3$ is represented by the following formula and e is 1, is also preferable.

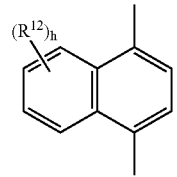

wherein $R^{12}$ and h are respectively the same as $R^{12}$ and h defined in the formula (8).

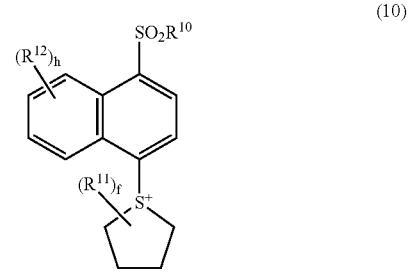

(10)

wherein $R^{10}$, $R^{11}$, f, $R^{12}$, and h are respectively the same as $R^{10}$, $R^{11}$, f, $R^{12}$, and h defined for the above formula (8). This compound is hereinafter referred to as onium salt compound (10).

The above object can be further achieved in the present invention by a positive tone radiation-sensitive resin composition comprising: (A) at least one photoacid generator selected from the onium salt compounds (1) as a photoacid generator for photoresist and (B) a resin having an acid-dissociable group and insoluble or scarcely soluble in alkali, but becomes alkali soluble when the acid-dissociable group dissociates.

Among the positive tone radiation-sensitive resin compositions of the above-described type, the resin composition comprising at least one photoacid generator selected from the onium salt compounds (2) as a photoacid generator for photoresist is preferable.

Among the positive tone radiation-sensitive resin compositions of the above-described type, the resin composition comprising at least one photoacid generator selected from the onium salt compounds (3) as a photoacid generator for photoresist is particularly preferable.

The above object can be further achieved in the present invention by a positive tone radiation-sensitive resin composition comprising: (A) at least one photoacid generator selected from the onium salt compounds (7) as a photoacid generator for photoresist and (B) a resin having an acid-dissociable group and insoluble or scarcely soluble in alkali, but becomes alkali soluble when the acid-dissociable group dissociates.

DETAILED DESCRIPTION OF THE INVENTION

Figure 1:
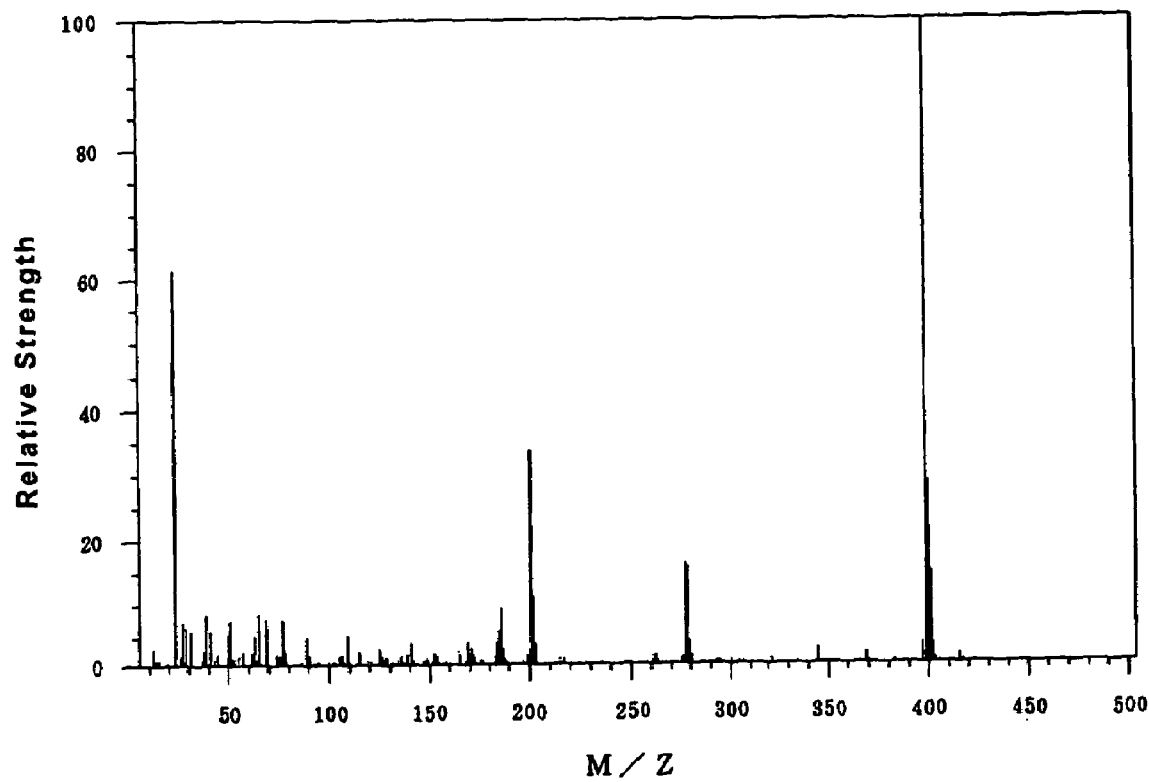
FIG. 1 shows a mass spectrometry spectrum in the cation moiety of the acid generator (A-1).

The present invention will be described in more detail below.

Onium Salt Compounds (1)–(6)

In the formula (1), A is preferably a sulfur atom and x is preferably 1–3. In the unsubstituted aromatic hydrocarbon group having 6–20 carbon atoms with a valence of 1 to (x+1) represented by $Ar^1$ and the unsubstituted monovalent aromatic hydrocarbon group having 6–20 carbon atoms represented by $Ar^2$, the carbon atom content is preferably 6–12, more preferably 6–10, and particularly preferably 6–8.

As specific examples of the unsubstituted monovalent aromatic hydrocarbon group having 6–20 carbon atoms represented by $Ar^1$ or $Ar^2$, a phenyl group, o-tolyl group, m-tolyl group, p-tolyl group, benzyl group, o-methylbenzyl group, m-methylbenzyl group, p-methylbenzyl group, 2,3-xylyl group, 2,4-xylyl group, 2,5-xylyl group, 2,6-xylyl group, 3,4-xylyl group, 3,5-xylyl group, mesityl group, 1-naphthyl group, 2-naphthyl group, 1-anthryl group, and 9-anthryl group can be given.

As examples of the unsubstituted aromatic hydrocarbon group having 6–20 carbon atoms with a valence of 2 to (x+1) represented by $Ar^1$, groups originating from benzene, toluene, o-xylene, m-xylene, p-xylene, 1,3,5-trimethylbenzene, naphthalene, or anthracene can be given. The two to (x+1)-number bonds in these groups may be present either in the carbon atom forming the aromatic ring or in the carbon atom of the side chain.

The unsubstituted heterocyclic group having 3–20 atoms with a valence of 1 to (x+1) represented by $Ar^1$ and the unsubstituted monovalent heterocyclic group having 3–20 atoms represented by $Ar^2$ contain one or more hetero atoms such as a nitrogen atom, oxygen atom, and sulfur atom. The heterocyclic groups contain preferably 4–12 atoms, more preferably 5–10 atoms, and particularly preferably 6–8 atoms.

As specific examples of the monovalent heterocyclic group having 3–20 atoms represented by $Ar^1$ or $Ar^2$, 2-pyridyl group, 3-pyridyl group, 4-pyridyl group, 2-imidazolyl group, 4-imidazolyl group, 5-imidazolyl group, 2-morpholinyl group, 3-morpholinyl group, 2-piperidinyl group, 3-piperidinyl group, 4-piperidinyl group, 2-pyrrolidinyl group, and 3-pyrrolidinyl group can be given.

As examples of the unsubstituted heterocyclic group having 3–20 atoms with a valence of 2 to (x+1) represented by $Ar^1$, groups originating from pyridine, 4-methylpyridine, imidazoline, morpholine, piperidine, pyrrolidine, or the like can be given. The two to (x+1)-number bonds in these heterocyclic groups may be present either in the carbon atom forming the heterocyclic ring or in the carbon atom of the side chain.

As examples of the substituted aromatic hydrocarbon group having 6–20 carbon atoms with a valence of 1 to (x+1) and substituted heterocyclic group having 3–20 atoms with a valence of 1 to (x+1) represented by $Ar^1$, and the substituted monovalent aromatic hydrocarbon group having 6–20 carbon atoms and the substituted monovalent heterocyclic group having 3–20 atoms represented by $Ar^2$, a hydroxyl group, a carboxyl group, an oxo group (=O), an alkyl group having 1–4 carbon atoms (such as a methyl group, ethyl group, n-propyl group, i-propyl group, n-butyl, and t-butyl group), a hydroxyalkyl group having 1–4 carbon atoms (such as a hydroxymethyl group, 1-hydroxyethyl group, 2-hydroxyethyl group, 1-hydroxypropyl group, 2-hydroxypropyl group, 3-hydroxypropyl group, 1-hydroxybutyl group, 2-hydroxybutyl group, 3-hydroxybutyl group, and 4-hydroxybutyl group), an alkoxyl group having 1–4 carbon atoms (such as a methoxy group, ethoxy group, n-propoxy group, i-propoxy group, n-butoxy group, 2-methylpropoxy group, 1-methylpropoxy group, and t-butoxy group), a cyano group, a cyanoalkyl group having 2–5 carbon atoms (such as a cyanomethyl group, 2-cyanoethyl group, 3-cyanopropyl group, and 4-cyanobutyl group), an alkylcarbonyloxy group having 2–5 carbon atoms (such as a methylcarbonyloxy group, ethylcarbonyloxy group, and t-butylcarbonyloxy group), an alkoxycarbonyl group having 2–5 carbon atoms (such as a methoxycarbonyl group, ethoxycarbonyl group, and t-butoxycarbonyl group), an alkoxycarbonylalkoxy group having 3–10 carbon atoms (such as a methoxycarbonylmethoxy group, ethoxycarbonylmethoxy group, and t-butoxycarbonylmethoxy group), a halogen atom (such as a fluorine atom and chlorine atom), and a fluoroalkyl group having 1–4 carbon atoms (such as a fluoromethyl group, trifluoromethyl group, and pentafluoroethyl group) can be given. Any number of one or more types of these substituents may be present in $Ar^1$ or $Ar^2$.

In the definition of the formula (1), "$Ar^1$ and $Ar^2$ may form, in combination and together with $A^+$ in the formula (1), a group having a cyclic structure with 3–8 atoms" refers to a cyclic structure with 3–8 atoms formed from $Ar^1$ and $Ar^2$, wherein two residual groups formed by removing one atom or one group respectively from $Ar^1$ and $Ar^2$ bond directly or via another divalent atom (such as an oxygen atom or a sulfur atom) or another divalent group (for example, an alkylene group such as a methylene group, 1,1-ethylene group, and 1,2-ethylene group or a —NH— group, a —CO— group, or a —$SO_2$— group) in combination and together with $A^+$ in the formula.

The number of atoms including $A^+$ in this cyclic structure is preferably 5–6.

Two or more groups $Ar^1$ and groups $Ar^2$ present in the formulas (1), (2), (4), (5), and (6) may be either the same or different from one another.

As examples of the anion moiety in the onium salt compounds (1)–(6), sulfonic acid anions, $MX_a$ (wherein M indicates a boron atom, a phosphorus atom, an arsenic atom, or an antimony atom, X represents a halogen atom, and a is an integer of 4–6), halogen anions, perchloric acid anions, nitric acid anions, phosphoric acid anions, fluoro phosphoric acid anions, and trifluoroacetic acid anions can be given.

Of these anions, the sulfonic acid anions are particularly preferable. Specific examples of the sulfonic acid anions include $CH_3SO_3^-$, $n\text{-}C_4H_9SO_3^-$ (n-butanesulfonic acid anion), $n\text{-}C_8H_{17}SO_3^-$ (n-octanesulfonic acid anion), $p\text{-}CH_3C_6H_4SO_3^-$ (p-toluenesulfonic acid anion), $CF_3SO_3^-$, $n\text{-}C_4F_9SO_3^-$ (nonafluoro-n-butanesulfonic acid anion), $n\text{-}C_8F_{17}SO_3^-$ (perfluoro-n-octanesulfonic acid anion), and a sulfonic acid anion of the following formula (i) (hereinafter referred to as "sulfonic-acid anion (i)").

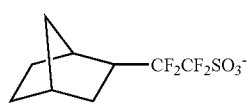

(i)

Of these, $CF_3SO_3^-$, $n\text{-}C_4F_9SO_3^-$, sulfonic acid anion (i), and the like are particularly preferable.

Onium Salt Compound (1)

In the formula (1), P represents —O—$SO_2R^1$, —O—S(O)$R^2$, or —$SO_2R^3$.

In the unsubstituted alkyl group having 1–20 carbon atoms represented by $R^1$, $R^2$, $R^3$, or $R'$ in the groups —O—$SO_2R^1$, —O—S(O)$R^2$, and —$SO_2R^3$, the carbon atom number is preferably 1–18, more preferably 1–15, and particularly preferably 1–12.

As specific examples of the alkyl group, a methyl group, ethyl group, n-propyl group, i-propyl group, n-butyl group, 2-methylpropyl group, 1-methylpropyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-eicosyl group can be given.

In the unsubstituted monovalent alicyclic hydrocarbon group having 3–20 carbon atoms represented by $R^1$, $R^2$, $R^3$, or $R'$, the carbon atom number is preferably 3–18, more preferably 3–12, and particularly preferably 3–8.

As specific examples of the monovalent alicyclic hydrocarbon group, cycloalkyl groups such as a cyclopropyl group, cyclobutyl, cyclopentyl group, and cyclohexyl group and bridged alicyclic hydrocarbon groups having 6–20 carbon atoms such as a norbornyl group, tricyclodecanyl group, tetracyclododecyl group, adamantyl group, 3-methyl-1-adamantyl group, 3-methyl-3-adamantyl group, 3-ethyl-1-adamantyl group, 3-ethyl-3-adamantyl group, 3-n-butyl-1-adamantyl group, and 3-n-butyl-3-adamantyl group can be given.

In the alkenyl group having 2–20 carbon atoms represented by $R^1$, $R^2$, $R^3$, or $R'$, the carbon atom number is preferably 2–18, more preferably 2–15, and particularly preferably 2–12.

As specific examples of the alkenyl group, a vinyl group, isopropenyl group, 1-propenyl group, and 2-propenyl group can be given.

In the unsubstituted monovalent aromatic hydrocarbon group having 6–20 carbon atoms represented by $R^1$, $R^2$, $R^3$, or $R'$, the carbon atom number is preferably 6–12, more preferably 6–10, and particularly preferably 6–8.

As specific examples of the monovalent aromatic hydrocarbon group, a phenyl group, o-tolyl group, m-tolyl group, p-tolyl group, benzyl group, o-methylbenzyl group, m-methylbenzyl group, p-methylbenzyl group, 2,3-xylyl group, 2,4-xylyl group, 2,5-xylyl group, 2,6-xylyl group, 3,4-xylyl group, 5,5-xylyl group, mesityl group, 1-naphthyl group, 2-naphthyl group, 1-anthryl group, and 9-anthryl group can be given.

The unsubstituted monovalent heterocyclic group having 3–20 atoms represented by $R^1$, $R^2$, $R^3$, or $R'$ contain one or more hetero atoms such as a nitrogen atom, oxygen atom, and sulfur atom. The monovalent heterocyclic group contains preferably 3–15 atoms, more preferably 3–12 atoms, and particularly preferably 3–7 atoms.

As specific examples of the monovalent heterocyclic group, 2-pyridyl group, 3-pyridyl group, 4-pyridyl group, 2-imidazolyl group, 4-imidazolyl group, 5-imidazolyl group, 2-morpholinyl group, 3-morpholinyl group, 2-piperidinyl group, 3-piperidinyl group, 4-piperidinyl group, 2-pyrrolidinyl group, and 3-pyrrolidinyl group can be given.

As substituents for the substituted alkyl group having 1–20 carbon atoms, substituted monovalent alicyclic hydrocarbon group having 3–20 carbon atoms, substituted monovalent aromatic hydrocarbon group having 6–20 carbon atoms, or substituted monovalent heterocyclic group having 3–20 atoms represented by $R^1$, $R^2$, $R^3$, or $R'$, the same groups given as examples of the substituents for the substituted monovalent aromatic hydrocarbon group having 6–20 carbon atoms and substituted monovalent heterocyclic group having 3–20 atoms represented by $Ar^1$ or $Ar^2$ can be given, provided that the fluorine-substituted alkyl group having 1–20 carbon atoms represented by $R^1$ does not include a —$CF_2$— group directly bonding to the sulfur atom of $SO_2R^1$ group.

Any number of one or more types of these substituents may be present in $R^1$, $R^2$, $R^3$, or $R'$.

In the definition of the formula (1), "two R' groups form, in combination and together with the nitrogen atom in the formula, a group having a cyclic structure with 3–8 atoms" relating to the —$N(R')_2$ group refers to a cyclic structure with 3–8 atoms formed from two R' groups, wherein two residual groups formed by removing one atom or one group from the two R' groups bond directly or via another divalent atom (such as an oxygen atom or a sulfur atom) or another divalent group (for example, an alkylene group such as a methylene group, 1,2-ethylene group, or a —NH— group, a —CO— group, or a —$SO_2$— group) in combination and together with the nitrogen atom in the formula.

The number of atoms including the nitrogen atom in this cyclic structure is preferably 5–6.

As specific examples of preferable $R^1$, $R^2$, $R^3$, or $R'$ groups, a methyl group, ethyl group, n-propyl group, i-propyl group, n-butyl group, t-butyl group, n-pentyl group, n-hexyl group, n-heptyl group, n-octyl group, n-dodecyl group, t-dodecyl group, n-hexadodecyl group, cyclopentyl group, cyclohexyl group, norbornyl group, 5-oxo-2-norbornyl group, methyl group (2-oxo-7,7-dimethyl-1-norbornyl), p-tolyl group, benzyl group, phenyl group, 1-naphthyl group, 2-naphthyl group, and campholoyl group can be given.

The group —$N(R')_2$, particularly a group such as —$N(CH_3)_2$ and —$N(C_2H_5)_2$, is also a preferable $R^1$, $R^2$, or $R^3$ group.

As $R^2$, $R^3$, or $R'$ groups, groups such as a trifluoromethyl group, nonafluoro-n-butyl group, perfluoro-n-octyl group, and methoxycarbonyl difluoromethyl group are also preferable.

When the formula (1) contains two or more —O—$SO_2R^1$ groups, —O—$S(O)R^2$ groups, or —$SO_2R^3$ groups, these two or more groups may be either the same or different. When two or more —$N(R')_2$ groups are present in the formula (1), these —$N(R')_2$ groups may be either the same or different.

The compounds of the following formulas (1-1) to (1-24) can be given as specific preferable examples of the onium salt compound (1).

(1-1)

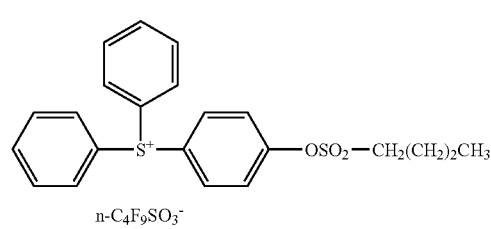

(1-2)

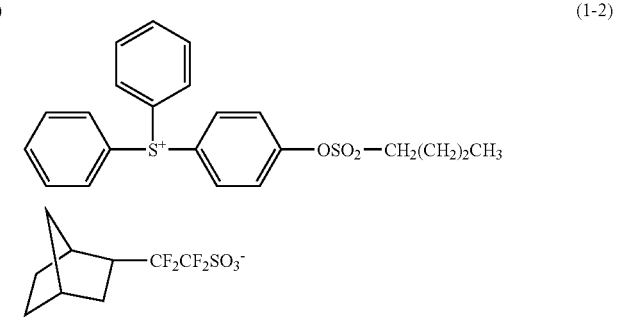

(1-3)

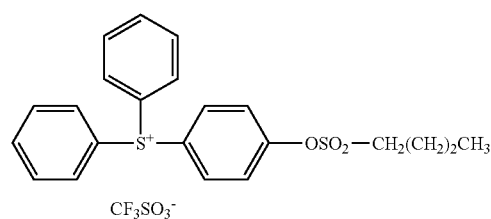

(1-4)

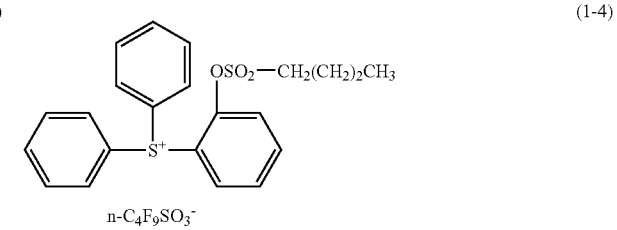

(1-5)

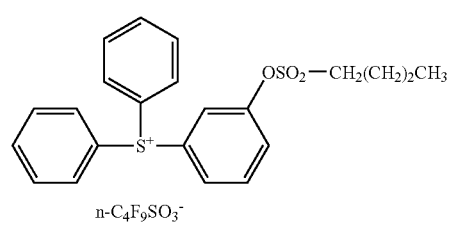

-continued
(1-6)
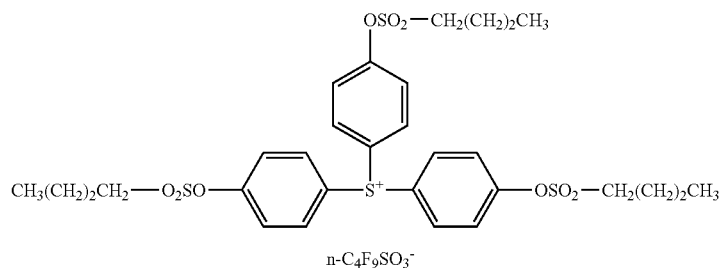
(1-7)
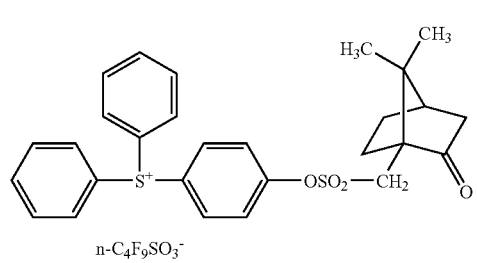
(1-8)
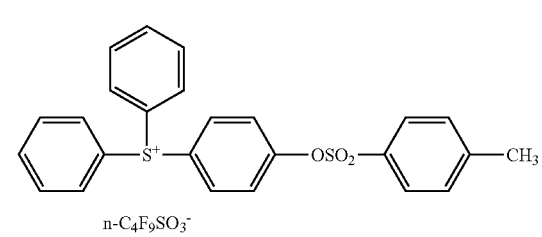
(1-9)
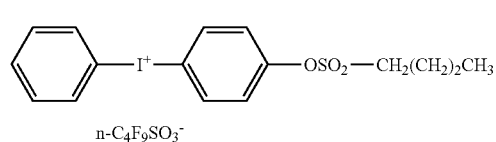
(1-10)
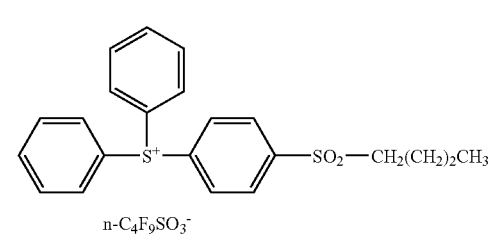
(1-11)
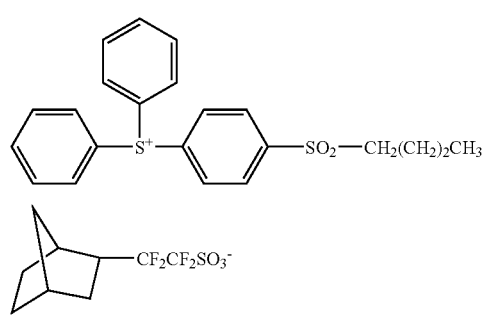
(1-12)
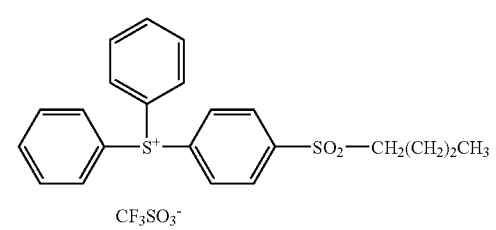
(1-13)
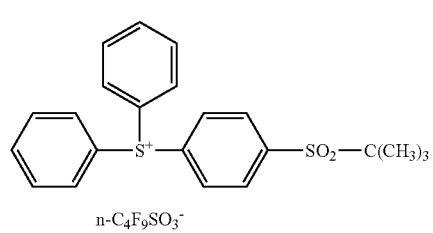
(1-14)
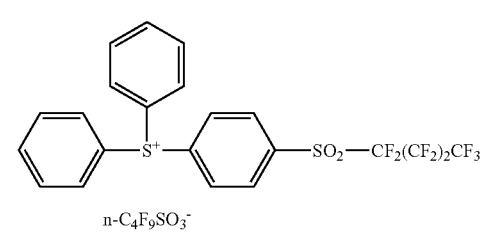
(1-15)
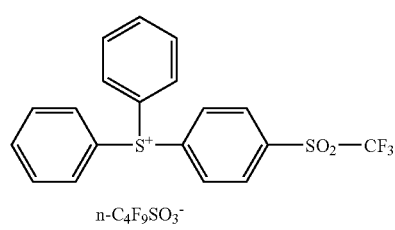
(1-16)
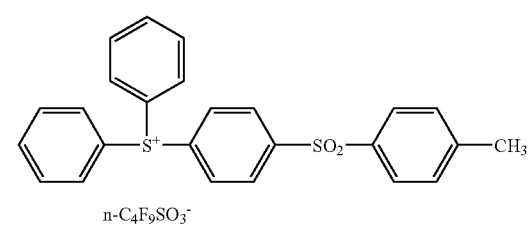

-continued (1-17) 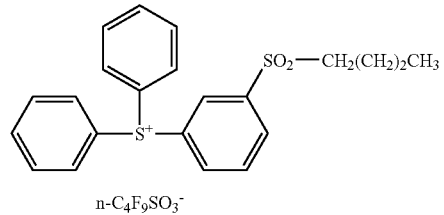

(1-18)

(1-19) 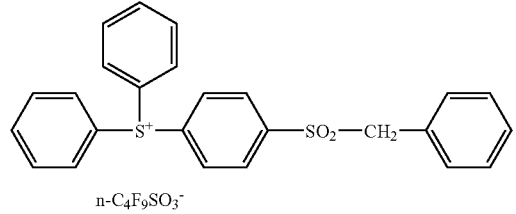

(1-20)

(1-21) 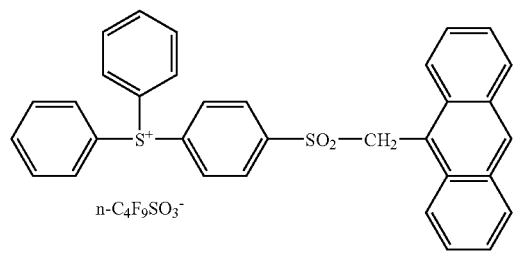

(1-22)

(1-23) 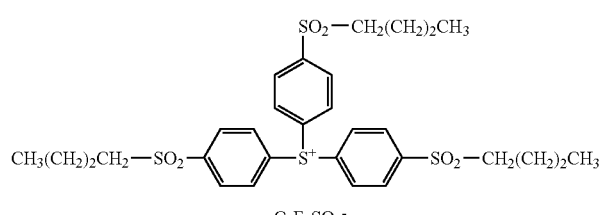

(1-24)

The onium salt compound (1) is not only extremely suitable for use as a photoacid generator responsive to active radiations such as (deep) ultraviolet rays represented by a KrF excimer laser, ArF excimer laser, $F_2$ excimer laser, and EUV, as well as to electron beams, in a radiation-sensitive resin composition useful as a photoresist in the field of microfabrication represented by the manufacture of integrated circuit devices, but also useful as a raw material for the synthesis of a heat acid generator which generates an acid with heating and other related onium salt compounds.

Onium Salt Compound (2)

As examples of the monovalent organic group represented by $R^4$ in the formula (2), a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, a substituted or unsubstituted alkoxycarbonyl group having 2–20 carbon atoms, and a substituted or unsubstituted alkoxycarbonylalkoxy group having 3–20 carbon atoms can be given.

In the various groups represented by $R^4$ in the formula (2), the number of carbon atoms in the unsubstituted alkyl group having 1–20 carbon atoms is preferably 1–18, more preferably 1–15, and particularly preferably 1–12; the number of carbon atoms in the unsubstituted monovalent alicyclic hydrocarbon group having 3–20 carbon atoms is preferably 3–18, more preferably 3–12, and particularly preferably 3–8; the number of carbon atoms in the alkenyl group having 2–20 carbon atoms is preferably 2–18, more preferably 2–15, and particularly preferably 2–12; the number of carbon atoms in the unsubstituted monovalent aromatic hydrocarbon group having 6–20 carbon atoms is preferably 6–12, more preferably 6–10, and particularly preferably 6–8; the unsubstituted monovalent heterocyclic group having 3–20 atoms contains one or more hetero atoms such as a nitrogen atom, oxygen atom, and sulfur atom. The number of atoms in the monovalent heterocyclic group is preferably 3–15, more preferably 3–12, and particularly preferably 3–7; the number of carbon atoms in the unsubstituted alkoxycarbonyl group having 2–20 carbon atoms is preferably 2–18, more preferably 2–15, and particularly preferably 2–12; and the number of carbon atoms in the unsubstituted alkoxycarbonylalkoxy group having 3–20 carbon atoms is preferably 3–18, more preferably 3–15, and particularly preferably 3–12.

As examples of the unsubstituted alkyl group, unsubstituted monovalent alicyclic hydrocarbon group, alkenyl group, unsubstituted monovalent aromatic hydrocarbon group, and unsubstituted monovalent heterocyclic group, the same groups as given for the corresponding groups for $R^1$, $R^2$, $R^3$, and R' can be given.

As examples of the unsubstituted alkoxycarbonyl group having 2–20 carbon atoms represented by $R^4$, a methoxycarbonyl group, ethoxycarbonyl group, and t-butoxycarbonyl group can be given.

As examples of the unsubstituted alkoxycarbonylalkoxy group having 3–20 carbon atoms represented by $R^4$, a methoxycarbonylmethoxy group, ethoxycarbonylmethoxy group, and t-butoxycarbonylmethoxy group can be given.

As examples of the substituent of the alkyl group, monovalent alicyclic hydrocarbon group, monovalent aromatic hydrocarbon group, monovalent heterocyclic group, alkoxycarbonyl group, or alkoxycarbonylalkoxy group, the same substituents given as examples for the substituents of the substituted monovalent aromatic hydrocarbon group having 6–20 carbon atoms and substituted monovalent heterocyclic group having 3–20 atoms represented by $Ar^1$ or $Ar^2$ can be given.

As specific examples of $R^4$, a fluorine atom, nitro group, cyano group, methyl group, ethyl group, n-propyl group, i-propyl group, n-butyl group, 2-methylpropyl group, 1-methylpropyl group, t-butyl group, n-pentyl group, neopentyl group, n-hexyl group, n-heptyl group, n-octyl group, cyclopentyl group, cyclohexyl group, fluoromethyl group, difluoromethyl group, trifluoromethyl group, 1,1-difluoroethyl group, pentafluoroethyl group, 1,1-difluoro-n-propyl group, 1,1,2,2-tetrafluoro-n-propyl group, heptafluoro-n-propyl group, 1,1-difluoro-n-butyl group, 1,1,2,2-tetrafluoro-n-butyl group, 1,1,2,2,3,3-hexafluoro-n-butyl group, nonafluoro-n-butyl group, 1,1-difluoro-n-hexyl group, 1,1,2,2-tetrafluoro-n-hexyl group, 1,1,2,2,3,3-hexafluoro-n-hexyl group, 1,1,2,2,3,3,4,4-octafluoro-n-hexyl group, 1,1,2,2,3,3,4,4,5,5-decafluoro-n-hexyl group, perfluoro-n-hexyl group, perfluoro-n-heptyl group, 3-fluorocyclopentyl group, perfluorocyclopentyl group, 4-fluorocyclohexyl group, perfluorocyclohexyl group, and a group of the following formula (3) (hereinafter referred to as "a fluorine-containing substituent (3)") can be given.

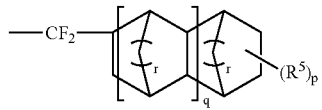

(3)

wherein $R^5$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, a substituted or unsubstituted monovalent heterocyclic group having 3–20 atoms, or a group —N(R$^{2'}$)$_2$, wherein R$^{2'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or two R$^{2'}$ groups form, in combination and together with the nitrogen atom in the formula, a group having a cyclic structure with 3–8 atoms, p is an integer of 0–16, q is an integer of 0–8, and r is an integer of 1–3.

Of these substituents, fluoroalkyl group, a fluorine-containing substituent (3), and the like are particularly preferable.

In the various groups represented by $R^5$ and R$^{2'}$ in the formula (3), the number of carbon atoms in the unsubstituted alkyl group having 1–20 carbon atoms is preferably 1–18, more preferably 1–15, and particularly preferably 1–12; the number of carbon atoms in the monovalent alicyclic hydrocarbon group having 3–20 carbon atoms is preferably 3–18, more preferably 3–12, and particularly preferably 3–8; the number of carbon atoms in the alkenyl group having 2–20 carbon atoms is preferably 2–18, more preferably 2–15, and particularly preferably 2–12; the number of carbon atoms in the monovalent aromatic hydrocarbon group having 6–20 carbon atoms is preferably 6–12, more preferably 6–10, and particularly preferably 6–8; and the unsubstituted monovalent heterocyclic group having 3–20 atoms contains one or more hetero atoms such as a nitrogen atom, oxygen atom, and sulfur atom. The number of atoms in the monovalent heterocyclic group is preferably 3–15, more preferably 3–12, and particularly preferably 3–7.

As examples of the unsubstituted alkyl group, unsubstituted monovalent alicyclic hydrocarbon group, alkenyl group, unsubstituted monovalent aromatic hydrocarbon group, and unsubstituted monovalent heterocyclic group represented by $R^5$ and R$^{2'}$, the same groups as given for the corresponding groups for $R^1$, $R^2$, $R^3$, and R' can be given.

As examples of the substituent of the alkyl group, monovalent alicyclic hydrocarbon group, and monovalent aromatic hydrocarbon group represented by $R^5$ and R$^{2'}$, the same substituents given as examples for the substituents of the substituted monovalent aromatic hydrocarbon group having 6–20 carbon atoms and substituted monovalent heterocyclic group having 3–20 atoms represented by $Ar^1$ or $Ar^2$ can be given. Any number of one or more types of these substituents may be present in $R^5$ or R$^{2'}$.

In the definition of the formula (3), "two R' groups form, in combination and together with the nitrogen atom in the formula, a group having a cyclic structure with 3–8 atoms" relating to the —N(R$^{2'}$)$_2$ group refers to a cyclic structure with 3–8 atoms formed from two R$^{2'}$ groups, wherein two residual groups formed by removing one atom or one group from the two R$^{2'}$ groups bond directly or via another divalent atom (such as an oxygen atom or a sulfur atom) or another divalent group (for example, an alkylene group such as a methylene group, 1,2-ethylene group, or a —NH— group, a —CO— group, or a —SO$_2$— group) in combination and together with the nitrogen atom in the formula.

The number of atoms including the nitrogen atom in this cyclic structure is preferably 5–6.

As specific examples of preferable $R^5$ or R$^{2'}$ groups, a methyl group, ethyl group, n-propyl group, i-propyl group, n-butyl group, t-butyl group, n-pentyl group, n-hexyl group, n-heptyl group, n-octyl group, n-dodecyl group, t-dodecyl group, n-hexadodecyl group, cyclopentyl group, cyclohexyl group, norbornyl group, 5-oxo-2-norbornyl group, methyl group (2-oxo-7,7-dimethyl-1-norbornyl), p-tolyl group, benzyl group, phenyl group, 1-naphthyl group, 2-naphthyl group, trifluoromethyl group, nonafluoro-n-butyl group, perfluoro-n-octyl group, methoxycarbonyl difluoromethyl group, and campholoyl group can be given.

The group —N($R^{2'}$)$_2$, particularly a group such as —N(CH$_3$)$_2$ and —N(C$_2$H$_5$)$_2$, is also a preferable $R^5$ group.

When the formula (3) contains two or more $R^5$ groups, these two or more groups may be either the same or different. When two or more —N($R^{2'}$)$_2$ groups are present, these —N($R^{2'}$)$_2$ groups may be either the same or different.

In the formula (3), p is preferably 0–2, q is preferably 0–2, and more preferably both p and q are 0, and most preferably both p and q are 0, and the two r's are 1.

The compounds of the following formulas (2-1) to (2-9) can be given as specific preferable examples of the onium salt compound (2).

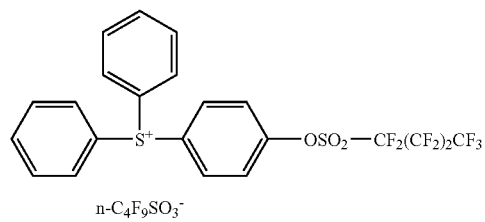

(2-1)

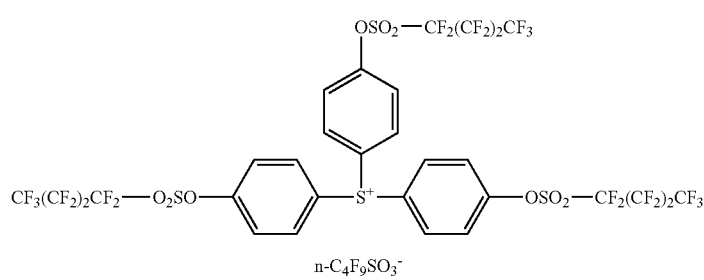

(2-2)

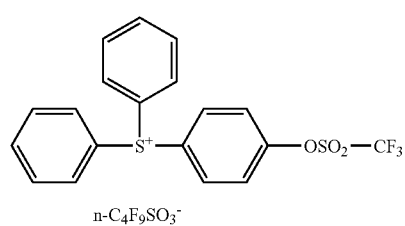

(2-3)

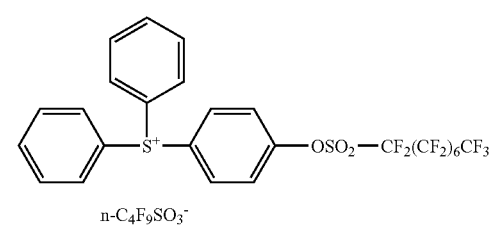

(2-4)

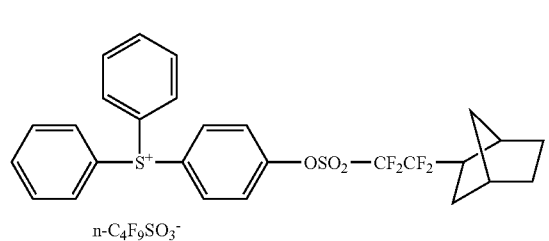

(2-5)

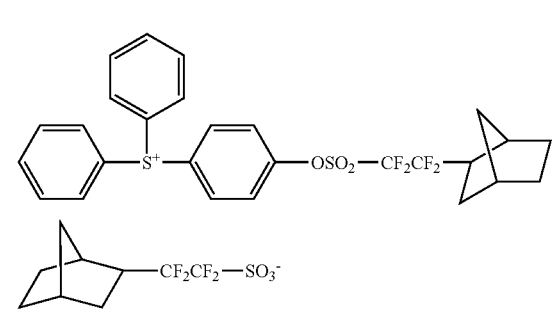

(2-6)

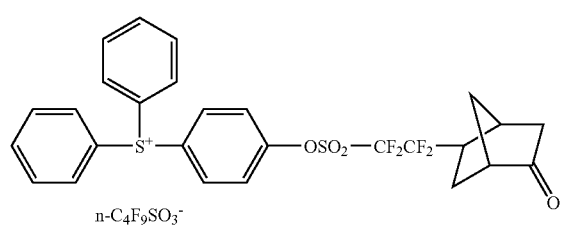

(2-7)

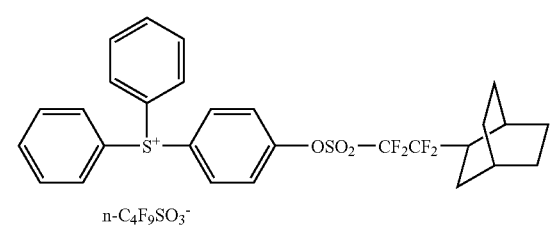

(2-8)

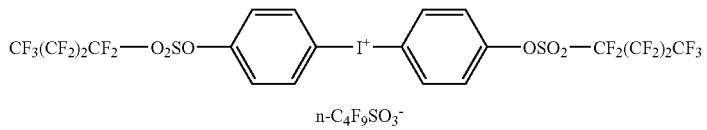

(2-9)

The onium salt compound (2) is not only extremely suitable for use as a photoacid generator responsive to active radiations such as deep ultraviolet rays represented by a KrF excimer laser, ArF excimer laser, $F_2$ excimer laser, and EUV, as well as to electron beams, in a radiation-sensitive resin composition useful as a photoresist in the field of microfabrication represented by the manufacture of integrated circuit devices, but also useful as a raw material for the synthesis of a heat acid generator which generates an acid with heating and other related onium salt compounds.

Onium Salt Compound (4)

As examples of the unsubstituted alkyl group having 1–20 carbon atoms, an unsubstituted monovalent alicyclic hydrocarbon group having 3–20 carbon atoms, alkenyl group having 2–20 carbon atoms, unsubstituted monovalent aromatic hydrocarbon group having 6–20 carbon atoms, and unsubstituted monovalent heterocyclic group having 3–20 atoms represented by $R^6$ and $R^{3'}$ in the formula (4), the same groups as given for the corresponding groups for $R^1$, $R^2$, $R^3$, and $R'$ in the formula (1) can be given.

As examples of the substituents for these groups, the same groups as previously mentioned in connection with the substituted aromatic hydrocarbon groups and substituted heterocyclic groups represented by $Ar^1$ and $Ar^2$ can be given. Any number of one or more types of these substituents may be present in $R^6$ or $R^{3'}$.

In the definition of the $R^6$ group, "two $R^{3'}$ groups form, in combination and together with the nitrogen atom in the formula, a group having a cyclic structure with 3–8 atoms" relating to the —N($R^{3'}$)$_2$ group refers to a cyclic structure with 3–8 atoms formed from two $R^{3'}$ groups, wherein two residual groups formed by removing one atom or one group from the two $R^{3'}$ groups bond directly or via another divalent atom (such as a nitrogen atom, oxygen atom or a sulfur atom) or another divalent group (for example, an alkylene group such as a methylene group, 1,2-ethylene group, or a —NH— group, a —CO— group, or a —SO$_2$-group) in combination and together with the nitrogen atom in the —N($R^{3'}$)$_2$ group.

The number of atoms in this cyclic structure including the nitrogen atom in the —N($R^{3'}$)$_2$ group is preferably 5–6.

As specific preferable examples of the group $R^6$ in the formula (4), the same groups as those previously given as preferable groups for $R^1$, $R^2$, and $R^3$ in the formula (1) can be given. As specific preferable examples of the group $R^{3'}$, the same groups as those previously given as preferable examples of the group $R'$ in the formula (1) can be given.

When two or more $R^6$ groups are present in the compound of formula (4), such groups may be either identical or different.

In the formula (4), p is preferably 0–2 and q is preferably 1–3.

The compounds of the following formulas (4-1) to (4-4) can be given as specific preferable examples of the onium salt compound (4).

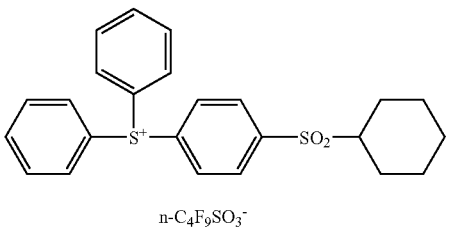

(4-1)

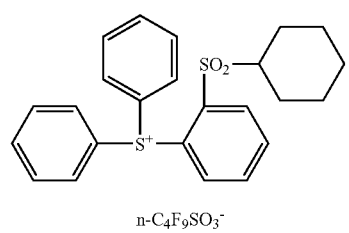

(4-2)

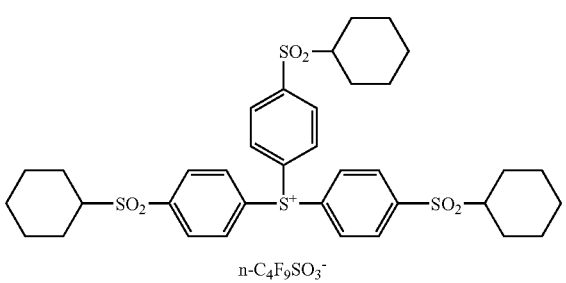

(4-3)

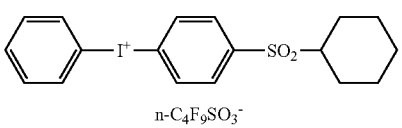

(4-4)

The onium salt compound (4) is not only extremely suitable for use as a photoacid generator responsive to active radiations such as deep ultraviolet rays represented by a KrF excimer laser, ArF excimer laser, $F_2$ excimer laser, and EUV, as well as to electron beams, in a chemically-amplified photoresist used in microfabrication represented by the manufacture of integrated circuit devices, but also useful as a raw material for the synthesis of a heat acid generator which generates an acid with heating and other related onium salt compounds.

Onium Salt Compound (5)

As examples of the unsubstituted alkyl group having 1–20 carbon atoms, unsubstituted monovalent alicyclic hydrocarbon group having 3–20 carbon atoms, alkenyl group having 2–20 carbon atoms, unsubstituted monovalent aromatic hydrocarbon group having 6–20 carbon atoms, and unsubstituted monovalent heterocyclic group having 3–20 atoms represented by $R^7$ and $R^{4'}$ in the formula (5), the same groups as given for the corresponding groups for $R^1$, $R^2$, $R^3$, and R' in the formula (1) can be given.

As examples of the substituents for these groups, the same groups as previously mentioned in connection with the substituted aromatic hydrocarbon groups and substituted heterocyclic groups represented by $Ar^1$ and $Ar^2$ can be given. Any number of one or more types of these substituents may be present in $R^7$ or $R^{4'}$.

In the definition of the $R^7$ group, "two $R^{4'}$ groups form, in combination and together with the nitrogen atom in the formula, a group having a cyclic structure with 3–8 atoms" relating to the —$N(R^{4'})_2$ group refers to a cyclic structure with 3–8 atoms formed from two $R^{4'}$ groups, wherein two residual groups formed by removing one atom or one group from the two $R^{4'}$ groups bond directly or via another divalent atom (such as a nitrogen atom, oxygen atom or a sulfur atom) or another divalent group (for example, an alkylene group such as a methylene group, 1,2-ethylene group, or a —NH— group, a —CO— group, or a —$SO_2$-group) in combination and together with the nitrogen atom in the —$N(R^{4'})_2$ group.

The number of atoms in this cyclic structure including the nitrogen atom of in the —$N(R^{4'})_2$ group is preferably 5–6.

As specific preferable examples of the group $R^7$ in the formula (5), the same groups as those previously given as preferable groups for $R^1$, $R^2$, $R^3$, and R' in the formula (1) can be given. As specific preferable examples of the group $R^{4'}$, the same groups as those previously given as preferable examples of the group R' in the formula (1) can be given.

When two or more $R^7$ groups are present in the compound of formula (5), such groups may be either identical or different.

In the formula (5), s is preferably 0–2, t is preferably 0–2, and u is preferably 1 or 2.

The compounds of the following formulas (5-1) to (5-2) can be given as specific preferable examples of the onium salt compound (5).

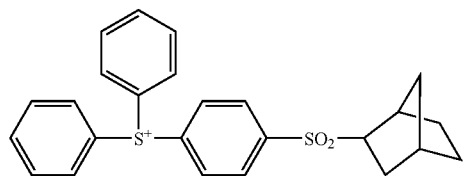

(5-1)

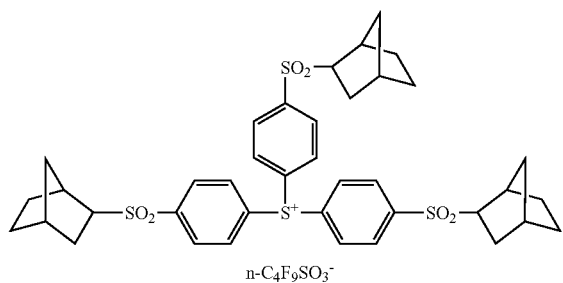

(5-2)

The onium salt compound (5) is not only extremely suitable for use as a photoacid generator responsive to active radiations such as (deep) ultraviolet rays represented by a KrF excimer laser, ArF excimer laser, $F_2$ excimer laser, and EUV, as well as to electron beams, in a chemically-amplified photoresist used in microfabrication represented by the manufacture of integrated circuit devices, but also useful as a raw material for the synthesis of a heat acid generator which generates an acid with heating and other related onium salt compounds.

Onium Salt Compound (6)

As examples of the unsubstituted alkyl group having 1–20 carbon atoms and unsubstituted monovalent alicyclic hydrocarbon group having 3–20 carbon atoms represented by $R^8$ or $R^9$ in the formula (6), the same groups as given for the corresponding groups for $R^1$, $R^2$, $R^3$, and R' in the formula (1) can be given.

As examples of the substituents for these groups, the same groups as previously mentioned in connection with the substituted aromatic hydrocarbon groups and substituted heterocyclic groups represented by $Ar^1$ and $Ar^2$ can be given. Any number of one or more types of these substituents may be present in $R^8$ or $R^9$.

In the definition of the formula (6), "$R^8$ and $R^9$ may form, in combination and together with one carbon atom and two oxygen atoms in the formula, a group having a cyclic structure with 4–10 atoms" refers to a cyclic structure with 4–10 atoms formed from the $R^8$ and $R^9$ groups, wherein two residual groups formed by removing one atom or one group from each of the $R^8$ group and $R^9$ group bond directly or via another divalent atom (such as an oxygen atom or a sulfur atom) or another divalent group (for example, an alkylene group such as a methylene group, 1,2-ethylene group, 1,2-dimethyl-1,2-ethylene group, trimethylene group, or a —NH— group, a —CO— group, or a —$SO_2$-group) in combination and together with one carbon atom and two oxygen atoms in the formula.

The number of atoms in this cyclic structure including the one carbon atom and two oxygen atoms is preferably 5–6.

As specific examples of preferable $R^8$ or $R^9$ groups in the formula (6), a methyl group, ethyl group, n-propyl group, i-propyl group, n-butyl group, t-butyl group, n-pentyl group, n-hexyl group, n-heptyl group, n-octyl group, n-dodecyl group, t-dodecyl group, n-hexadodecyl group, cyclopentyl group, cyclohexyl group, norbornyl group, p-tolyl group, benzyl group, phenyl group, 1-naphthyl group, 2-naphthyl group, trifluoromethyl group, nonafluoro-n-butyl group, perfluoro-n-octyl group, methoxycarbonyl difluoromethyl group, and campholoyl group, as well as groups formed by bonding of the $R^8$ group and $R^9$ group, such as 1,2-ethylene group, 1,2-dimethyl-1,2-ethylene group, trimethylene group, 3,4-tetrahydrofuranylene group, 3,4-tetrahydropyranylene group can be given.

When two or more $R^8$ groups and $R^9$ groups are present in the compound of formula (6), such groups may be either identical or different.

In the formula (6), v and w are preferably 1–3, and more preferably 1–2.

The compounds of the following formulas (6-1) to (6-7) can be given as specific preferable examples of the onium salt compound (6).

(6-1)
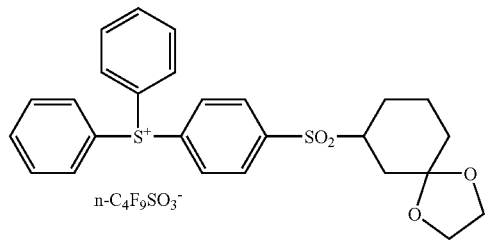

(6-2)
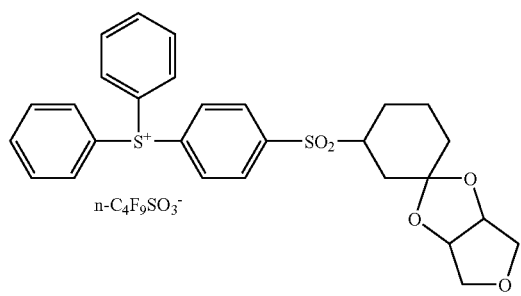

(6-3)
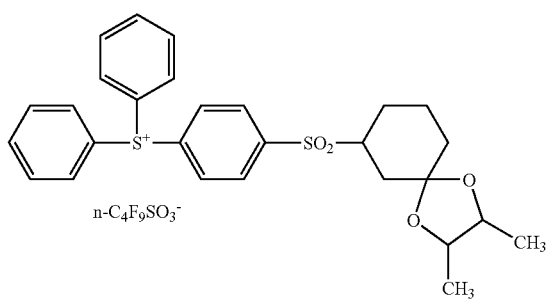

(6-4)
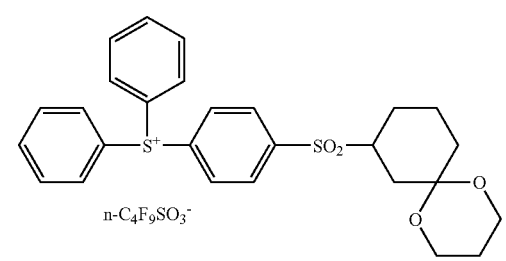

(6-5)
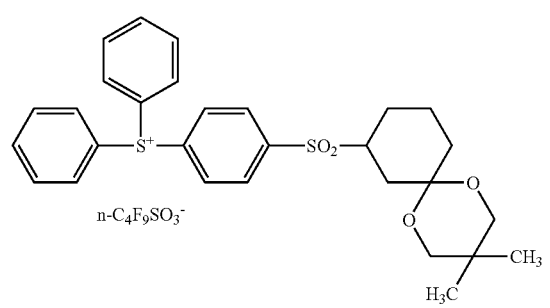

-continued (6-6)
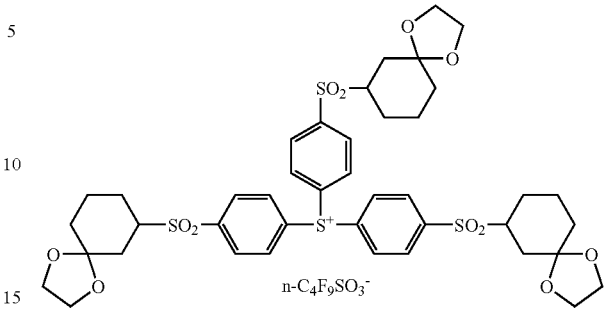

(6-7)
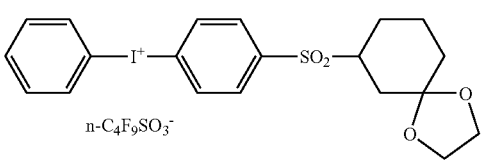

The onium salt compound (6) is not only extremely suitable for use as a photoacid generator responsive to active radiations such as deep ultraviolet rays represented by a KrF excimer laser, ArF excimer laser, $F_2$ excimer laser, and EUV, as well as to electron beams, in a chemically-amplified photoresist used in microfabrication represented by the manufacture of integrated circuit devices, but also useful as a raw material for the synthesis of a heat acid generator which generates an acid with heating and other related onium salt compounds.

Onium Salt Compound (7)

In the formula (7), the number of carbon atoms in the divalent aromatic hydrocarbon group having 6–20 carbon atoms represented by $Ar^3$ is preferably 6–12, more preferably 6–10, and particularly preferably 6–8.

As examples of the divalent aromatic hydrocarbon group, groups originating from benzene, toluene, o-xylene, m-xylene, p-xylene, 1,3,5-trimethylbenzene, naphthalene, or anthracene can be given. The two bonds in these divalent aromatic hydrocarbon groups may be present either in the carbon atom forming the aromatic ring or in the carbon atom of the side chain.

The unsubstituted divalent heterocyclic group having 3–20 atoms represented by $Ar^3$ contains one or more hetero atoms such as a nitrogen atom, oxygen atom, and sulfur atom. The number of the atoms in the divalent heterocyclic group is preferably 4–12, more preferably 5–10, and particularly preferably 6–8.

As examples of the divalent heterocyclic group, groups originating from pyridine, 4-methylpyridine, imidazoline, morpholine, piperidine, pyrrolidine, or the like can be given. The two bonds in these heterocyclic groups may be present either in the carbon atom forming the heterocyclic ring or in the carbon atom of the side chain.

As examples of the substituent for the substituted divalent aromatic hydrocarbon group having 6–20 carbon atoms and the substituted divalent heterocyclic group having 3–20 atoms represented Ar³, the same substituents previously given as examples for the substituents for the substituted aromatic hydrocarbon group and substituted heterocyclic group represented by Ar¹ or Ar² can be given.

Any number of one or more types of these substituents may be present in Ar³.

As examples of the unsubstituted alkyl group having 1–20 carbon atoms, unsubstituted monovalent alicyclic hydrocarbon group having 3–20 carbon atoms, alkenyl group having 2–20 carbon atoms, unsubstituted monovalent aromatic hydrocarbon group having 6–20 carbon atoms, and unsubstituted monovalent heterocyclic group having 3–20 atoms represented by $R^{10}$, $R^{11}$, and $R^{5'}$, the same groups as given for the corresponding groups for $R^1$, $R^2$, $R^3$, and R' in the formula (1) can be given.

As examples of the substituents for these groups, the same groups as previously mentioned in connection with the substituted aromatic hydrocarbon groups and substituted heterocyclic groups represented by Ar¹ and Ar² can be given. Any number of one or more types of these substituents may be present in $R^{10}$, $R^{11}$ or $R^{5'}$.

In the definition of the $R^{10}$ and $R^{11}$ groups, "two $R^{5'}$ groups form, in combination and together with the nitrogen atom in the formula, a group having a cyclic structure with 3–8 atoms" relating to the —N(R⁵')₂ group refers to a cyclic structure with 3–8 atoms formed from two $R^{5'}$ groups, wherein two residual groups formed by removing one atom or one group from the two $R^{5'}$ groups bond directly or via another divalent atom (such as a nitrogen atom, oxygen atom or a sulfur atom) or another divalent group (for example, an alkylene group such as a methylene group, 1,2-ethylene group, or a —NH— group, a —CO— group, or a —SO₂- group) in combination and together with the nitrogen atom in the —N(R⁵')₂ group.

The number of atoms in this cyclic structure including the nitrogen atom in the —N(R⁵')₂ group is preferably 5–6.

As specific preferable examples of the group $R^{10}$ and $R^{11}$ in the formula (7), the same groups as those previously given as preferable groups for R in the formula (1) can be given. As specific preferable examples of the group $R^{5'}$, the same groups as those previously given as preferable examples of the group R' in the formula (1) can be given.

When two or more $R^{10}$ groups and $R^{11}$ groups are present in the compound of formula (7), such groups may be either identical or different.

In the formula (7), e is preferably 1–3, f is preferably 0–2, and g is preferably 1–3.

As examples of the anion moiety in the onium salt compound (7), sulfonic acid anions, $MX_k^-$ (wherein M indicates a boron atom, a phosphorus atom, an arsenic atom, or an antimony atom, X represents a halogen atom, and k is an integer of 4–6), halogen anions, perchloric acid anions, nitric acid anions, phosphoric acid anions, fluoro phosphoric acid anions, and trifluoroacetic acid anions can be given.

Of these anions, the sulfonic acid anions are particularly preferable. Specific examples of the sulfonic acid anions include $CH_3SO_3^-$, $n\text{-}C_4H_9SO_3^-$ (n-butanesulfonic acid anion), $n\text{-}C_8H_{17}SO_3^-$ (n-octanesulfonic acid anion), $p\text{-}CH_3C_6H_4SO_3^-$ (p-toluenesulfonic acid anion), $CF_3SO_3^-$, $n\text{-}C_4F_9SO_3^-$ (nonafluoro-n-butanesulfonic acid anion), $n\text{-}C_8H_{17}SO_3^-$ (perfluoro-n-octanesulfonic acid anion), and a sulfonic acid (i)), with $CF_3SO_3^-$, $n\text{-}C_4F_9SO_3^-$, and the sulfonic acid (i) being particularly preferable.

The compounds of the following formulas (7-1) to (7-10) can be given as specific preferable examples of the onium salt compound (7).

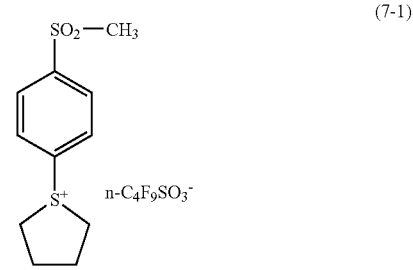

(7-1)

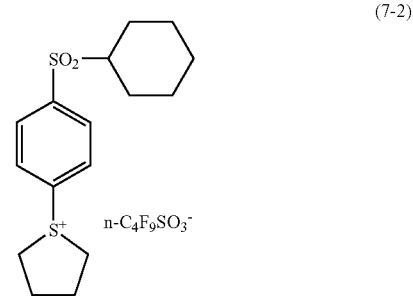

(7-2)

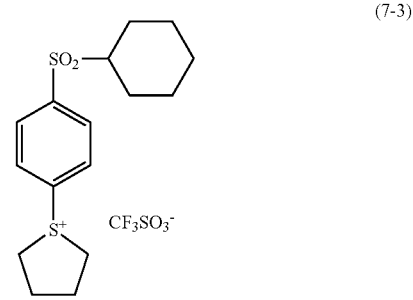

(7-3)

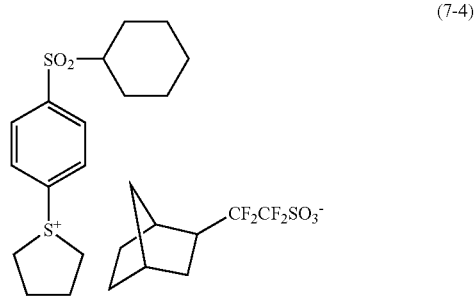

(7-4)

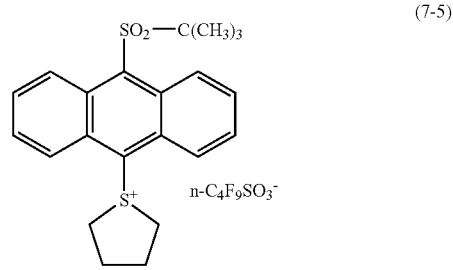

(7-5)

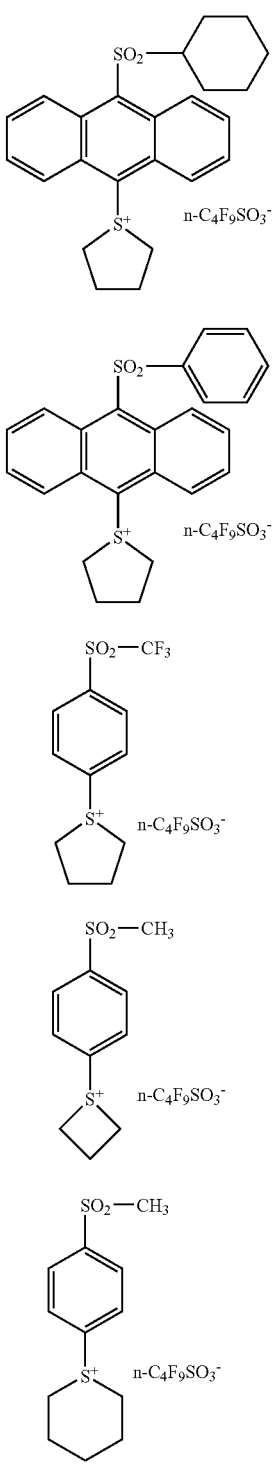

a raw material for the synthesis of a heat acid generator which generates an acid with heating and other related onium salt compounds.

Onium Salt Compound (8)

The onium salt compound (8) is a compound having a substituted or unsubstituted divalent group originating from naphthalene for the $Ar^3$ in the onium salt compound (7) and $S^+$ in the formula bonds to the position 1 of the naphthalene ring.

As examples of the unsubstituted alkyl group having 1–20 carbon atoms, unsubstituted monovalent alicyclic hydrocarbon group having 3–20 carbon atoms, alkenyl group having 2–20 carbon atoms, unsubstituted monovalent aromatic hydrocarbon group having 6–20 carbon atoms, and unsubstituted monovalent heterocyclic group having 3–20 atoms represented by $R^{12}$ and $R^{6\prime}$ in the formula (8), the same groups as given for the corresponding groups for $R^1$, $R^2$, $R^3$, and R' in the formula (1) can be given.

As examples of the substituents for these groups, the same groups as previously mentioned in connection with the substituted aromatic hydrocarbon groups and substituted heterocyclic groups represented by $Ar^1$ and $Ar^2$ can be given. Any number of one or more types of these substituents may be present $R^{12}$ or $R^{6\prime}$.

In the definition of the $R^{12}$ group, "two $R^{6\prime}$ groups form, in combination and together with the nitrogen atom in the formula, a group having a cyclic structure with 3–8 atoms" relating to the $—N(R^{6\prime})_2$ group refers to a cyclic structure with 3–8 atoms formed from two $R^{6\prime}$ groups, wherein two residual groups formed by removing one atom or one group from the two $R^{6\prime}$ groups bond directly or via another divalent atom (such as a nitrogen atom, oxygen atom or a sulfur atom) or another divalent group (for example, an alkylene group such as a methylene group, 1,2-ethylene group, or a —NH— group, a —CO— group, or a —SO$_2$-group) in combination and together with the nitrogen atom in the —N($R^{6\prime}$)$_2$ group.

The number of atoms in this cyclic structure including the nitrogen atom in the —N($R^{6\prime}$)$_2$ group is preferably 5–6.

As specific preferable examples of the groups $R^{10}$, $R^{11}$, and $R^{12}$ in the formula (8), the same groups as those previously given as preferable groups for $R^1$, $R^2$, and $R^3$ in the formula (1) can be given. As specific preferable examples of the group $R^{6\prime}$ the same groups as those previously given as preferable examples of the group R' in the formula (1) can be given. When two or more $R^{10}$ groups, $R^{11}$ groups, and $R^{12}$ groups are present in the compound of formula (8), such groups may be either identical or different.

The compounds of the following formulas (8-1) to (8-2) can be given as specific preferable examples of the onium salt compound (8).

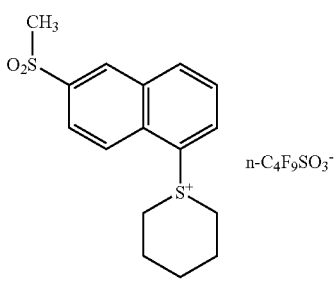

The onium salt compound (7) is not only extremely suitable for use as a photoacid generator responsive to active radiations such as deep ultraviolet rays represented by a KrF excimer laser, ArF excimer laser, F$_2$ excimer laser, and EUV, as well as to electron beams, in a chemically-amplified photoresist used in microfabrication represented by the manufacture of integrated circuit devices, but also useful as -continued (8-2)

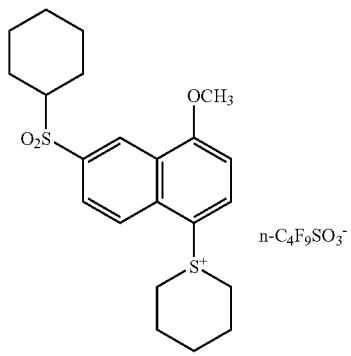

The onium salt compound (8) is not only extremely suitable for use as a photoacid generator responsive to active radiations such as deep ultraviolet rays represented by a KrF excimer laser, ArF excimer laser, $F_2$ excimer laser, and EUV, as well as to electron beams, in a chemically-amplified photoresist used in microfabrication represented by the manufacture of integrated circuit devices, but also useful as a raw material for the synthesis of a heat acid generator which generates an acid with heating and other related onium salt compounds.

Onium Salt Compound (9)

The onium salt compound (9) is a compound having a tetrahydrothiophenium cation in place of the sulfonium cation of the onium salt compound (8).

The compounds of the following formulas (9-1) to (9-2) can be given as specific preferable examples of the onium salt compound (9).

(9-1)

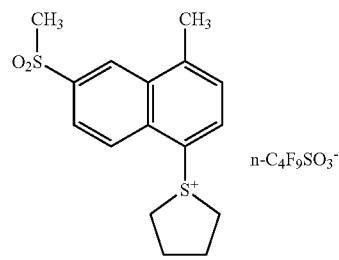

(9-2)

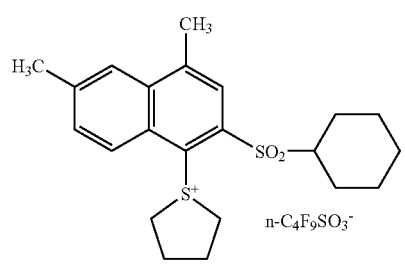

The onium salt compound (9) is not only extremely suitable for use as a photoacid generator responsive to active radiations such as deep ultraviolet rays represented by a KrF excimer laser, ArF excimer laser, $F_2$ excimer laser, and EUV, as well as to electron beams, in a chemically-amplified photoresist used in microfabrication represented by the manufacture of integrated circuit devices, but also useful as a raw material for the synthesis of a heat acid generator which generates an acid with heating and other related onium salt compounds.

Onium Salt Compound (10)

The onium salt compound (10) is a compound having the same structure as the onium salt compound (9), except that in the formula (9) e is 1 and —$SO_2R^{10}$ bonds to the position 4 of the naphthalene ring.

The compounds of the following formulas (10-1) to (10-8) can be given as specific preferable examples of the onium salt compound (10).

(10-1)

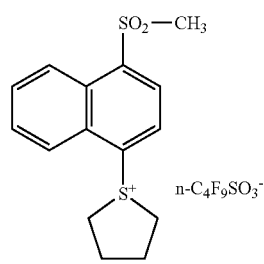

(10-2)

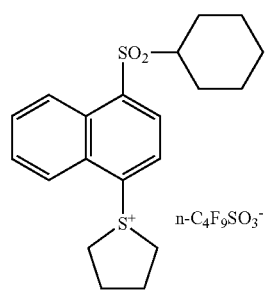

(10-3)

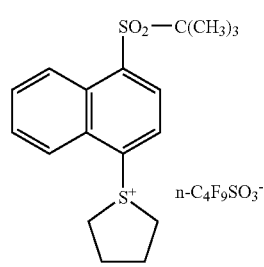

(10-4)

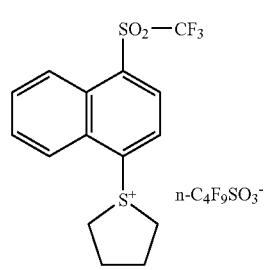

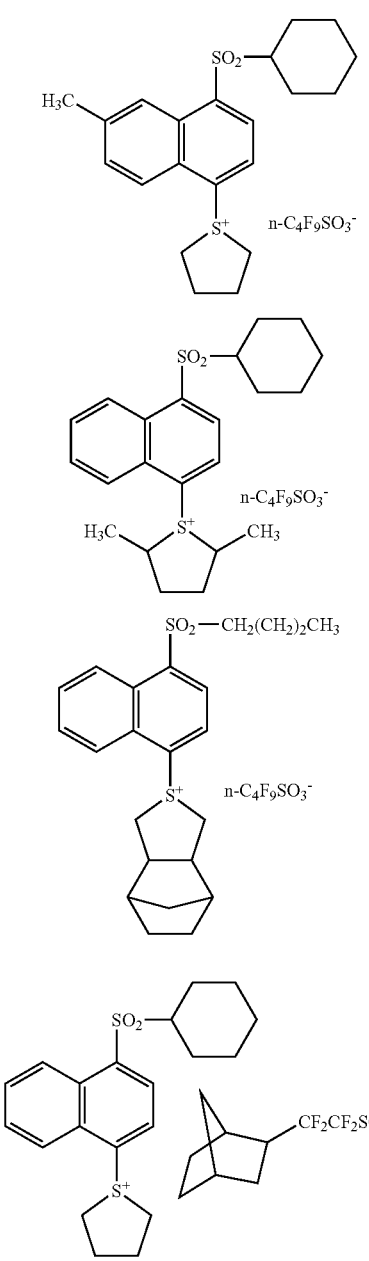

(10-5)

(10-6)

(10-7)

(10-8)

The onium salt compound (10) is not only extremely suitable for use as a photoacid generator responsive to active radiations such as deep ultraviolet rays represented by a KrF excimer laser, ArF excimer laser, $F_2$ excimer laser, and EUV, as well as to electron beams, in a chemically-amplified photoresist used in microfabrication represented by the manufacture of integrated circuit devices, but also useful as a raw material for the synthesis of a heat acid generator which generates an acid with heating and other related onium salt compounds.

Synthesis of Onium Salt Compounds

Synthesis of Onium Salt Compound (1)

When P in the formula (1) is —O—$SO_2R^1$ or —O—S(O)$R^2$, the onium salt compound (1) can be synthesized by the esterification reaction of an onium salt compound precursor (11) and ZCl (a corresponding sulfonic acid chloride or sulfinic acid chloride) in the presence of a basic catalyst as shown in the following reaction formula (a) according to the method described in J. Am. Chem. Soc., Vol. 103, p. 7368–7370 (1981), for example. The onium salt compound (2) can also be synthesized in the same manner as in the synthesis of the onium salt compound (1).

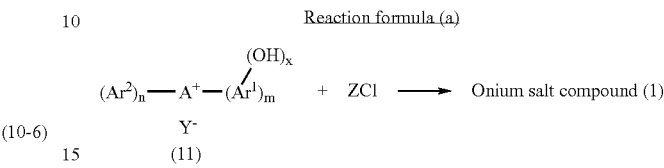

wherein Z is —$SO_2R^1$ or —S(O)$R^2$, A, $Ar^1$, m, $Ar^2$, n, and x are respectively the same as A, $Ar^1$, m, $Ar^2$, n, and x in the formula (1), and $Y^-$ represents a monovalent anion.

The molar ratio of the ZCl to the onium salt compound precursor (11) during the esterification reaction is usually 1–100 and preferably 1.5–10.

As examples of the basic catalyst used in the esterification reaction, triethylamine, pyridine, potassium hydroxide, sodium hydroxide, sodium hydrogencarbonate, potassium hydrogencarbonate, and the like can be given. Of thses, sodium triethylamine and pyridine are preferable.

The molar ratio of the basic catalyst to ZCl in the esterification reaction is usually 1.0–10.0 and preferably 2.0–4.0.

The esterification reaction is usually carried out in an aprotic organic solvent such as toluene, tetrahydrofuran, dichloromethane, pyridine, dimethylformamide, or dimethylsulfoxide.

The reaction is carried out at a temperature of usually −40° C. to +50° C., and preferably −20° C. to +30° C., for usually 0.1–72 hours, and preferably 0.5–3 hours.

When P in the formula (1) is —$SO_2R^3$, the onium salt compound (1) can be synthesized by the reaction formula (b) shown below according to the method described in J. Org. Chem., Vol. 48, p. 605–609 (1983), for example.

Specifically, the onium salt compound precursor (12) is reacted with a thiol compound (13) in the presence of a basic compound (hereinafter referred to as "a thioetherification reaction") to convert the onium salt compound precursor (12) into an onium salt compound (14) having —$SR^3$ group, which is oxidized by an oxidizing agent such as hydrogen peroxide solution to produce the onium salt compound (1).

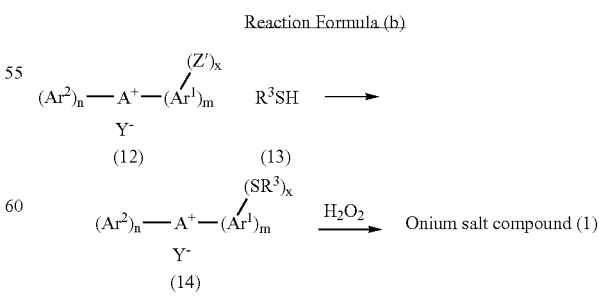

wherein Z' is a dissociable monovalent group bonded to the $Ar^1$ group, A, $Ar^1$, m, $Ar^2$, n, $R^3$, and x are respectively the same as A, Ar¹, m, Ar², n, R¹, and x in the formula (1), and Y⁻ represents a monovalent anion.

As examples of the dissociable monovalent group represented by Z' of the onium salt compound precursor (12), in addition to halogen atoms such as fluorine, chlorine, bromine, and iodine, a $CH_3SO_3^-$ group, a $p\text{-}CH_3C_6H_4SO_3^-$ group (a p-toluenesulfonate residue), and the like can be given, with fluorine and chlorine atoms being preferable.

The molar ratio of the thiol compound (13) to the onium salt compound precursor (12) in the thioetherification reaction is usually 1–100 and preferably 1.5–10.

As examples of the basic compound used in the thioetherification reaction, potassium hydroxide, sodium hydroxide, lithium carbonate, sodium carbonate, potassium carbonate, lithium hydrogencarbonate, sodium hydrogencarbonate, potassium hydrogencarbonate, and the like can be given. Of these, sodium hydroxide and potassium hydroxide are preferable.

The molar ratio of the basic compound to the thiol compound (13) in the thioetherification reaction is usually 1.0–10.0 and preferably 2.0–4.0.

The thioetherification reaction is preferably carried out in a mixed solvent of an organic solvent and water.

As the organic solvent, dichloromethane, chloroform, toluene, benzene, hexane, ethyl acetate, and the like are preferable. Of these, dichloromethane and chloroform are particularly preferable.

The amount of the organic solvent used is usually 5 parts by weight or more, preferably 10 parts by weight or more, and more preferably 20–90 parts by weight for 100 parts by weight of the total amount of the organic solvent and water.

The thioetherification reaction is carried out at a temperature of usually −40° C. to +50° C., and preferably −20° C. to +30° C., for usually 0.1–72 hours, and preferably 0.5–3 hours. If the reaction temperature used is higher than the boiling point of the organic solvent or water, a pressure vessel such as an autoclave is used.

As the oxidizing agent used in the oxidation reaction of the onium salt compound (14), in addition to hydrogen peroxide, methachloroperbenzoic acid, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmiumoxide (VII), rutheniumoxide (VII), sodium hypochlorite, sodium chlorite, oxygen gas, ozone gas, and the like can be given, with hydrogen peroxide, methachloroperbenzoic acid, and t-butyl hydroperoxide being preferable.

The molar ratio of the oxidizing agent to the onium salt compound (14) is usually 1.0–20.0 and preferably 1.5–10.0.

A transition metal catalyst may be used together with the oxidizing agent in the oxidation reaction.

As examples of the transition metal catalyst, disodium tungstate, iron (III) chloride, ruthenium (III) chloride, and selenium (IV) chloride can be given, with disodium tungstate being preferable.

The molar ratio of the transition metal catalyst to the onium salt compound (14) is usually 0.001–2.0, preferably 0.01–1.0, and particularly preferably 0.03–0.5.

Furthermore, in addition to the oxidizing agent and the transition metal catalyst, a buffer agent may be used in the oxidation reaction to control the pH of the reaction solution.

As examples of the buffer agent, disodium hydrogenphosphate, sodium dihydrogenphosphate, dipotassium hydrogenphosphate, potassium dihydrogenphosphate, and the like can be given. The molar ratio of the buffer agent to the onium salt compound (14) is usually 0.01–2.0, preferably 0.03–1.0, and particularly preferably 0.05–0.5.

The oxidation reaction is usually carried out in a solvent.

As the solvent, water, organic solvents such as lower alcohols, tetrahydrofuran, N,N-dimethylformamide, N,N-dimethylacetoamide, acetonitrile, dimethylsulfoxide, acetic acid, trifluoroacetic acid, and the like can be given as preferable examples, with methanol, N,N-dimethylacetoamide, acetonitrile, and dimethylsulfoxide being more preferable, and methanol being particularly preferable.

The amount of the solvent used is usually 5–100 parts by weight, preferably 10–100 parts by weight, and particularly preferably 20–50 parts by weight for 100 parts by weight of the onium salt compound (14).

If necessary, the organic solvent may be used with water. In this case, the amount of the organic solvent used is usually 5 parts by weight or more, preferably 10 parts by weight or more, and particularly preferably 20–90 parts by weight, for 100 parts by weight of the total amount of the organic solvent and water.

The reaction is carried out at a temperature of usually 0–100° C., and preferably 5–60° C., and more preferably 5–40° C., for usually 0.1–72 hours, and preferably 0.5–24 hours.

Synthesis of Onium Salt Compounds (2) and (3)

The above onium salt compounds (2) and (3) can be synthesized according to the reaction formula (a) for the synthesis method of the onium salt compound (1) in which P in formula (1) is $-O-SO_2-R^1$ or $-O-S(O)-R^2$.

Synthesis of Onium Salt Compounds (4)–(6)

The onium salt compounds (4)–(6) can be synthesized according to the reaction formula (b) for the synthesis method of the onium salt compound (1) in which P in formula (1) is $-O-SO_2-R^3$.

Synthesis of Onium Salt Compounds (7)–(10)

The onium salt compound (7) can be synthesized by the reaction formula (c) shown below according to the method described in Bull. Chem. Soc. Jpn., Vol. 53, p. 1385–1389 (1980), for example.

Specifically, the onium salt compound precursor (15) is reacted with the thiol compound (16) in the presence of a transitional metal catalyst and a basic compound (hereinafter referred to as "a sulfidation reaction") to convert the onium salt compound precursor (15) into a sulfide compound (17) having $-R^{10}$ group. The sulfide compound (17) reacted with a sulfoxide compound by electrophilic substitution in the presence of a strong acid to produce a sulfonium salt compound (18). The sulfonium salt compound (18) is oxidized by an oxidizing agent such as hydrogen peroxide solution to produce the onium salt compound (17). The onium salt compounds (8)–(10) can also be synthesized in the same manner as in the synthesis of the onium salt compound (7).

Reaction Formula (c)

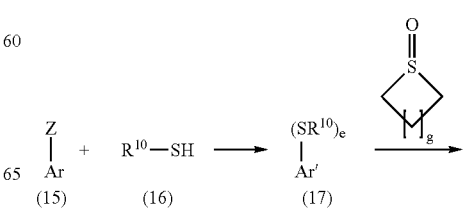

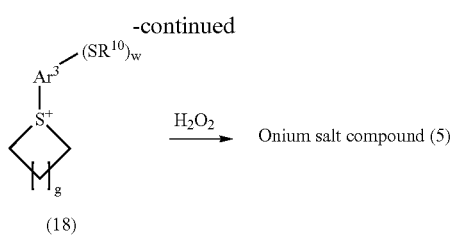

(18) → H$_2$O$_2$ → Onium salt compound (5)

wherein Ar indicates a monovalent group corresponding to the Ar$^3$ group, Ar' indicates a group having a valence of e corresponding to the Ar$^3$ group, Z is a dissociable monovalent group bonded to the Ar group, Ar$^3$, R$^{10}$, e, and g are respectively the same as Ar$^3$, R$^{10}$, e, and g in the formula (7). The group R$^{11}$ in the formula (7) is omitted from the reaction formula (c)

As examples of the dissociable monovalent group represented by Z of the compound precursor (d), in addition to halogen atoms such as fluorine, chlorine, bromine, and iodine, a CH$_3$SO$_3^-$ group, a p-CH$_3$C$_6$H$_4$SO$_3^-$ group (a p-toluenesulfonate residue), and the like can be given, with bromine and fluorine atoms being preferable.

The molar ratio of the thiol compound (16) to the onium salt compound precursor (15) during the sulfidization reaction is usually 1–100 and preferably 1.1–10.

Examples of the transition metal that can be used for the sulfidization reaction include palladium, nickel, platinum, ruthenium, rhodium, and cobalt. Of these, palladium is preferable.

As examples of the basic compound used in the sulfidization reaction, sodium hydroxide, potassium hydroxide, lithium carbonate, sodium carbonate, potassium carbonate, lithium hydrogencarbonate, sodium hydrogencarbonate, potassium hydrogencarbonate, dimethylamine, triethylamine, pyridine, sodium ethoxide, sodium methoxide, and the like can be given. Of these, sodium hydroxide and potassium hydroxide are preferable.

The molar ratio of the basic compound to the thiol compound (16) in the sulfidization reaction is usually 1.0–10.0 and preferably 2.0–4.0.

The sulfidization reaction is preferably carried out in an organic solvent.

As the organic solvent, methanol, ethanol, dichloromethane, chloroform, toluene, benzene, n-hexane, ethyl acetate, and the like are preferable. Of these, methanol and ethanol are particularly preferable. The amount of the organic solvent used is usually 5–100 parts by weight, preferably 10–100 parts by weight, and particularly preferably 20–50 parts by weight for 100 parts by weight of the precursor compound (15).

The sulfidization reaction is carried out at a temperature of usually 50° C. to 120° C., and preferably 60° C. to 100° C., for usually 0.1–72 hours, and preferably 5–20 hours. If the reaction temperature used is higher than the boiling point of the organic solvent, a pressure vessel such as an autoclave is used.

In the above-mentioned electrophilic substitution reaction, a mixture of phosphorus pentaoxide and methansulfonic acid, for example, is preferably used as a strong acidic compound.

The electrophilic substitution reaction is carried out at a temperature of usually −20° C. to 50° C., and preferably 0° C. to 40° C., for usually 0.1–5 hours, and preferably 0.5–2 hours.

As the oxidizing agent used in the oxidation reaction of the onium salt compound (18), in addition to hydrogen peroxide, methachloroperbenzoic acid, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmiumoxide (VII), rutheniumoxide (VII), sodium hypochlorite, sodium chlorite, oxygen gas, ozone gas, and the like can be given, with hydrogen peroxide, methachloroperbenzoic acid, and t-butyl hydroperoxide being preferable.

The molar ratio of the oxidizing agent to the sulfonium-salt compound (18) during the oxidation reaction is usually 1.0–20.0 and preferably 1.5–10.0.

A transition metal catalyst may be used together with the oxidizing agent.

As examples of the transition metal catalyst, disodium tungstate, iron (III) chloride, ruthenium (III) chloride, and selenium (IV) oxide can be given, with disodium tungstate being preferable.

The molar ratio of the transition metal catalyst to the onium salt compound (18) is usually 0.001–2.0, preferably 0.01–1.0, and particularly preferably 0.03–0.5.

Furthermore, in addition to the oxidizing agent and the transition metal catalyst, a buffer agent may be used in the oxidation reaction to control the pH of the reaction solution.

As examples of the buffer agent, disodium hydrogenphosphate, sodium dihydrogenphosphate, dipotassium hydrogenphosphate, potassium dihydrogenphosphate, and the like can be given.

The molar ratio of the buffer agent to the onium salt compound (g) is usually 0.01–2.0, preferably 0.03–1.0, and particularly preferably 0.05–0.5.

The oxidation reaction is usually carried out in a solvent.

As the solvent, water, organic solvents such as lower alcohols, tetrahydrofuran, N,N-dimethylformamide, N,N-dimethylacetoamide, acetonitrile, dimethylsulfoxide, acetic acid, trifluoroacetic acid, and the like can be given as preferable examples, with methanol, N,N-dimethylacetoamide, acetonitrile, and dimethylsulfoxide being more preferable, and methanol being particularly preferable.

The amount of the solvent used is usually 5–100 parts by weight, preferably 10–100 parts by weight, and particularly preferably 20–50 parts by weight for 100 parts by weight of the sulfonium salt compound (18). If necessary, the organic solvent may be used with water. In this case, the amount of the organic solvent used is usually 5 parts by weight or more, preferably 10 parts by weight or more, and particularly preferably 20–90 parts by weight, for 100 parts by weight of the total amount of the organic solvent and water.

The reaction is carried out at a temperature of usually 0–100° C., and preferably 5–60° C., and more preferably 5–40° C., for usually 0.1–72 hours, and preferably 0.5–24 hours.

Photoacid Generator

The photoacid generator of the present invention, represented by the onium salt compounds (1)–(10), generates an acid when exposed to radiation, and is suitably used as a photoacid generator for a radiation-sensitive resin composition useful for microfabrication utilizing various types of radiation represented by deep ultraviolet rays such as a KrF excimer laser, ArF excimer laser, F$_2$ excimer laser, and EUV, and electron beams.

Hereinafter, the photoacid generators obtained from the onium salt compounds (1)–(10) will be referred to as "acid generators (A1)–(A10)".

Positive-Tone Radiation-Sensitive Resin Composition Acid Generator (A)

The component (A) of the positive-tone radiation-sensitive resin composition of the present invention is a photoacid generator (hereinafter referred to as "acid generator (A)") comprising at least one type of photoacid generator as an essential component, selected from the group consisting of acid generators (A1)–(A10).

In the acid generators (A1)–(A6), A, $Ar^1$, m, $Ar^2$, n, and x in the formulas (1) to (6) are individually the same or different.

In the acid generators (A7)–(A10), $R^{10}$, e, $R^{11}$, f, and g in formulas (7) to (10) are individually the same or different, and $R^{12}$ and h in formulas (8) to (10) are individually the same or different.

The acid generators (A1)–(A10) can be used either individually or in combination of two or more in the positive-tone radiation-sensitive resin composition of the present invention.

One or more photoacid generators other than the acid generators (A1)–(A10) (hereinafter referred to as "other acid generators") can be used in combinations in the positive-tone radiation-sensitive resin composition of the present invention.

As examples of the other acid generators, onium salt compounds, sulfone compounds, sulfonate compounds, sulfonimide compounds, diazomethane compounds, disulfonylmethane compounds, and the like can be given.

As examples of onium salts, iodonium salts, sulfonium salts (including tetrahydrothiophenium salts), phosphonium salts, diazonium salts, ammonium salt, pyridinium salts, and the like can be given.

As examples of the sulfone compound, β-ketosulfone, β-sulfonylsulfone, and α-diazo compounds of these compounds can be given.

As examples of the sulfonate compound, alkyl sulfonate, haloalkyl sulfonate, aryl sulfonate, and imino sulfonate can be given.

As an example of the sulfonimide compound, a compound of the following formula (19) can be given:

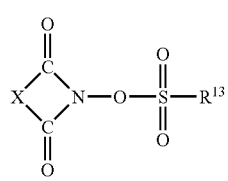

(19)

wherein x is a divalent organic group and $R^{13}$ is a monovalent organic group.

As examples of x in the formula (19), a methylene group, linear or branched alkylene group having 2–20 carbon atoms, aralkylene group having 2–20 carbon atoms, difluoromethylene group, linear or branched perfluoroalkylene group having 2–20 carbon atoms, cyclohexylene group, phenylene group, substituted or unsubstituted divalent group possessing a norbornene skeleton, or a group wherein these groups are substituted with an aryl group having 6 or more carbon atoms or an alkoxyl group having 1 or more carbon atoms can be given.

As examples of $R^{13}$, a linear or branched alkyl group having 1–10 carbon atoms, linear or branched perfluoroalkyl group having 1–10 carbon atoms, perfluorocycloalkyl group having 3–10 carbon atoms, monovalent hydrocarbon group possessing a bicyclo ring having 7–15 carbon atoms, and an aryl group having 6–12 carbon atoms, can be given.

As an example of the diazomethane compound, a compound of the following formula (20) can be given:

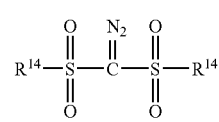

(20)

wherein $R^{14}$ individually represents a monovalent group such as a linear or branched alkyl group, cycloalkyl group, aryl group, halogenated alkyl group, halogenated cycloalkyl group, and halogenated aryl group.

As an example of the disulfonylmethane compound, a compound of the following formula (21) can be given:

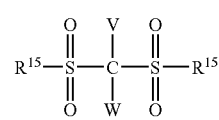

(21)

wherein $R^{15}$ individually represents a linear or branched monovalent aliphatic hydrocarbon group, a cycloalkyl group, aryl group, aralkyl group, or other monovalent organic group having a hetero atom, V and W individually represent an aryl group, hydrogen atom, linear or branched monovalent aliphatic hydrocarbon group, cycloalkyl group, aralkyl group, or other monovalent organic group having a hetero atom, provided that at least one of V and W represents an aryl group, or V and W bond to form a monocyclic or polycyclic ring having at least one unsaturated bond, or V and W bond to form a group shown by the following formula (ii);

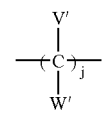

(ii)

wherein V's and W's individually represent a hydrogen atom, halogen atom, a linear or branched alkyl group, cycloalkyl group, aryl group, or aralkyl group, or V' and W', each bonded to the same or different carbon atoms, may form a monocarbocyclic structure, and j is an integer from 2 to 10.

The other acid generator is preferably one or more acid generators selected from the group consisting of an onium salt compound, sulfonimide compound, and diazomethane compound.

As a particularly preferable other acid generator, at least one compound selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium p-toluenesulfonate, bis(4-t-butylphenyl)iodonium 10-camphorsulfonate, bis(4-t-butylphenyl)iodonium 2-trifluoromethylbenzenesulfonate, bis(4-t-butylphenyl)iodonium 4-trifluoromethylbenzenesulfonate, bis(4-t-butylphenyl)iodonium 2,4-difluorobenzenesulfonate, triphenylsulfonium trifluoromethanesulfonate, triphenylsulfonium nonafluoro-n-butanesulfonate, triphenylsulfonium p-toluenesulfonate, triphenylsulfonium 10-camphorsulfonate, triphenylsulfonium 2-trifluoromethylbenzenesulfonate, triphenylsulfonium 4-trifluorobenzenesulfonate, triphenylsulfonium 2,4-difluoromethylbenzenesulfonate, 1-(4-n-butoxynaphthalene-1-yl)tetrahydrothiophenium trifluoromethanesulfonate, 1-(4-n-butoxynaphthalene-1-yl)tetrahydrothiophenium nonafluoro-n-butanesulfonate-N-(trifluoromethane sulfonyloxy)succinimide, N-(trifluoromethanesulfonyloxy)bicyclo[2.2.1]hept-5-ene-2,3-dicarboxyimide, N-(10-camphorsulfonyloxy)succinimide, N-(10-camphorsulfonyloxy)bicyclo[2.2.1]hept-5-ene-2,3-dicarboxyimide, N-{(5-methyl-5-carboxymethanebicyclo[2.2.1]hept-2-yl)-sulfonyloxy}succinimide, bis(cyclohexanesulfonyl)diazomethane, bis(t-butylsulfonyl)diazomethane, and bis(1,4-dioxaspiro[4.5]-decan-7-sulfonyl)diazomethane.

The proportion of other acid generators can be appropriately determined depending on the types of each acid generator. The proportion is 95 parts by weight or less, preferably 90 parts by weight or less, and particularly preferably 90 parts by weight or less for 100 parts by weight of the total amount of the acid generator (A1), the acid generator (A2), and other acid generators. If the proportion of the other acid generators exceeds 95 parts by weight, the desired effects of the present invention may be impaired.

Acid-Dissociable Group-Containing Resin (B)

The component (B) of the positive-tone radiation sensitive resin composition of the present invention is an acid-dissociable group-containing resin which is insoluble or scarcely soluble in alkali, but becomes easily soluble in alkali when the acid-dissociable group dissociates (hereinafter referred to as "acid-dissociable group-containing resin (B)").

If 50% or more of the initial film thickness of a resist film remains after development when a resist film made only from the acid-dissociable group-containing resin (B) is developed under the same alkaline development conditions employed for forming a resist pattern using a resist film formed from a radiation-sensitive resin composition comprising the acid-dissociable group-containing resin (B), such a characteristic of the acid-dissociable group-containing resin (B) is referred to as "insoluble or scarcely soluble in alkali" in the present invention.

The acid-dissociable group of the acid-dissociable group-containing resin (B) refers to a group which is replaced with the hydrogen atom in an acid-functional group such as a phenolic hydroxyl group, carboxyl group, and sulfonic group and is dissociable in the presence of an acid.

As examples of such an acid-dissociable group, a substituted methyl group, 1-substituted ethyl group, 1-substituted-n-propyl group, 1-branched alkyl group, alkoxycarbonyl group, acyl group, cyclic acid-decomposable group, and the like can be given.

As examples of a substituted methyl group, a methoxymethyl group, methylthiomethyl group, ethoxymethyl group, ethylthiomethyl group, methoxyethoxymethyl group, benzyloxymethyl group, benzylthiomethyl group, phenacyl group, 4-bromophenacyl group, 4-methoxyphenacyl group, 4-methylthiophenacyl group, a-methylphenacyl group, cyclopropylmethyl group, benzyl group, diphenylmethyl group, triphenylmethyl group, 4-bromobenzyl group, 4-nitrobenzyl group, 4-methoxybenzyl group, 4-methylthiobenzyl group, 4-ethoxybenzyl group, 4-ethylthiobenzyl group, piperonyl group, methoxycarbonylmethyl group, ethoxycarbonylmethyl group, n-propoxycarbonylmethyl group, i-propoxycarbonylmethyl group, n-butoxycarbonylmethyl group, and t-butoxycarbonylmethyl group can be given.

As examples of the 1-substituted ethyl group, a 1-methoxyethyl group, 1-methylthioethyl group, 1,1-dimethoxyethyl group, 1-ethoxyethyl group, 1-ethylthioethyl group, 1,1-diethoxyethyl group, 1-phenoxyethyl group, 1-phenylthioethyl group, 1,1-diphenoxyethyl group, 1-benzyloxyethyl group, 1-benzylthioethyl group, 1-cyclopropyloxyethyl group, 1-cyclohexyloxyethyl group, 1-phenylethyl group, 1,1-diphenylethyl group, 1-methoxycarbonylethyl group, 1-ethoxycarbonylethyl group, 1-n-propoxycarbonylethyl group, 1-1-propoxycarbonylethyl group, 1-n-butoxycarbonylethyl group, and 1-t-butoxycarbonylethyl group can be given.

As examples of 1-substituted n-propyl group, a 1-methoxy-n-propyl group, and 1-ethoxy-n-propyl group can be given.

As examples of a 1-branched alkyl group, an i-propyl group, 1-methylpropyl group, t-butyl group, 1,1-dimethylpropyl group, 1-methylbutyl group, and 1,1-dimethylbutyl group can be given.

As examples of the alkoxycarbonyl groups, a methoxycarbonyl group, ethoxycarbonyl group, i-propoxycarbonyl group, t-butoxycarbonyl group, and the like can be given.

As examples of the acyl group, an acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, sccucinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluenesulfonyl group, and mesyl group can be given.

As examples of the cyclic acid-decomposable group, a cyclopropyl group, cyclopentyl group, cyclohexyl group, cyclohexenyl group, 4-methoxycyclohexyl group, tetrahydropyranyl group, tetrahydrofuranyl group, tetrahydrothiopyranyl group, tetrahydrothiofuranyl group, 3-bromotetrahydropyranyl group, 4-methoxytetrahydropyranyl group, 4-methoxytetrahydrothiopyranyl group, and 3-tetrahydrothiophene-1,1-dioxide group can be given.

Of these acid-dissociable groups, a benzyl group, t-butoxycarbonylmethyl group, 1-methoxyethyl group, 1-ethoxyethyl group, 1-cyclohexyloxyethyl group, 1-ethoxy-n-propyl group, t-butyl group, 1,1-dimethylpropyl group, t-butoxycarbonyl group, tetrahydropyranyl group, tetrahydrofuranyl group, tetrahydrothiopyranyl group, tetrahydrothiofuranyl group, and the like are preferable.

The acid-dissociable group-containing resin (B) may contain one or more acid-dissociable groups.

The amount of the acid-dissociable group introduced into the acid-dissociable group-containing resin (B) (the amount of the number of acid-dissociable groups in the total number of acidic functional groups and acid-dissociable groups in the acid-dissociable group-containing resin (B)) is preferably 5–100%, and still more preferably 10–100%, although the amount varies depending on the type of resin into which the acid-dissociable group is introduced.

Various types of structure for the acid-dissociable group containing resin (B) may be used without any restrictions as long as the above properties can be obtained. Preferable structures include a poly(p-hydroxystyrene) in which part or all of the hydrogen atoms in the phenolic hydroxyl groups are replaced by acid-dissociable groups, a copolymer of p-hydroxystyrene and/or p-hydroxy-α-methylstyrene and (meth) acrylic acid in which part or all of the hydrogen atoms in the phenolic hydroxyl groups and/or carboxyl groups are replaced by acid-dissociable groups, and the like.

Also, the structure of the acid-dissociable group-containing resin (B) can be appropriately determined according to the type of radiation employed.

As a preferable example of an acid-dissociable group-containing resin (B) especially suitable for a radiation-sensitive resin composition using a KrF excimer laser, an alkali insoluble or scarcely soluble resin having at least one recurring unit of the following formula (22) (hereinafter referred to as "recurring unit (22)") and at least one recurring unit (22), wherein the phenolic hydroxyl group is protected by an acid-dissociable group can be given (such an acid-dissociable group-containing resin is hereinafter referred to as "resin (B1)"). The resin (B1) may be suitably used in radiation-sensitive resin compositions for use with other radiations such as ArF excimer laser, $F_2$ excimer laser, and electron beams.

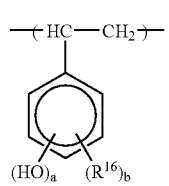

(22)

wherein $R^{16}$'s individually represent a hydrogen atom or monovalent organic group, and a and b each represent an integer from 1–3.

As the recurring unit (22), units wherein the non-aromatic double bond of p-hydroxystyrene is cleaved are preferable.

The resin (B1) may contain at least one other recurring unit.

As examples of the other recurring unit, units obtained by cleavage of a polymerizable unsaturated bond of vinyl aromatic compounds such as styrene; (meth) acrylic esters such as t-butyl (meth)acrylate, adamantyl (meth)acrylate, and 2-methyladamantyl (meth)acrylate; and the like can be given.

As a preferable example of an acid-dissociable group-containing resin (B) especially suitable for a radiation-sensitive resin composition using an ArF excimer laser, an alkali soluble or scarcely soluble resin having at least one recurring unit selected from the group consisting of the recurring unit of the following formula (23) (hereinafter referred to as "recurring unit (23)") and the recurring unit of the following formula (24) (hereinafter referred to as "recurring unit (24)"), and at least one recurring unit of the following formula (25) (hereinafter referred to as "recurring unit (25)") can be given. This resin is hereinafter referred to as "resin (B2)". The resin (B2) may be suitably used in radiation-sensitive resin compositions for use with other radiations such as KrF excimer laser, $F_2$ excimer laser, and electron beams.

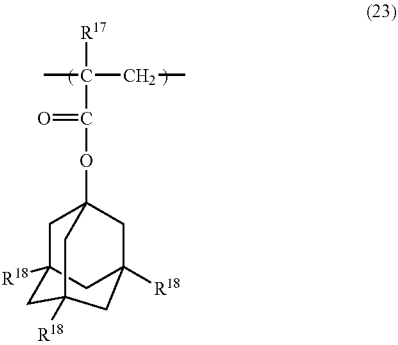

(23)

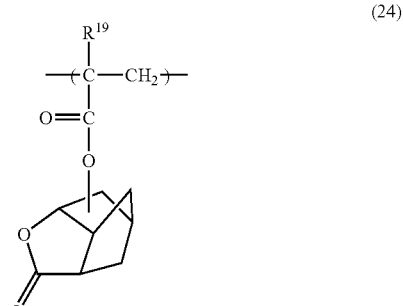

(24)

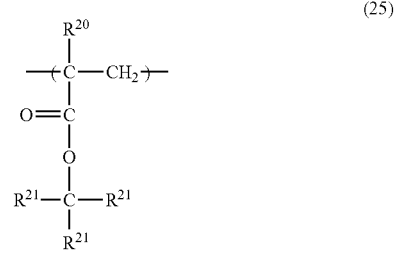

(25)

wherein $R^{17}$, $R^{19}$, and $R^{20}$ individually represent a hydrogen atom or a methyl group; $R^{18}$ individually represents a hydrogen atom, hydroxyl group, cyano group, or —COOR$^{22}$, wherein $R^{22}$ is a hydrogen atom, a linear or branched alkyl group having 1–4 carbon atoms, or a cyclic alkyl group having 3–20 carbon atoms; $R^{21}$ individually represents a monovalent alicyclic hydrocarbon group having 1–4 carbon atoms or a derivative thereof or a linear or branched alkyl group having 1–4 carbon atoms, provided that at least one $R^{21}$ is an alicyclic hydrocarbon group or a derivative thereof or any two $R^{21}$ groups form, in combination and together with the carbon atom to which these groups bond, a divalent alicyclic hydrocarbon group having 4–20 carbon atoms or a derivative thereof, and the remaining $R^{21}$ group is a linear or branched alkyl group having 1–4 carbon atoms or a monovalent alicyclic hydrocarbon group having 4–20 carbon atoms or a derivative thereof.

As preferable examples of the recurring unit (23), 3-hydroxyadamantan-1-yl (meth)acrylate, 3,5-dihydroxyadamantan-1-yl (meth)acrylate, 3-cyanoadamantan-1-yl (meth)acrylate, 3-carboxyladamantan-1-yl (meth)acrylate, 3,5-dicarboxyadamantan-1-yl (meth)acrylate, 3-carboxy-5-hydroxyadamantan-1-yl (meth)acrylate, 3-methoxycarbonyl-5-hydroxyadamantan-1-yl (meth)acrylate, and the like can be given.

The recurring units (23) and recurring units (24) may be present in the resin (B2) either individually or in combinations of two or more.

As preferable examples of the recurring unit (25), 1-methyl-1-cyclopentyl (meth)acrylate, 1-ethyl-1-cyclopentyl (meth)acrylate, 1-methyl-1-cyclohexyl (meth)acrylate, 1-ethyl-1-cyclohexyl (meth)acrylate, 2-methyladamantan-2-yl (meth)acrylate, 2-ethyladamantan-2-yl (meth)acrylate, 2-n-propyladamantan-2-yl (meth)acrylate, 2-1-propyladamantan-2-yl (meth)acrylate, 2-methyladamantan-2-yl (meth)acrylate, 1-(adamantan-1-yl)-1-methylethyl (meth) acrylate, and the like can be given.

The resin (B2) may contain at least one other recurring unit.

As examples of the other recurring units, (meth) acrylic esters such as 7-oxo-6-oxabicyclo[3.2.1]octan-4-yl (meth)acrylate, 5-oxo-4-oxatricyclo[4.2.1.0$^{3,7}$]nonan-2-yl (meth)acrylate, 2-oxotetrahydropyran-4-yl (meth)acrylate, 4-methyl-2-oxotetrahydropyran-4-yl (meth)acrylate, 5-oxotetrahydrofuran-3-yl (meth)acrylate, 2-oxotetrahydrofuran-3-yl (meth)acrylate, 5-oxotetrahydrofuran-2-yl methyl (meth)acrylate, and 3,3-dimethyl-5-oxotetrahydrofuran-2-yl methyl (meth)acrylate; an unsaturated amide compound such as (meth) acrylamide, N,N-dimethyl (meth) acrylamide, crotonamide, maleinamide, fumaramide, mesaconamide, citraconamide, and itaconamide; unsaturated carboxylic anhydrides such as maleic anhydride and itaconic anhydride; mono-functional monomers such as bicycle [2.2.1]hept-2-ene and the derivative thereof and tetracyclo [6.2.1$^{3,6}$.0$^{2,7}$]dodeca-3-ene and the derivative thereof; a polyfunctional monomer such as methyleneglycol di(meth)acrylate, ethyleneglycol di(meth)acrylate, 2,5-dimethyl-2,5-hexanediol di(meth)acrylate, 1,2-adamantandiol di(meth)acrylate, 1,3-adamantandiol di(meth)acrylate, 1,4-adamantandiol di(meth)acrylate, and tricyclodecanyl dimethylol di(meth)acrylate can be given.

As a preferable example of the acid-dissociable group-containing resin (B) especially suitable for a radiation-sensitive resin composition using an $F_2$ excimer laser, an alkali insoluble or scarcely soluble polysiloxane having at least one recurring unit selected from the group consisting of the recurring unit of the following formula (26) (hereinafter referred to as "recurring unit (26)") and the recurring unit of the following formula (27) (hereinafter referred to as "recurring unit (27)") can be given (this resin is hereinafter referred to as "resin (B3)"). The resin (B3) may be suitably used in radiation-sensitive resin compositions for use with other radiations such as KrF excimer laser, ArF excimer laser, and electron beams.

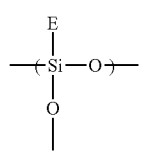
(26)

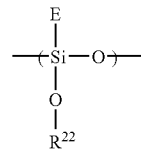
(27)

wherein E individually represents a monovalent organic group having an acid-dissociable group and R$^{22}$ represents a substituted or unsubstituted, linear, branched, or cyclic monovalent hydrocarbon group having 1–20 carbon atoms.

E is preferably a group having a structure wherein an acid-dissociable group is bonded with a group having a cyclic structure.

As a preferable group having the cyclic structure, a group having an alicyclic cyclic structure derived from a cycloalkane having 3–8 carbon atoms, tricyclodecane, tetracyclodecane, adamantine, and the like, and a group having a halogenated aromatic ring structure having 6–20 carbon atoms can be given.

As the resin (B3), a resin having the recurring unit (26) is preferable.

As specific examples of the recurring unit (26), the recurring units of the following formulas (26-1) to (26-4) can be given.

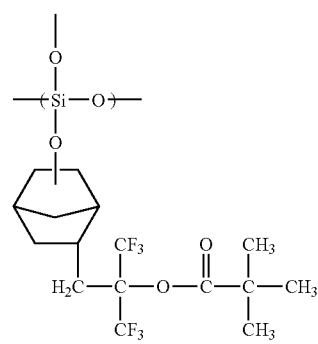
(26-1)

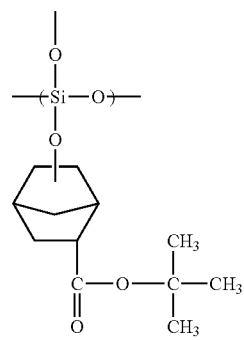
(26-2)

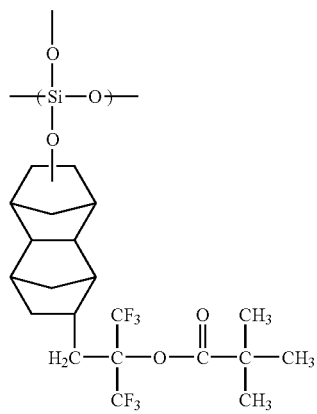

(26-3)

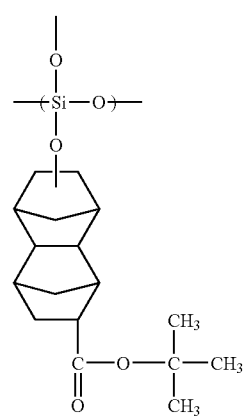

(26-4)

The resin (B3) may contain at least one other recurring unit.

As preferable examples of the other recurring unit, units obtained from hydrolysis of alkyl alkoxysilanes such as methyl trimethoxysilane, methyl triethoxysilane, ethyl trimethoxysilane, and ethyl triethoxysilane, and the recurring units of the following formulas (28-1) to (28-4) can be given.

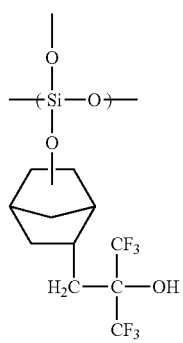

(28-1)

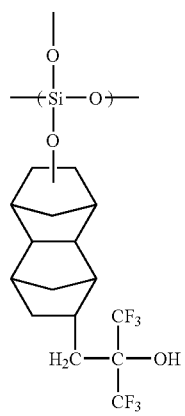

(28-2)

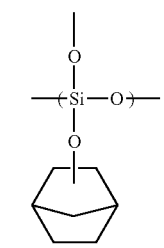

(28-3)

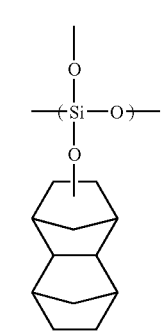

(28-4)

The resin (B3) can be prepared by polycondensation of a silane compound containing an acid-dissociable group or by introducing an acid-dissociable group into a previously prepared polysiloxane.

When polymerizing the acid-dissociable group-containing silane compound, an acidic catalyst is preferably used as the catalyst, and after polymerization of the silane compound in the presence of the acidic catalyst, a further reaction is preferably continued in the presence of a basic catalyst.

As examples of the acidic catalyst, inorganic acids such as hydrochloric acid, sulfuric acid, nitric acid, boric acid, phosphoric acid, titanium tetrachloride, zinc chloride, and aluminium chloride and organic acids such as formic acid, acetic acid, n-propionic acid, butyric acid, valeric acid, oxalic acid, malonic acid, succinic acid, maleic acid, fumaric acid, adipic acid, phthalic acid, terephthalic acid, acetic anhydride, maleic anhydride, citric acid, benzenesulfonic acid, p-toluenesulfonic acid, and methanesulfonic acid can be given.

Of these acidic catalysts, hydrochloric acid, sulfuric acid, acetic acid, oxalic acid, malonic acid, maleic acid, fumaric acid, acetic anhydride, maleic anhydride, and the like are preferable.

These acidic catalysts may be used either individually or in combination of two or more.

As examples of the basic catalyst, inorganic bases such as lithium hydroxide, sodium hydroxide, potassium hydroxide, calcium hydroxide, barium hydroxide, sodium hydrogencarbonate, potassium hydrogencarbonate, sodium carbonate, and potassium carbonate and organic bases such as triethylamine, tri-n-propylamine, tri-n-butylamine, and pyridine can be given.

These basic catalysts may be used either individually or in combination of two or more.

When the acid-dissociable group-containing resin (B) is prepared by a reaction or reactions comprising the polymerization of a polymerizable unsaturated monomer, a branched structure may be introduced into the acid-dissociable group-containing resin by a unit derived from a polyfunctional monomer having two or more polymerizable unsaturated bonds and/or by an acetal crosslinking group. Introduction of the branched structure improves the heat resistance of the acid-dissociable group-containing resin (B).

The amount of the branched structure introduced into the acid-dissociable group-containing resin (B) is preferably 10 mol % or less of the total amount of recurring units, although such an amount varies depending on the type of branched structure and the type of acid-dissociable group-containing resin into which the branched structure is introduced.

The molecular weight of the acid-dissociable group-containing resin (B) may be appropriately selected without any restrictions. The polystyrene-reduced weight average molecular weight (hereinafter referred to as "Mw") of the acid-dissociable group-containing resin (B) determined by gel permeation chromatography (GPC) is usually 1,000–500,000, preferably 2,000–400,000, and still more preferably 3,000–300,000.

The Mw of the acid-dissociable group-containing resin (B) not having a branched structure is preferably 1,000–150,000, and particularly preferably 3,000–100,000. The Mw of the acid-dissociable group-containing resin (B) having a branched structure is preferably 5,000–500,000, and particularly preferably 8,000–300,000. The resist obtained from the acid-dissociable group-containing resin (B) having an Mw in the above range possesses excellent development characteristics.

The ratio of Mw to the polystyrene-reduced number average molecular weight (hereinafter referred to as "Mn") determined by GPC (Mw/Mn) of the acid-dissociable group-containing resin (B) can be appropriately selected without any restrictions, and is usually 1–10, preferably 1–8, and particularly preferably 1–5. The resist obtained from the acid-dissociable group-containing resin (B) having a Mw/Mn in the above range possesses excellent resolution performance.

There are no restrictions to the method for manufacturing the acid-dissociable group-containing resin (B) As examples of the method for manufacturing, a method of introducing one or more acid-dissociable groups into an acidic functional group of an alkali-soluble resin which has previously been manufactured, a method of polymerizing polymerizable unsaturated monomers having an acid-dissociable group, optionally together with other polymerizable unsaturated monomers, a method of polycondensing one or more polycondensation components having an acid-dissociable group, optionally together with other polycondensation components, and the like can be given.

The polymerization of the polymerizable unsaturated monomers and the polymerization of the one or more polymerizable unsaturated monomers possessing an acid-dissociable group in the manufacture of the alkali soluble resin is carried out by block polymerization, solution polymerization, precipitation polymerization, emulsion polymerization, suspension polymerization, block-suspension polymerization, or the like using an appropriate polymerization initiator or catalyst such as a radical polymerization initiator, anionic polymerization catalyst, conjugated anionic polymerization catalyst, cationic polymerization catalyst, or the like according to the type of polymerizable unsaturated monomer or reaction media.

The polycondensation of the one or more polycondensation components having an acid-dissociable group is preferably carried out in the presence of an acidic catalyst using an aqueous medium or a mixture of water and a hydrophilic solvent.

The amount of the acid generator (A) used in the positive-tone radiation-sensitive resin composition of the present invention can be appropriately selected depending on the desired properties of the resist. The acid generator (A) is preferably used in an amount of 0.001–70 parts by weight, more preferably 0.01–50 parts by weight, and particularly preferably 0.1–20 parts by weight for 100 parts by weight of the acid-dissociable group-containing resin (B). Using the acid generator (A) in an amount of 0.001 parts by weight or more prevents deterioration of the sensitivity and resolution of the resist. Also, using the acid generator (A) in an amount of 70 parts by weight or less prevents deterioration of the applicability and pattern shape of the resist.

Acid Diffusion Controller

An acid diffusion controller is preferably added to the positive-tone radiation-sensitive resin composition of the present invention. The acid diffusion controller controls diffusion of an acid generated from the acid generator (A) upon exposure in the resist film and prevents unfavorable chemical reactions in the unexposed region. Addition of the acid diffusion controller further improves storage stability of the resulting radiation-sensitive resin composition and resolution of the resist. Moreover, addition of the acid diffusion controller prevents the line width of the resist pattern from changing due to changes in the post-exposure delay (PED) between exposure and development, whereby a radiation-sensitive resin composition with remarkably superior process stability can be obtained.

As the acid diffusion controller, nitrogen-containing organic compounds of which the basicity does not change due to exposure or heat treatment during formation of a resist pattern are preferable.

As examples of the nitrogen-containing organic compounds, a compound shown by the following formula (29) (hereinafter referred to as "nitrogen-containing compound (I)"), a diamino compound having two nitrogen atoms in the molecule (hereinafter referred to as "nitrogen-containing compound (II)"), a polyamino compound or polymer having three or more nitrogen atoms in the molecule (hereinafter referred to as "nitrogen-containing compound (III)"), an amide group-containing compound, urea compound, nitrogen-containing heterocyclic compound, and the like can be given:

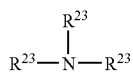

(29)

wherein $R^{23}$ individually represents a hydrogen atom, alkyl group, aryl group, or aralkyl group which may be substituted or unsubstituted.

Given as examples of the substituted or unsubstituted alkyl group represented by $R^{23}$ in the above formula (29) are groups having 1–15 carbon atoms and preferably 1–10 carbon atoms including specific examples such as a methyl group, ethyl group, n-propyl group, i-propyl group, n-butyl group, i-butyl group, sec-butyl group, t-butyl group, n-pentyl group, neopentyl group, n-hexyl group, thexyl group, n-heptyl group, n-octyl group, n-ethylhexyl group, n-nonyl group, and n-decyl group.

Given as examples of the substituted or unsubstituted aryl group represented by $R^{23}$ are groups having 6–12 carbon atoms including specific examples such as a phenyl group, tolyl group, xylyl group, cumenyl group, and 1-naphthyl group.

Given as examples of the substituted or unsubstituted aralkyl group represented by $R^{23}$ are groups having 7–19 carbon atoms and preferably 7–13 carbon atoms including specific examples such as a benzyl group, a-methylbenzyl group, phenethyl group, and 1-naphthylmethyl group.

Examples of the nitrogen-containing compounds (I) include monoalkylamines such as n-hexylamine, n-heptylamine, n-octylamine, n-nonylamine, and n-decylamine; dialkylamines such as di-n-butylamine, di-n-pentylamine, di-n-hexylamine, di-n-heptylamine, di-n-octylamine, di-n-nonylamine, and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine, and tri-n-decylamine; aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine; and alkanolamines such as ethanolamine, diethanolamine, and triethanolamine.

Examples of the nitrogen-containing compounds (II) include ethylenediamine, N,N,N',N'-tetramethylethylenediamine, tetramethylenediamine, hexamethylenediamine, N,N,N',N'-tetrakis(2-hydroxyethyl)ethylenediamine, N,N,N',N'-tetrakis(2-hydroxypropyl)ethylenediamine, 4,4'-diaminodiphenylmethane, 4,4'-diamino diphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

As examples of the nitrogen-containing compound (III), polyethyleneimine, polyallylamine, a polymer of dimethylaminoethylacrylamide, and the like can be given.

Examples of compounds containing an amide group include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of urea compounds include urea, methylurea, 1,1-dimethylurea, 1,3-dimethylurea, 1,1,3,3-tetramethylurea, 1,3-diphenylurea, and tributylthiourea.

Examples of the nitrogen-containing heterocyclic compounds include imidazoles such as imidazole, benzimidazole, 2-methylimidazole, 4-methylimidazole, 1,2-dimethylimidazole, 2-phenylimidazole, 4-phenylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, N-methyl-4-phenylpyridine, nicotine, nicotinic acid, nicotinamide, quinoline, 8-oxyquinoline, and acridine; pyrazine, pyrazole, pyridazine, quinoxaline, purine, pyrrolidine, piperidine, 1-piperidine ethanol, 2-piperidine ethanol, 3-piperidine-1,2-propanediol, morpholine, 4-methylmorpholine, piperazine, 1,4-dimethylpiperazine, and 1,4-diazabicyclo[2.2.2]octane.

A compound having an acid-dissociable group can also be used as the nitrogen-containing organic compound.

As examples of the nitrogen-containing organic compound having an acid-dissociable group,
N-(t-butoxycarbonyl)piperidine,
N-(t-butoxycarbonyl)imidazole,
N-(t-butoxycarbonyl)benzimidazole,
N-(t-butoxycarbonyl)-2-phenylbenzimidazole,
N-(t-butoxycarbonyl)dioctylamine,
N-(t-butoxycarbonyl)diethanolamine,
N-(t-butoxycarbonyl)dicyclohexylamine, and
N-(t-butoxycarbonyl)diphenylamine can be given.

Of these nitrogen-containing organic compounds, the nitrogen-containing compounds (I), nitrogen-containing compounds (II), nitrogen-containing heterocyclic compounds, and the like are preferable.

The acid diffusion controllers may be used either individually or in combination of two or more.

The amount of the acid diffusion controller to be added is preferably 15 parts by weight or less, more preferably 0.001–10 parts by weight, and particularly preferably 0.005–5 parts by weight for 100 parts by weight of the acid-dissociable group-containing resin (B). Incorporating the acid diffusion controller in an amount of 0.001 parts by weight or more prevents deterioration of the pattern shape and size fidelity as a resist. Also, incorporating the acid diffusion controller in an amount of 15 parts by weight or less improves the sensitivity as a resist and improves the developability of the exposure area.

Dissolution Controller

A dissolution controller that improves the solubility in an alkaline developer by the action of an acid may be added to the positive-tone radiation sensitive resin composition of the present invention.

As examples of such a dissolution controller, compounds having an acid functional group such as a phenolic hydroxyl group, carboxyl group, and sulfonic group, compounds in which the hydrogen atom in the acidic functional group is replaced by an acid-dissociable group, and the like can be given.

These dissolution controllers may be used either individually or in combination of two or more. The proportion of the dissolution controllers to be added is 10 parts by weight or less, and preferably 5 parts by weight or less for 100 parts by weight of the total resin component in the radiation-sensitive resin composition.

Surfactant

A surfactant that improves applicability, striation, developability, and the like may be added to the positive-tone radiation sensitive resin composition of the present invention.

As the surfactants, any of anionic surfactants, cationic surfactants, nonionic surfactants, and ampholytic surfactants may be used. Of these, nonionic surfactants are preferable.

As examples of nonionic-type surfactants, polyoxyethylene higher alkyl ethers, polyoxyethylene higher alkyl phenyl ethers, higher fatty acid diesters of polyethylene glycol, commercially available products such as KP (manufactured by Shin-Etsu Chemical Co., Ltd.), Polyflow (manufactured by Kyoeisha Chemical Co., Ltd.), EFTOP (manufactured by TOHKEM PRODUCTS CORPORATION), MEGAFAC (manufactured by Dainippon Ink and Chemicals, Inc.), Fluorad (manufactured by Sumitomo 3M, Ltd.), Asahi Guard, Surflon (manufactured by Asahi Glass Co., Ltd.), and the like can be given.

These surfactants may be used either individually or in combination of two or more. The proportion of the surfactants to be added is 2 parts by weight or less, and preferably 1.5 parts by weight or less, as an effective component, for 100 parts by weight of the total resin components in the radiation-sensitive resin composition.

Sensitizer

Sensitizers can be added to the positive-tone radiation sensitive resin composition of the present invention. These sensitizers absorb radiation energy and transmit the energy to the acid generator (A), thereby increasing the amount of an acid to be generated upon exposure and improving the apparent sensitivity of the radiation-sensitive resin composition.

As examples of sensitizers, acetophenones, benzophenones, naphthalenes, biacetyl, eosine, rose bengale, pyrenes, anthracenes, phenothiazines, and the like can be given.

These sensitizers may be used either individually or in combinations of two or more. The proportion of the sensitizers to be added is 50 parts by weight or less, and preferably 30 parts by weight or less for 100 parts by weight of the total resin component in the radiation-sensitive resin composition.

Other Additives

Other additives may be added to the positive-tone radiation sensitive resin composition of the present invention, as required, to the extent that does not impair the effects of the present invention. Examples of such additives include dyes, paints, adhesion adjuvants, halation inhibitors, preservatives, defoaming agents, shape improvers. Specific additives include 4-hydroxy-4'-methylchalcone, and the like.

Addition of a dye or a pigment visualizes a latent image in the exposed area, thereby decreasing the effects of halation during exposure. Use of an adhesion improver improves adhesion to the substrates.

Preparation of Composition Solution

The positive-tone radiation-sensitive resin composition of the present invention is usually prepared as a composition solution by dissolving the components in a solvent to obtain a homogeneous solution and, optionally, filtering the solution through a filter with a pore size of about 0.2 μm.

Ethers, esters, ether esters, ketones, ketone esters, amides, amide esters, lactams, lactones, and (halogenated) hydrocarbons are given as examples of the solvent which can be used here. Specific examples are ethylene glycol monoalkyl ethers, diethylene glycol dialkyl ethers, propylene glycol monoalkyl ethers, propylene glycol dialkyl ethers, ethylene glycol monoalkyl ether acetates, acetates, hydroxy acetates, lactates, alkoxy acetates, (non)cyclic ketones, acetoacetates, pyruvates, propionates, N,N-dialkyl formamides, N,N-dialkyl acetamides, N-alkylpyrolidones, γ-lactones, (halogenated) aliphatic hydrocarbons, and (halogenated) aromatic hydrocarbons.

More specifically, such solvents include ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, propylene glycol monomethyl ether acetate, propylene glycol monoethyl ether acetate, propylene glycol mono-n-propyl ether acetate, isopropenyl acetate, isopropenyl propionate, toluene, xylene, methyl ethyl ketone, cyclohexanone, 2-heptanone, 3-heptanone, 4-heptanone, ethyl 2-hydroxypropionate, ethyl 2-hydroxy-2-methyl propionate, ethyl ethoxyacetate, ethyl hydroxyacetate, methyl 2-hydroxy-3-methylbutyrate, methyl lactate, ethyl lactate, n-propyl lactate, i-propyl lactate, 3-methoxybutyl acetate, 3-methyl-3-methoxybutyl acetate, 3-methyl-3-methoxybutyl propionate, 3-methyl-3-methoxybutyl butyrate, ethyl acetate, n-propyl acetate, n-butyl acetate, methyl acetoacetate, ethyl acetoacetate, methyl 3-methoxy propionate, ethyl 3-methoxypropionate, methyl 3-ethoxypropionate, ethyl 3-ethoxypropionate, N-methylpyrolidone, N,N-dimethyl formamide, and N,N-dimethyl acetamide.

Of these solvents, propylene glycol monoalkyl ether acetates, 2-heptanone, lactates, 2-hydroxypropionates, 3-alkoxypropionates, and the like are desirable to ensure excellent uniformity of the film surface during application.

These solvents may be used either individually or in combination of two or more.

One or more solvents with a high boiling point may optionally be added to the solvent. Examples of such solvents with a high boiling point include benzyl ethyl ether, di-n-hexyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and ethylene glycol monophenyl ether acetate.

These other solvents may be used either individually or in combination of two or more.

The proportion of the other solvents to be added is 50 wt % or less, and preferably 30 wt % or less of the total amount of solvents used.

The solvents are used in a total amount to make the total solid content of the solution composition usually 5–50 wt %, preferably 10–50 wt %, more preferably 10–40 wt %, and particular preferably 10–30 wt %. An optimal amount 10–25 wt %. The total solid content in the above ranges is desirable to ensure excellent uniformity of the film surface during application.

Formation of Resist Pattern

A resist pattern is formed from the positive-tone radiation-sensitive resin composition of the present invention by applying the composition solution thus prepared to, for example, substrates such as a silicon wafer or a wafer coated with aluminum using an appropriate application method such as rotational coating, cast coating, and roll coating to form a resist film. The resist film is then optionally pre-baked. After the pre-baking (hereinafter referred to as "PB"), the resist film is exposed to radiation through a mask with a prescribed pattern.

As radiation that can be used here, far ultraviolet rays such as a bright line spectrum of a mercury lamp (wavelength: 254 nm), KrF excimer laser (wavelength: 248 nm), ArF excimer laser (wavelength: 193 nm), $F_2$ excimer laser (wavelength: 157 nm), and EUV (wavelength: 13 nm); X-rays such as synchrotron radiation, charged particle rays such as electron beams, and the like can be used according to the types of acid generator (A). Of these, far ultraviolet rays and charged particle rays are preferable. Particular preferable radiations are a KrF excimer laser (wavelength: 248 nm), ArF excimer laser (wavelength: 193 nm), and electron beams.

The exposure conditions such as the dose of radiation are appropriately determined according to the composition of the positive-tone radiation-sensitive resin composition, types of additives, and the like.

During formation of the resist pattern, the resist is preferably heated after exposure (this heating treatment is hereinafter referred to as "PEB") to improve apparent sensitivity of the resist.

PEB is performed at a temperature of 30–200° C., and preferably 50–150° C., although the temperature varies depending on the composition of the radiation-sensitive resin composition, types of additives, and the like.

The resist film after exposure is developed in an alkaline developer to form a predetermined resist pattern.

As the alkaline developer, an alkaline aqueous solution in which one or more alkaline compounds such as an alkaline metal hydroxide, aqueous ammonia, alkylamines, alkanolamines, heterocyclic amines, tetraalkylammonium hydroxides, choline, 1,8-diazabicyclo[5.4.0]-7-undecene, and 1,5-diazabicyclo[4.3.0]-5-nonene are dissolved is used. An aqueous solution of tetraalkylammonium hydroxide is a particular preferable alkaline developer.

The concentration of the alkaline aqueous solution is preferably 10 wt % or less, more preferably 1–10 wt %, and particularly preferably 2–5 wt %. The concentration of the alkaline aqueous solution less than 10 wt % prevents dissolution of an unexposed area in the developer.

The addition of an appropriate amount of a surfactant to the alkaline aqueous solution is desirable to increase wettability of the resist to the developer.

After development using the alkaline aqueous solution developer, the resist film is generally washed with water and dried.

EXAMPLES

The embodiments of the present invention are described in more detail by examples. However, these examples should not be construed as limiting the present invention.

Synthesis of Acid Generator

Synthesis Example 1

30 g of 4-hydroxyphenyl diphenylsulfonium nonafluoro-n-butanesulfonate was dissolved in 300 g of dichloromethane in a reaction flask, in which the atmosphere was replaced with nitrogen. 17.9 g of n-butanesulfonyl chloride and 10.5 g of triethylamine were added in this order. The mixture was stirred for 20 minutes at room temperature. After the addition of 100 g of ion-exchanged water, the mixture was transferred to a separatory funnel, shaken, and allowed to stand still. The water layer was removed. After the addition of 300 ml of distilled water, the solution was shaken and allowed to stand still. The water layer was removed. The resulting dichloromethane solution was dried using anhydrous magnesium sulfate and filtered. After evaporating dichloromethane from the dichloromethane solution, the residual liquid was dried under reduced pressure to obtain 26.7 g of 4-n-butanesulfonyloxyphenyl diphenylsulfonium nonafluoro-n-butanesulfonate. This compound is indicated as "acid generator (A-1)".

Synthesis Example 2

30 g of 4-hydroxyphenyl diphenylsulfonium nonafluoro-n-butanesulfonate was dissolved in 300 g of dichloromethane in a reaction flask, in which the atmosphere was replaced with nitrogen. 33.1 g of nonafluoro-n-butanesulfonyl chloride and 10.5 g of triethylamine were added in this order. The mixture was stirred for 20 minutes at room temperature. After the addition of 100 g of ion-exchanged water, the mixture was transferred to a separatory funnel, shaken, and allowed to stand still. The water layer was removed. After the addition of 300 ml of distilled water, the solution was shaken and allowed to stand still. The water layer was removed. The resulting dichloromethane solution was dried using anhydrous magnesium sulfate and filtered. After evaporating dichloromethane from the dichloromethane solution, the residual liquid was dried under reduced pressure to obtain 26.7 g of 4-nonafluoro-n-butanesulfonyloxyphenyl diphenylsulfonium nonafluoro-n-butanesulfonate. This compound is indicated as "acid generator (A-2)".

Synthesis Example 3

30 g of 4-hydroxyphenyl diphenylsulfonium nonafluoro-n-butanesulfonate was dissolved in 300 g of dichloromethane in a reaction flask, in which the atmosphere was replaced with nitrogen. 30.6 g of 1,1,2,2-tetrafluoro-2-(norbornan-2-yl)ethanesulfonyl chloride and 10.5 g of triethylamine were added in this order. The mixture was stirred for 20 minutes at room temperature. After the addition of 100 g of ion-exchanged water, the mixture was transferred to a separatory funnel, shaken, and allowed to stand still. The water layer was removed. After the addition of 300 ml of distilled water, the solution was shaken and allowed to stand still. The water layer was removed. The resulting dichloromethane solution was dried using anhydrous magnesium sulfate and filtered. After evaporating dichloromethane from the dichloromethane solution, the residual liquid was dried under reduced pressure to obtain 23.5 g of 4-[1,1,2,2-tetrafluoro-2-(norbornan-2-yl)ethanesulfonyloxy]phenyl diphenylsulfonium nonafluoro-n-butanesulfonate. This compound is indicated as "acid generator (A-3)".

Synthesis Example 4

30 g of 4-hydroxyphenyl diphenylsulfonium nonafluoro-n-butanesulfonate was dissolved in 300 g of dichloromethane in a reaction flask, in which the atmosphere was replaced with nitrogen. 26.0 g of 10-camphorsulfonyl chloride and 10.5 g of triethylamine were added in this order. The mixture was stirred for 20 minutes at room temperature. After the addition of 100 g of ion-exchanged water, the mixture was transferred to a separatory funnel, shaken, and allowed to stand still. The water layer was removed. After the addition of 300 ml of distilled water, the solution was shaken and allowed to stand still. The water layer was removed. The resulting dichloromethane solution was dried using anhydrous magnesium sulfate and filtered. After evaporating dichloromethane from the dichloromethane solution, the residual liquid was dried under reduced pressure to obtain 38.6 g of 4-(10-camphorsulfonyloxy)phenyl diphenylsulfonium nonafluoro-n-butanesulfonate. This compound is indicated as "acid generator (A-4)".

Synthesis Example 5

30 g of 4-hydroxyphenyl diphenylsulfonium nonafluoro-n-butanesulfonate was dissolved in 300 g of dichloromethane in a reaction flask, in which the atmosphere was replaced with nitrogen. 19.7 g of p-tosylsulfonyl chloride and 10.5 g of triethylamine were added in this order. The mixture was stirred for 20 minutes at room temperature. After the addition of 100 g of ion-exchanged water, the mixture was transferred to a separatory funnel, shaken, and allowed to stand still. The water layer was removed. After the addition of 300 ml of distilled water, the solution was shaken and allowed to stand still. The water layer was removed. The resulting dichloromethane solution was dried using anhydrous magnesium sulfate and filtered. After evaporating dichloromethane from the dichloromethane solution, the residual liquid was dried under reduced pressure to obtain 12.6 g of 4-(p-tosylsulfonyloxy)phenyl diphenylsulfonium nonafluoro-n-butanesulfonate. This compound is indicated as "acid generator (A-5)".

Synthesis Example 6

30 g of 4-hydroxyphenyl diphenylsulfonium 1,1,2,2-tetrafluoro-2-(norbornan-2-yl)ethanesulfonate was dissolved in 300 g of dichloromethane in a reaction flask, in which the atmosphere was replaced with nitrogen. 30.6 g of 1,1,2,2-tetrafluoro-2-(norbornan-2-yl)ethanesulfonyl chloride and 10.5 g of triethylamine were added in this order. The mixture was stirred for 20 minutes at room temperature. After the addition of 100 g of ion-exchanged water, the mixture was transferred to a separatory funnel, shaken, and allowed to stand still. The water layer was removed. After the addition of 300 ml of distilled water, the solution was shaken and allowed to stand still. The water layer was removed. The resulting dichloromethane solution was dried using anhydrous magnesium sulfate and filtered. After evaporating dichloromethane from the dichloromethane solution, the residual liquid was dried under reduced pressure to obtain 23.5 g of 4-[1,1,2,2-tetrafluoro-2-(norbornan-2-yl)ethanesulfonyloxy]phenyl diphenylsulfonium nonafluoro-n-butanesulfonate. This compound is indicated as "acid generator (A-6)".

Synthesis Example 7

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution, 5.8 g of tetra-n-butylammonium bromide, and 6.71 g of n-butanethiol were added. The mixture was stirred for 30 minutes at room temperature and transferred to a separatory funnel, shaken, and allowed to stand still. The water layer was removed. After the addition of 300 ml of distilled water, the mixture was shaken and allowed to stand still. The water layer was removed. The resulting dichloromethane solution was dried with anhydrous magnesium sulfate, filtered, and dried using an evaporator. After evaporating dichloromethane from the dried solution, the residual liquid was dried under reduced pressure to obtain 17.8 g of 4-n-butylthiophenyl diphenylsulfonium trifluoromethanesulfonate.

17.8 g of the resulting 4-n-butylthiophenyl diphenylsulfonium trifluoromethanesulfonate was dissolved in 100 g of methanol in a reaction flask. The mixture was fed into an ion-exchange chromatography (an ion-exchange resin: Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 15 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was further added and the solution was shaken and allowed to stand still. The water layer was removed. The resulting dichloromethane solution was dried with anhydrous magnesium sulfate, filtered, and dried using an evaporator. After evaporating dichloromethane from the dried solution, the residual liquid was dried under reduced pressure to obtain 21.1 g of 4-n-butylthiophenyl diphenylsulfonium nonafluoro-n-butanesulfonate.

21.1 g of the resulting 4-n-butylthiophenyl diphenylsulfonium nonafluoro-n-butanesulfonate was dissolved in 300 ml of methanol in a reaction flask. 18 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was further added and the solution was shaken and allowed to stand still. The water layer was removed. The resulting dichloromethane solution was dried with anhydrous magnesium sulfate, filtered, and dried using an evaporator. After evaporating dichloromethane from the dried solution, the residual liquid was dried under reduced pressure to obtain 14.4 g of 4-n-butylsulfonylphenyl diphenylsulfonium nonafluoro-n-butanesulfonate. This compound is indicated as "acid generator (A-7)".

Synthesis Example 8

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution, 5.8 g of tetra-n-butylammonium bromide, and 6.71 g of cyclohexane thiol were added. The mixture was stirred for 30 minutes at room temperature and transferred to a separatory funnel, shaken, and allowed to stand still. The water layer was removed. After the addition of 300 ml of distilled water, the mixture was shaken and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 19.2 g of 4-cyclohexylthiophenyl diphenylsulfonium trifluoromethane sulfonate.

19.2 g of the resulting 4-cyclohexylthiophenyl diphenylsulfonium trifluoromethane sulfonate was dissolved in 100 g of methanol in a reaction flask. The mixture was fed into an ion-exchange chromatography (an ion-exchange resin:

Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 15 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was further added and the solution was shaken and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 20.5 g of 4-cyclohexylthiophenyl diphenylsulfonium nonafluoromethane-n-butanesulfonate.

20.5 g of the resulting 4-cyclohexylthiophenyl diphenylsulfonium nonafluoromethane-n-butanesulfonate was dissolved in 300 ml of methanol in a reaction flask. 18 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the solution was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 15.5 g of 4-cyclohexylsulfonylphenyl diphenylsulfonium nonafluoro-n-butanesulfonate. This compound is indicated as "acid generator (A-8)".

Synthesis Example 9

26.7 g of tris(4-fluorophenyl)sulfonium trifluoromethanesulfonate was dissolved in 200 g of dichloromethane in a reaction flask, in which the atmosphere was replaced with nitrogen. 600 g of 10 wt % sodium hydroxide aqueous solution, 5.8 g of tetra-n-butylammonium bromide, and 20.1 g of n-butanethiol were added. The mixture was stirred for 30 minutes at room temperature and transferred to a separatory funnel, shaken, and allowed to stand still. The water layer was removed. After the addition of 300 ml of distilled water, the mixture was shaken and allowed to stand still. The water layer was removed. The dichloromethane solution was dried with anhydrous magnesium sulfate and filtered. After evaporating dichloromethane from the dried solution, the residual liquid was dried under reduced pressure to obtain 23.4 g of tris(4-n-butylthiophenyl)sulfonium trifluoromethanesulfonate.

23.4 g of the resulting tris(4-n-butylthiophenyl) sulfonium trifluoromethanesulfonate was dissolved in 100 g of methanol in a reaction flask. The mixture was fed into an ion-exchange chromatography (an ion-exchange resin: Shephadex R-QAE A-25, packing amount: 180 g, manufactured by Aldrich Corporation) to replace trifluoromethanesulfonate anions with chlorine ions. After evaporating methanol using an evaporator, the resulting residue was dissolved in 300 g of dichloromethane. 45 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was added and the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 25.2 g of tris(4-n-butylthiophenyl)sulfonium nonafluoro-n-butanesulfonate.

25.2 g of the resulting tris(4-n-butylthiophenyl) sulfonium nonafluoro-n-butanesulfonate was dissolved in 300 ml of methanol in a reaction flask. 54 g of 30 wt % hydrogen peroxide solution and 30 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 20.1 g of tris(4-n-butylsulfonylphenyl)sulfonium nonafluoro-n-butanesulfonate. This compound is indicated as "acid generator (A-9)".

Synthesis Example 10

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution and 11.8 g of 1,4-dioxaspiro[4.5]decane-7-thiol were added. The mixture was stirred for 30 minutes at room temperature and transferred to a separatory funnel, shaken, and allowed to stand still. The water layer was removed. After the addition of 300 ml of distilled water, the mixture was further shaken and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 25.3 g of [4-(1,4-dioxaspiro[4.5]decan-7-ylsulfonyl)phenyl]diphenylsulfonium trifluoromethanesulfonate.

25.3 g of the resulting [4-(1,4-dioxaspiro[4.5]decan-7-ylsulfonyl)phenyl]diphenylsulfonium trifluoromethanesulfonate was dissolved in 100 g of methanol in a reaction flask. The mixture was fed into an ion-exchange chromatography (an ion-exchange resin: Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 58 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 31.5 g of [4-(1,4-dioxaspiro[4.5]decan-7-ylsulfanyl)phenyl]diphenylsulfonium nonafluoro-n-butanesulfonate.

31.5 g of the resulting [4-(1,4-dioxaspiro[4.5]decan-7-ylsulfanyl)phenyl]diphenylsulfonium nonafluoro-n-butanesulfonate was dissolved in 300 ml of methanol in a reaction flask. 30 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 30.5 g of [4-(1,4-dioxaspiro[4.5]decan-7-ylsulfonyl)phenyl]diphenylsulfonium nonafluoro-n-butanesulfonate. This compound is indicated as "acid generator (A-10)".

Synthesis Example 11

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution and 14.6 g of 3,3-dimethyl-1,5-dioxaspiro[5.5]undecane-7-thiol were added. The mixture was stirred at 30 minutes for room temperature and transferred to a separatory funnel, shaken, and allowed to stand still. The water layer was removed. After the addition of 300 ml of distilled water, the mixture was further shaken and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 25.6 g of [4-(3,3-dimethyl-1,5-dioxaspiro[5.5]undecan-7-ylsulfonyl)phenyl]diphenylsulfonium trifluoromethanesulfonate.

25.6 g of the resulting [4-(3,3-dimethyl-1,5-dioxaspiro[5.5]undecan-7-ylsulfonyl)phenyl]diphenylsulfonium trifluoromethanesulfonate was dissolved in 100 g of methanol in a reaction flask. The mixture was fed into an ion-exchange chromatography (an ion-exchange resin: Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 60 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was added and the mixture was further shaken and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 30.5 g of [4-(3,3-dimethyl-1,5-dioxaspiro[5.5]undecan-7-ylsulfanyl)phenyl]diphenylsulfonium nonafluoro-n-butanesulfonate.

30.5 g of the resulting [4-(3,3-dimethyl-1,5-dioxaspiro[5.5]undecan-7-ylsulfanyl)phenyl]diphenylsulfonium nonafluoro-n-butanesulfonate was dissolved in 300 ml of methanol in a reaction flask. 30 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the solution was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 29.2 g of [4-(3,3-dimethyl-1,5-dioxaspiro[5.5]undecan-7-ylsulfonyl)phenyl]diphenylsulfonium nonafluoro-n-butanesulfonate. This compound is indicated as "acid generator (A-11)".

Synthesis Example 12

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution and 8.7 g of bicyclo[2.2.1]heptane-2-thiol were added. The mixture was stirred for 30 minutes at room temperature and transferred to a separatory funnel, shaken, and allowed to stand still. The water layer was removed. After the addition of 300 ml of distilled water, the solution was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 25.6 g of [4-(bicyclo[2.2.2]heptan-2-ylsulfanyl)phenyl]diphenylsulfonium trifluoromethanesulfonate.

25.6 g of the resulting [4-(bicyclo[2.2.2]heptan-2-ylsulfanyl)phenyl]diphenylsulfonium trifluoromethanesulfonate was dissolved in 100 g of methanol in a reaction flask. The mixture was fed into an ion-exchange chromatography (an ion-exchange resin: Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 60 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was added and the mixture was further shaken and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 27.4 g of [4-(bicyclo[2.2.2]heptan-2-ylsulfanyl)phenyl]diphenylsulfonium nonafluoro-n-butanesulfonate.

27.4 g of the resulting [4-(bicyclo[2.2.2]heptan-2-ylsulfanyl)phenyl]diphenylsulfonium nonafluoro-n-butanesulfonate was dissolved in 300 ml of methanol in a reaction flask. 18 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the solution was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 23.5 g of [4-(bicyclo[2.2.2]heptan-2-ylsulfonyl)phenyl]diphenylsulfonium nonafluoro-n-butanesulfonate. This compound is indicated as "acid generator (A-12)".

Synthesis Example 13

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution and 6.71 g of methane thiol were added. The mixture was stirred for 30 minutes at room temperature and transferred to a separatory funnel, shaken, and allowed to stand still. The water layer was removed. After the addition of 300 ml of distilled water, the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 19.8 g of 4-methylthiophenyl diphenylsulfonium trifluoromethane sulfonate.

19.8 g of the resulting 4-methylthiophenyl diphenylsulfonium trifluoromethane sulfonate was dissolved in 100 g of methanol in a reaction flask. The mixture was fed into an ion-exchange chromatography (an ion-exchange resin: Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 15 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was added and the solution was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 21.8 g of 4-methylthiophenyl diphenylsulfonium nonafluoro-n-butanesulfonate.

21.8 g of the resulting 4-methylthiophenyl diphenylsulfonium nonafluoro-n-butanesulfonate was dissolved in 300 ml of methanol in a reaction flask. 18 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 18.5 g of 4-methylsulfonylphenyl diphenylsulfonium nonafluoro-n-butanesulfonate. This compound is indicated as "acid generator (A-13)".

Synthesis Example 14

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution and 15.2 g of anthracen-9-ylmethanethiol were added. The mixture was stirred for 30 minutes at room temperature and transferred to a separatory funnel, shaken, and allowed to stand still. The water layer was removed. After the addition of 300 ml of distilled water, the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 27.2 g of [4-(anthracen-9-ylmethanesulfanyl)phenyl]diphenylsulfonium trifluoromethane sulfonate.

27.2 g of the resulting [4-(anthracen-9-ylmethanesulfanyl)phenyl]diphenylsulfonium trifluoromethane sulfonate was dissolved in 100 g of methanol in a reaction flask. The mixture was put through an ion-exchange chromatography (an ion-exchange resin: Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 60 g of 30 wt % nonafluoro-n-butane sulfonic acid ammonium aqueous solution was added. The mixture was stirred for one hour at room temperature and transferred to a separatory funnel, shaken, and allowed to stand still. The water layer was removed. 100 ml of distilled water was added and the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 28.2 g of [4-(anthracen-9-ylmethanesulfanyl)phenyl]diphenylsulfonium nonafluoro-n-butanesulfonate.

28.2 g of the resulting [4-(anthracen-9-ylmethanesulfanyl)phenyl]diphenylsulfonium nonafluoro-n-butanesulfonate was dissolved in 300 ml of methanol in a reaction flask. 18 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 25.5 g of [4-(anthracen-9-ylmethanesulfonyl)phenyl]diphenylsulfonium nonafluoro-n-butanesulfonate. This compound is indicated as "acid generator (A-14)".

Synthesis Example 15

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution, 5.8 g of tetra-n-butylammonium bromide, and 6.71 g of cyclohexanethiol were added. The mixture was stirred for 30 minutes at room temperature and transferred to a separatory funnel, shaken, and allowed to stand still. The water layer was removed. After the addition of 300 ml of distilled water, the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 19.2 g of 4-cyclohexylthiophenyl diphenylsulfonium trifluoromethane sulfonate.

19.2 g of the resulting 4-cyclohexylthiophenyl diphenylsulfonium trifluoromethane sulfonate was dissolved in 100 g of methanol in a reaction flask. The mixture was fed into an ion-exchange chromatography (an ion-exchange resin: Shephadex R-QAE A-25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 15 g of 30 wt % 2-(bicyclo[2.2.1]heptan-2-yl)-1,1,2,2-tetrafluoroethane sodium sulfonate aqueous solution was added. The mixture was stirred for one hour at room temperature and transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 20.1 g of 4-cyclohexylthiophenyl diphenylsulfonium 2-(bicyclo[2.2.1]heptan-2-yl)-1,1,2,2-tetrafluoroethanesulfonate.

20.1 g of the resulting 4-cyclohexylthiophenyl diphenylsulfonium 2-(bicyclo[2.2.1]heptan-2-yl)-1,1,2,2-tetrafluoroethanesulfonate was dissolved in 300 ml of methanol in a reaction flask. 18 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 15.5 g of 4-cyclohexanesulfonylphenyl diphenylsulfonium 2-(bicyclo[2.2.1]heptan-2-yl)-1,1,2,2-tetrafluoroethanesulfonate. This compound is indicated as "acid generator (A-15)".

Synthesis Example 16

33.5 g of cyclohexanethiol, 37.4 g of sodium ethoxide, and 70 g of 1-iodonaphthalene was dissolved in 1 l of ethanol in a reaction flask, in which the atmosphere was replaced with nitrogen. 3.2 g of tetrakis(triphenylphosphonium)palladium was added. The mixture was stirred for 11 hours at 90° C. Ethanol was condensed under reduced pressure and 1 l of methyl isobutylketone and 1 l of distilled water were added. The mixture was transferred to a separatory funnel, shaken, and allowed to stand still. The water layer was removed. 1 l of distilled water was added and the mixture was shaken again and allowed to stand still. The water layer was removed. The resulting solution was dried with anhydrous magnesium sulfate and filtered. After further drying using an evaporator, methyl isobutylketone was evaporated from the dried solution. The residual liquid was dried under reduced pressure and was purified by a silica gel column using n-hexane as a developing solvent. The n-hexane was evaporated under reduced pressure to obtain 46 g of 1-cyclohexylthionaphthalene.

A stirring rod was placed in a fully dried eggplant type flask (100 ml). The flask was charged with 18.1 g of 1-cyclohexylthionaphthalene and 39.7 g of diphosphorus pentaoxide-methanesulfonic acid. The mixture was stirred at 0° C. while cooling in an ice bath. After the addition of 8.9 g of tetramethylene sulfoxide dropwise to the mixture over five minutes or more, the mixture was stirred at 0° C. for 10 minutes. After removing the flask from the ice bath, the mixture was stirred at 45° C. for four hours. The reaction mixture was cooled to 0° C. in an ice bath. 450 ml of ion-exchanged water and 25 wt % aqueous ammonia were added dropwise to adjust the pH of the reaction mixture to 7. After removing the flask from the ice bath, the mixture was stirred at 25° C. for one hour. Insoluble components were filtered.

Next, a lithium nonafluoro-n-butanesulfonate aqueous solution comprising 45.9 g of lithium nonafluoro-n-butanesulfonate dissolved in 300 ml of ion-exchanged water and 200 ml of ethyl acetate were added to the resulting filtrate and was stirred at 25° C. for 5 hours. This mixture was transferred to a separatory funnel, shaken, and allowed to stand still. The water layer was removed. 500 ml of distilled water was added and the mixture was shaken again and allowed to stand still. The water layer was removed. The resulting ethyl acetate solution was dried with anhydrous magnesium sulfate and filtered. After evaporating ethyl acetate from the dried solution, the residual liquid was dried under reduced pressure and purified by reprecipitation using N-hexane-methylene chloride. The liquid was further purified by reprecipitation using methanol-water. The obtained compound was dried under vacuum to obtain 36.5 g of 1-[4-(cyclohexanesulfanyl)naphthalene-1-yl]tetrahydrothiophenium nonafluoro-n-butane sulfonate.

30 g of the resulting 1-[4-(cyclohexanesulfanyl)naphthalene-1-yl]tetrahydrothiophenium nonafluoro-n-butane sulfonate was dissolved in 150 ml of methanol in a reaction flask. 30 g of 30 wt % hydrogen peroxide solution and 1.8 g of sodium tangstate dihydride were added. The mixture was stirred for 30 minutes at room temperature. The resulting methanol solution was condensed under reduced pressure and the residue was dissolved in 500 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residue was recrystallized using n-hexane-methylene chloride. The obtained crystal was dried under vacuum to obtain 25 g of 1-[4-(cyclohexanesulfanyl)naphthalen-1-yl]tetrahydrothiophenium nonafluoro-n-butane sulfonate. This compound is indicated as "acid generator (A-16)".

Synthesis Example 17

26.7 g of 4-fluorophenyl diphenylsulfonium trifluoromethanesulfonate was dissolved in 200 g of dichloromethane in a reaction flask, in which the atmosphere was replaced with nitrogen. 200 g of 10 wt % sodium hydroxide aqueous solution, 5.8 g of tetra-n-butylammonium bromide, and 6.71 g of methanethiol were added. The mixture was stirred for 30 minutes at room temperature and transferred to a separatory funnel, shaken, and allowed to stand still. The water layer was removed. After the addition of 300 ml of distilled water, the mixture was shaken again and allowed to stand still. The water layer was removed. The resulting dichloromethane solution was dried using anhydrous magnesium sulfate and filtered. After evaporating dichloromethane from the dried solution, the residual liquid was dried under reduced pressure to obtain 19.2 g of 4-methylthiophenyl diphenylsulfonium trifluoromethane sulfonate.

19.2 g of the resulting 4-methanethiophenyl diphenylsulfonium trifluoromethane sulfonate was dissolved in 100 g of methanol in a reaction flask. The mixture was fed into an ion-exchange chromatography (an ion-exchange resin: Shephadex R-QAE A25, packing amount: 60 g, manufactured by Aldrich Corporation) to replace trifluoromethanesulfonate anions with chlorine ions. After evaporating methanol using an evaporator, the resulting residue was dissolved in 100 g of dichloromethane. 15 g of 30 wt % 2-(bicyclo[2.2.1]heptan-2-yl)-1,1,2,2-tetrafluoroethane sodium sulfonate aqueous solution was added. The mixture was stirred for one hour at room temperature and transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 20.1 g of 4-cyclohexylthiophenyl diphenylsulfonium 2-(bicyclo[2.2.1]heptan-2-yl)-1,1,2,2-tetrafluoroethanesulfonate. 20.1 g of the resulting 4-methanethiophenyl diphenylsulfonium 2-(bicyclo[2.2.1]heptan-2-yl)-1,1,2,2-tetrafluoroethanesulfonate was dissolved in 300 ml of methanol in a reaction flask. 18 g of 30 wt % hydrogen peroxide solution and 10.5 g of sodium tangstate dihydride were added. The mixture was stirred for 30 minutes at room temperature. The resulting methanol solution was condensed under reduced pressure and the residue was dissolved in 300 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residual liquid was dried under reduced pressure to obtain 15.5 g of 4-methanesulfonylphenyl diphenylsulfonium 2-(bicyclo[2.2.1]heptan-2-yl)-1,1,2,2-tetrafluoroethanesulfonate. This compound is indicated as "acid generator (A-17)".

Synthesis Example 18

A stirring rod was placed in a fully dried eggplant type flask (100 ml). The flask was charged with 18.1 g of 1-cyclohexylthionaphthalene and 39.7 g of diphosphorus pentaoxide-methanesulfonic acid. The mixture was stirred at 0° C. while cooling in an ice bath. After the addition of 8.9 g of tetramethylene sulfoxide dropwise to the mixture over five minutes or more, the mixture was stirred at 0° C. for 10 minutes. After removing the flask from the ice bath, the mixture was stirred at 45° C. for four hours. The reaction mixture was cooled to 0° C. in an ice bath. 450 ml of ion-exchanged water and 25 wt % aqueous ammonia were added dropwise to adjust the pH of the reaction mixture to 7. After removing the flask from the ice bath, the mixture was stirred at 25° C. for one hour. Insoluble components were filtered.

Next, 45 g of 30 wt % 2-(bicyclo[2.2.1]heptan-2-yl)-1,1,2,2-tetrafluoroethane sodium sulfonate aqueous solution and 200 ml of ethyl acetate were added to the resulting filtrate and the mixture was stirred at 25° C. for five hours. This solution was transferred to a separatory funnel, shaken, and allowed to stand still. The water layer was removed. 500 ml of distilled water was added and the mixture was shaken again and allowed to stand still. The water layer was removed. The resulting ethyl acetate solution was dried with anhydrous magnesium sulfate and filtered. After evaporating ethyl acetate from the dried solution, the residual liquid was dried under reduced pressure and purified by reprecipitation using n-hexane-methylene chloride. The liquid was further purified by reprecipitation using methanol-water. The obtained compound was dried under vacuum to obtain 33.5 g of 1-[4-(cyclohexanesulfanyl)naphthalene-1-yl]tetrahydrothiophenium 2-(bicyclo[2.2.1]heptan-2-yl)-1,1,2,2-tetrafluoroethane sulfonate.

30 g of the resulting 1-[4-(cyclohexanesulfanyl)naphthalene-1-yl]tetrahydrothiophenium nonafluoro-n-butane sulfonate was dissolved in 150 ml of methanol in a reaction flask. 30 g of 30 wt % hydrogen peroxide solution and 1.8 g of sodium tangstate dihydride were added. The mixture was stirred for 30 minutes at room temperature. The resulting methanol solution was condensed under reduced pressure and the residue was dissolved in 500 g of dichloromethane. The mixture was transferred to a separatory funnel, shaken, and allowed to stand still. The water layer was removed. 100 ml of distilled water was added and the mixture was shaken again and allowed to stand still. The water layer was removed. The resulting dichloromethane solution was dried with anhydrous magnesium sulfate and filtered. After evaporating dichloromethane from the dried solution, the residue was recrystallized using n-hexane-methylene chloride and the obtained crystal was dried under vacuum to obtain 22 g of 1-[4-(cyclohexanesulfanyl)naphthalene-1-yl]tetrahydrothiophenium 2-(bicyclo[2.2.1]heptan-2-yl)-1,1,2,2-tetrafluoroethane sulfonate. This compound is indicated as "acid generator (A-18)".

Mass Spectrometry Analysis

Figure 2:
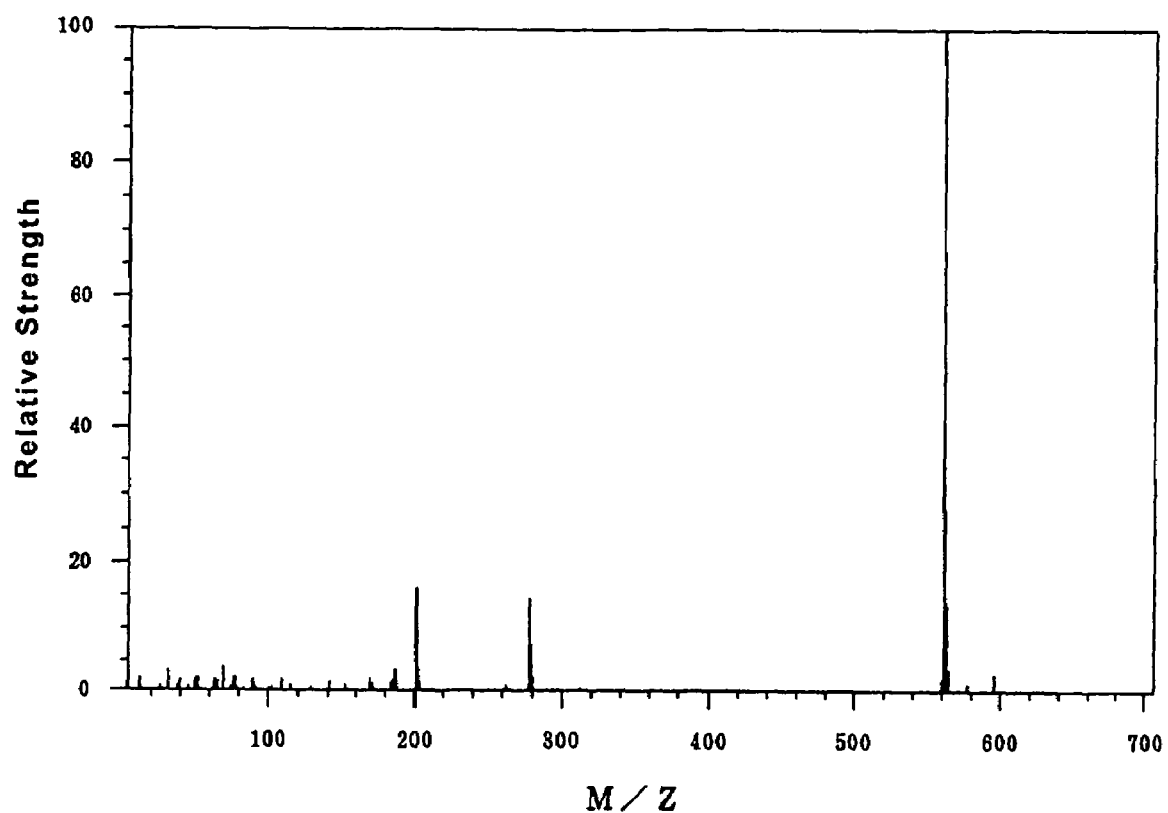
FIG. 2 shows a mass spectrometry spectrum in the cation moiety of the acid generator (A-2).
Figure 3:
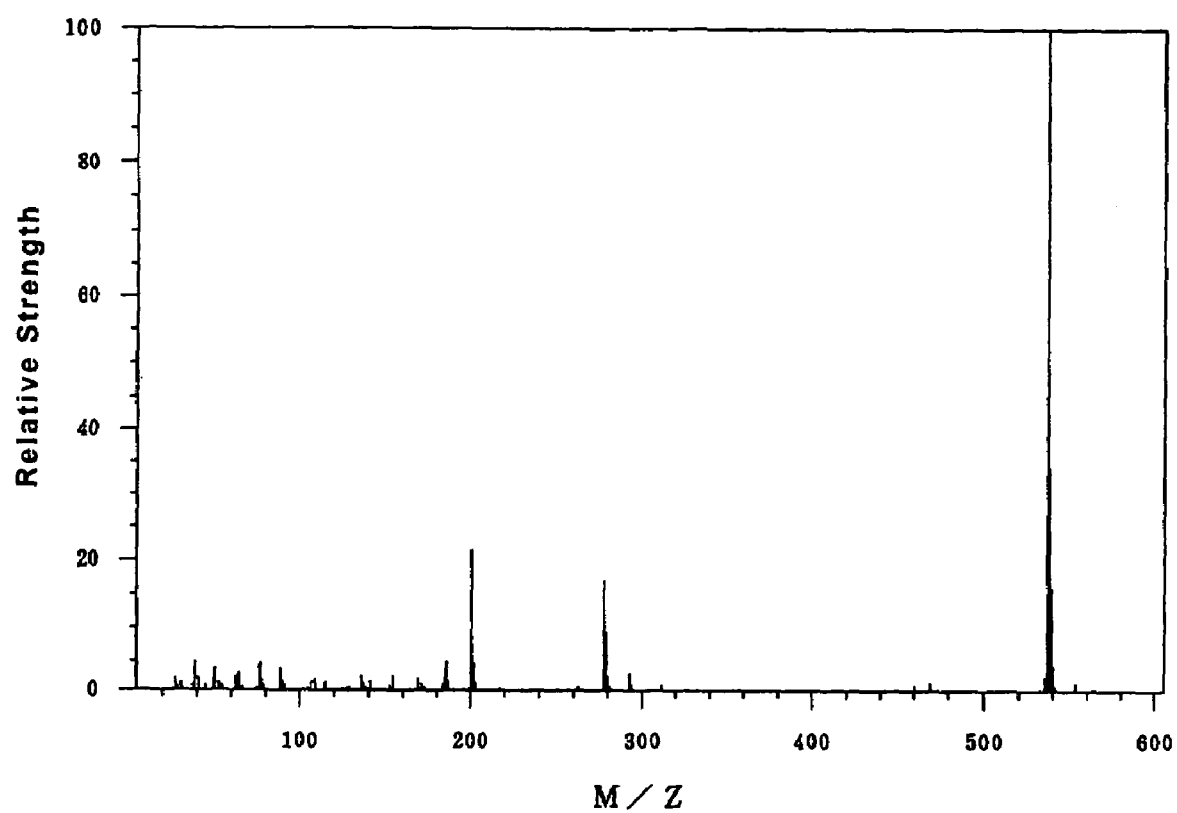
FIG. 3 shows a mass spectrometry spectrum in the cation moiety of the acid generator (A-3).
Figure 4:
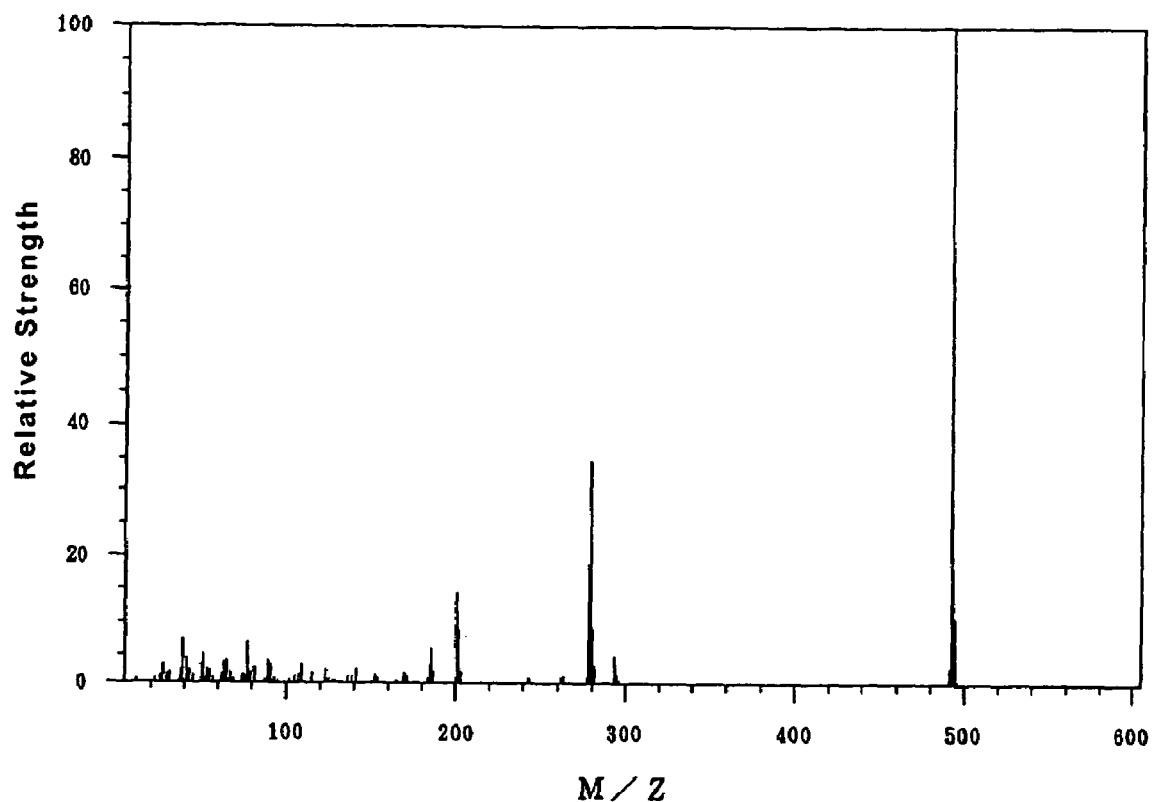
FIG. 4 shows a mass spectrometry spectrum in the cation moiety of the acid generator (A-4).
Figure 5:
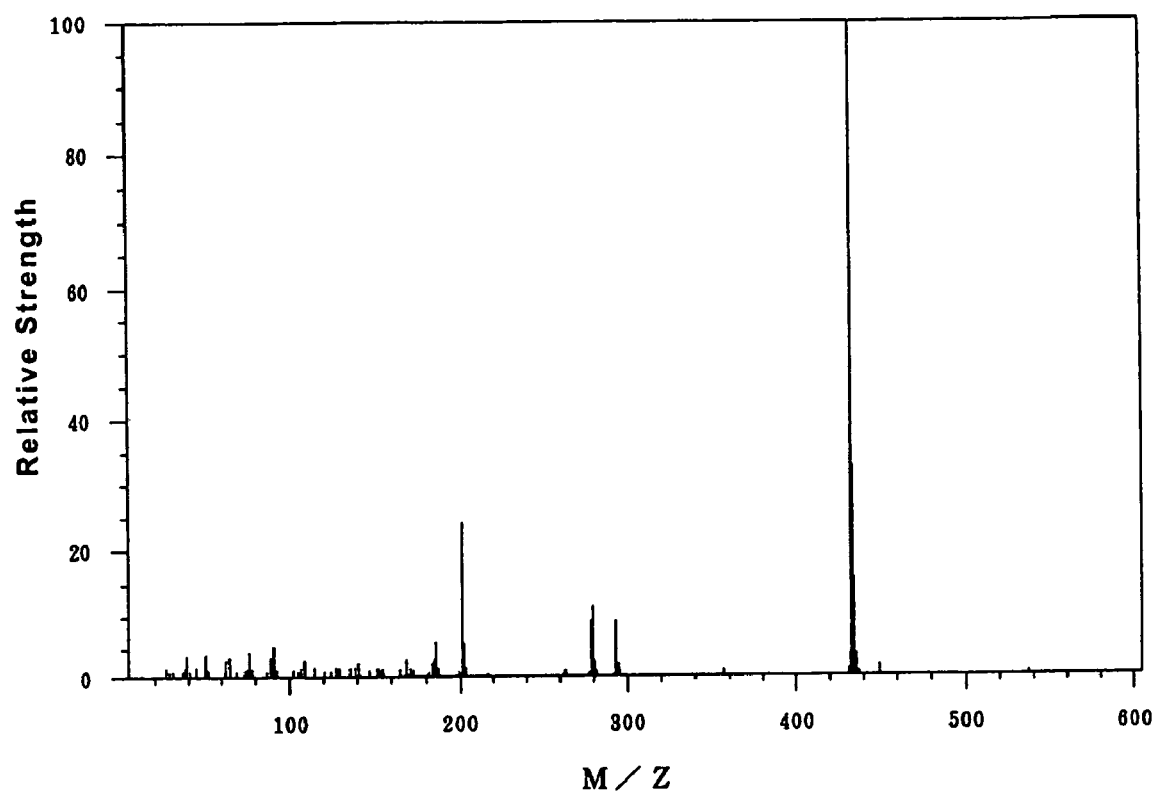
FIG. 5 shows a mass spectrometry spectrum in the cation moiety of the acid generator (A-5).
Figure 6:
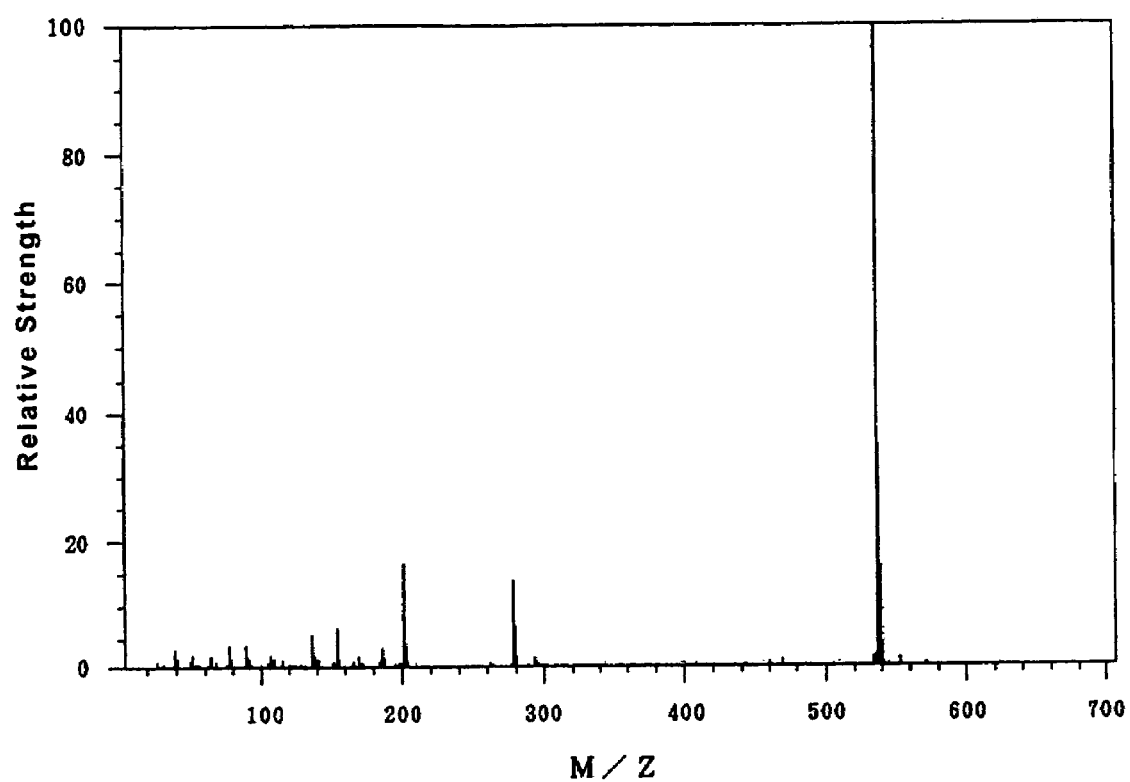
FIG. 6 shows a mass spectrometry spectrum in the cation moiety of the acid generator (A-6).
Figure 7:
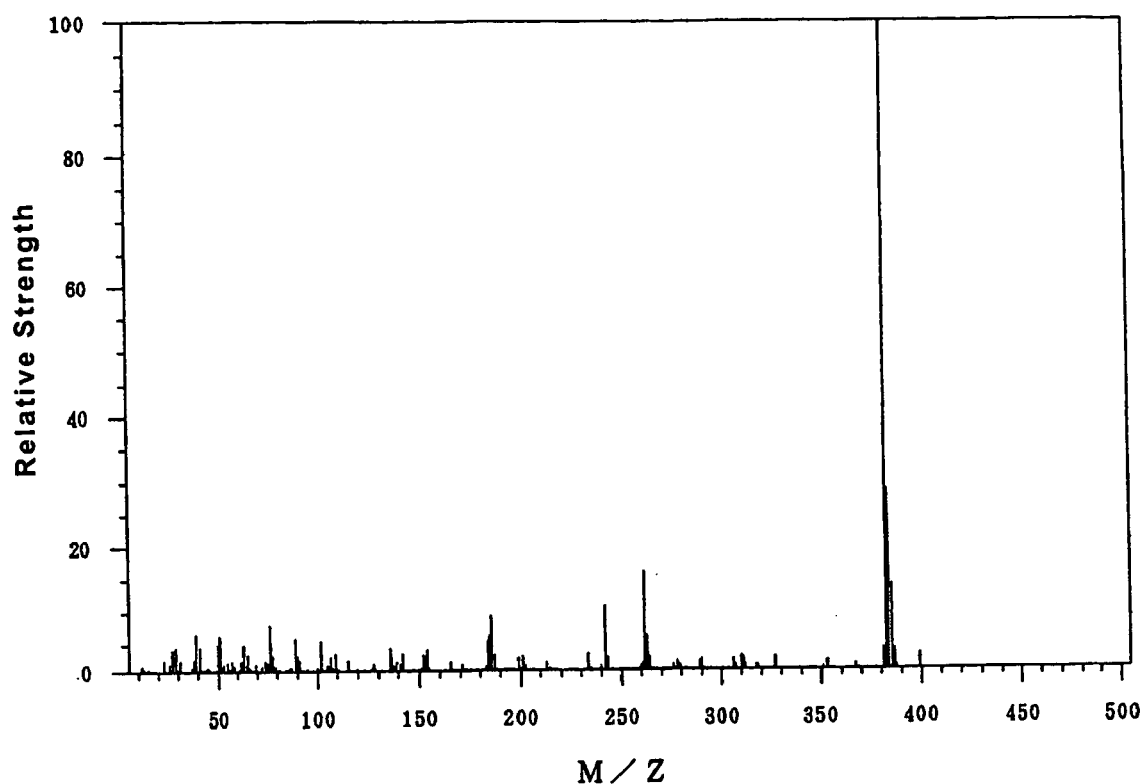
FIG. 7 shows a mass spectrometry spectrum in the cation moiety of the acid generator (A-7).
Figure 8:
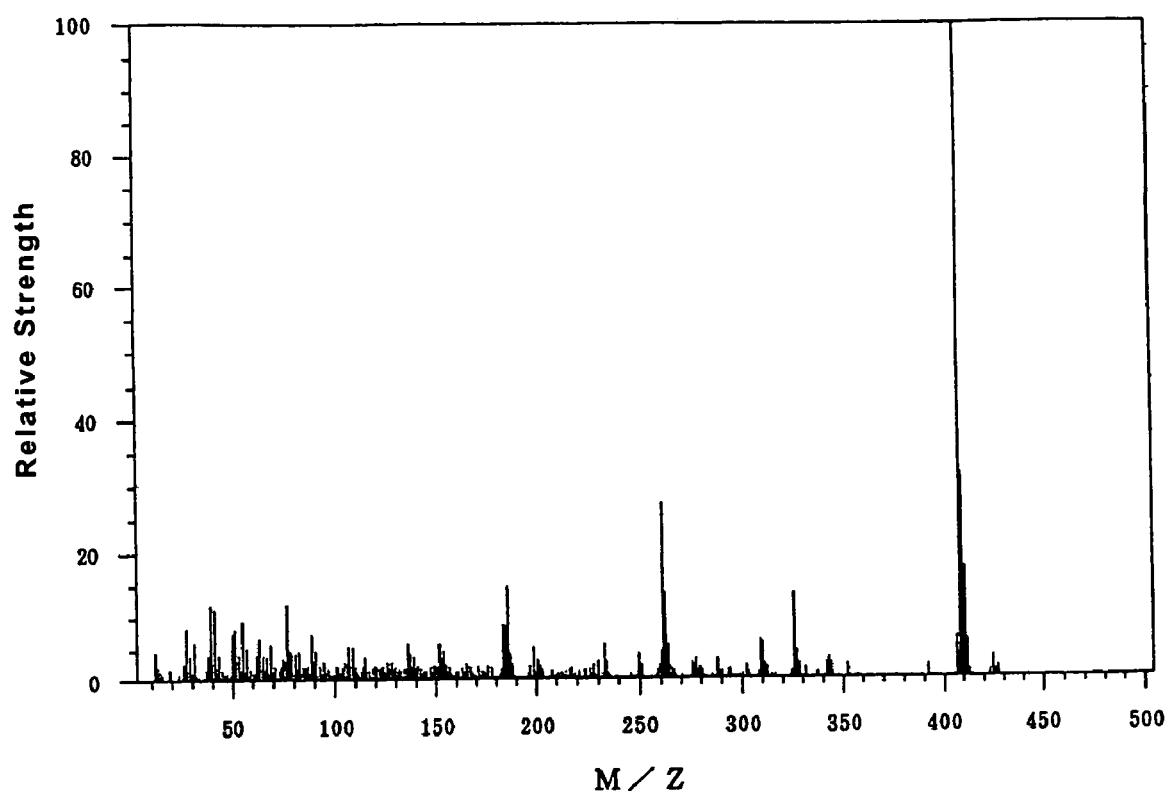
FIG. 8 shows a mass spectrometry spectrum in the cation moiety of the acid generator (A-8).
Figure 9:
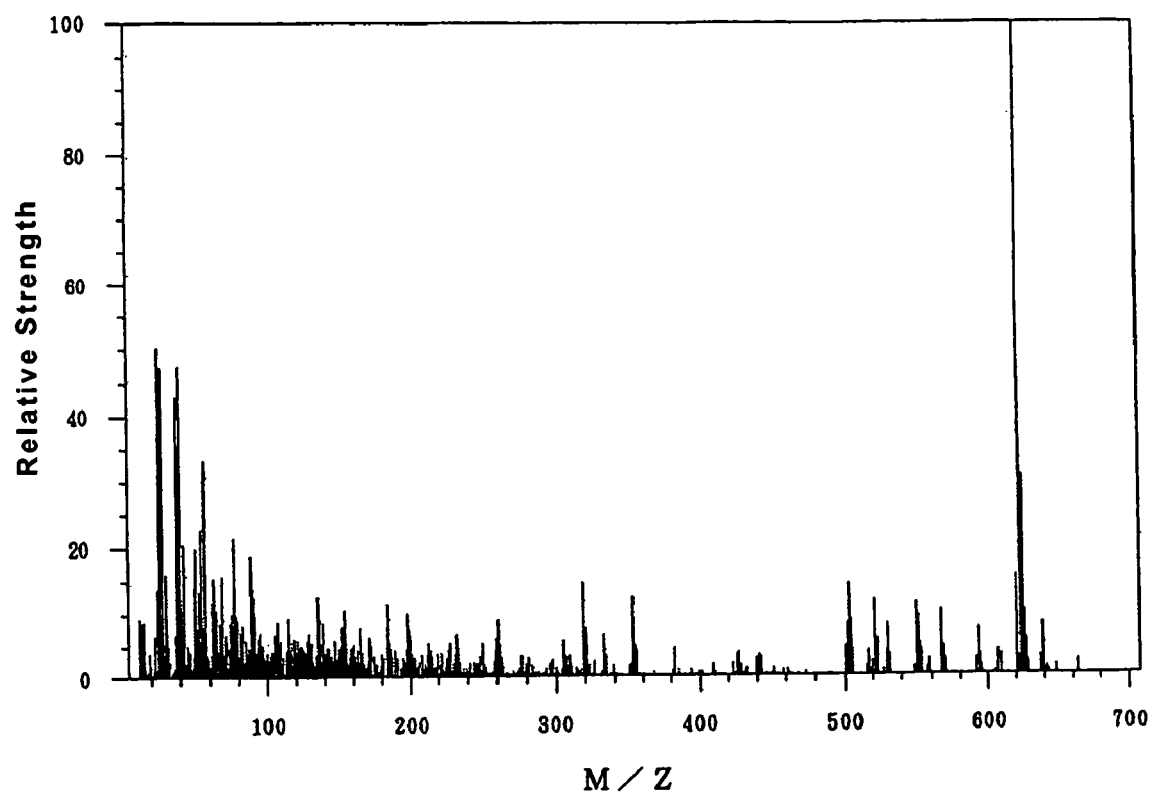
FIG. 9 shows a mass spectrometry spectrum in the cation moiety of the acid generator (A-9).
Figure 10:
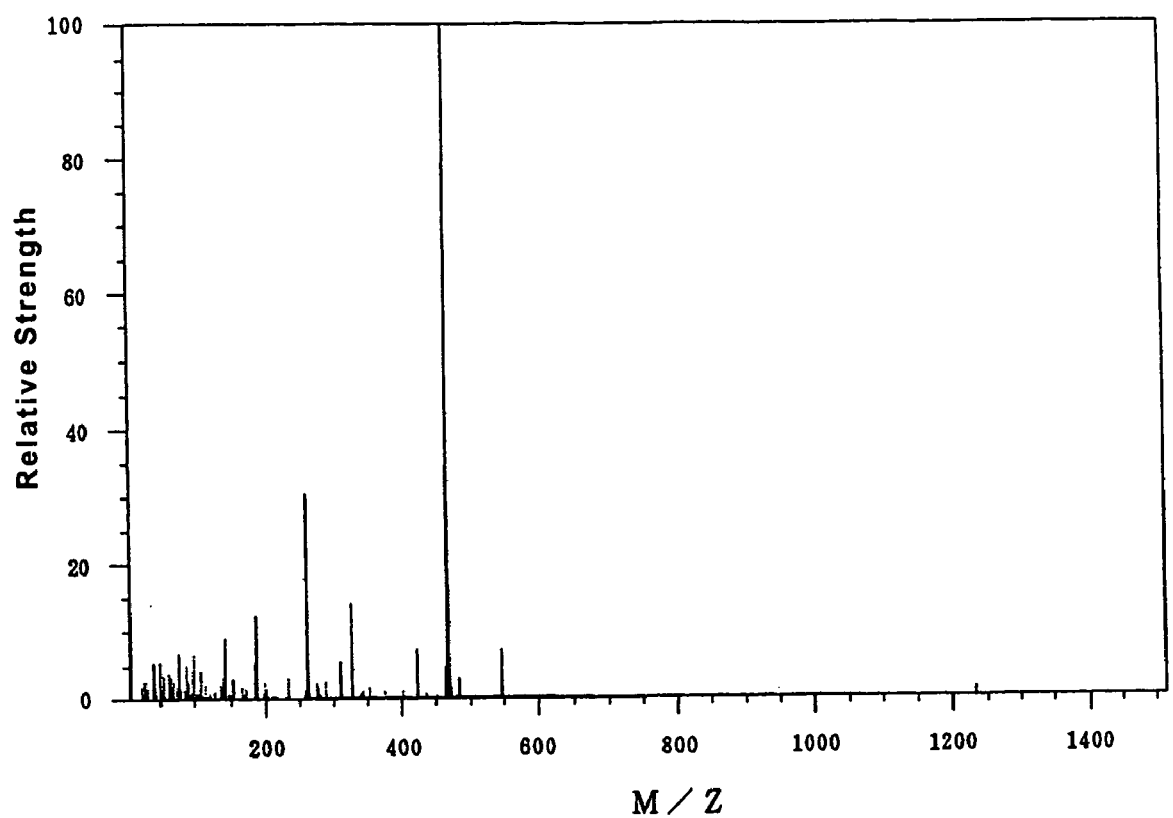
FIG. 10 shows a mass spectrometry spectrum in the cation moiety of the acid generator (A-10).
Figure 11:
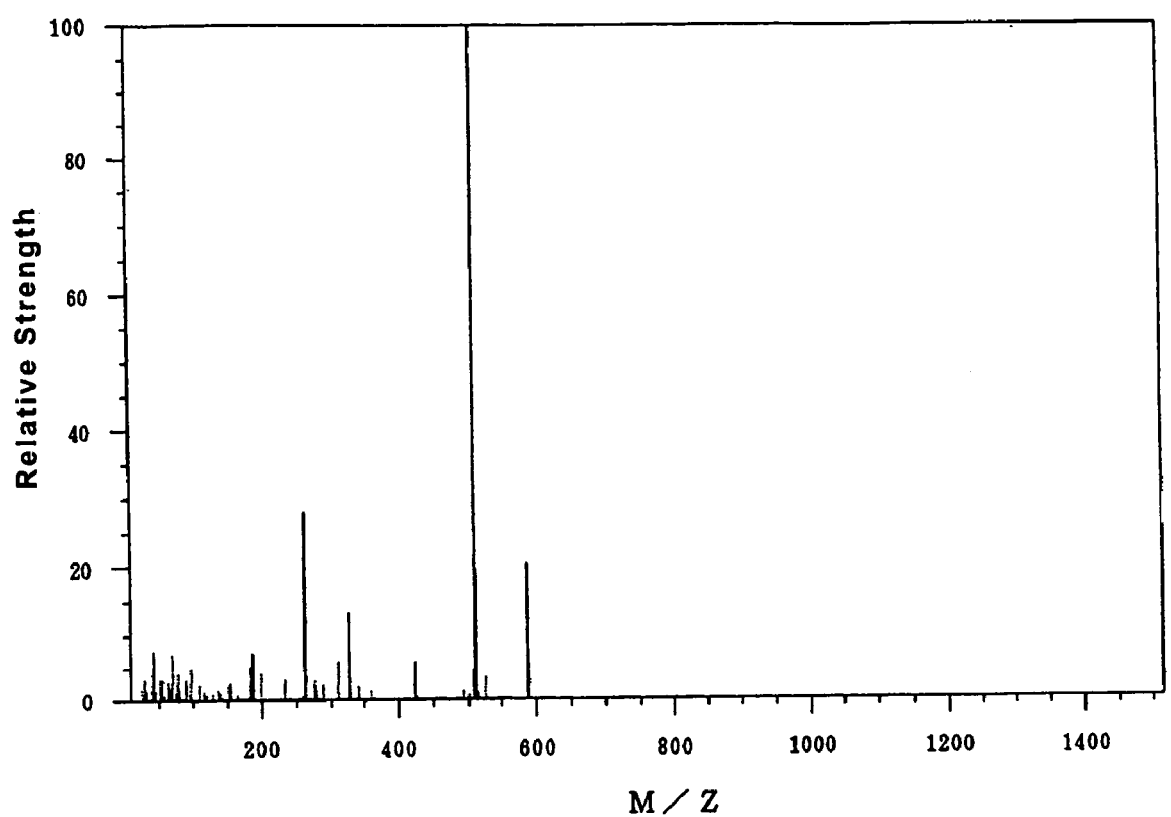
FIG. 11 shows a mass spectrometry spectrum in the cation moiety of the acid generator (A-11).
Figure 12:
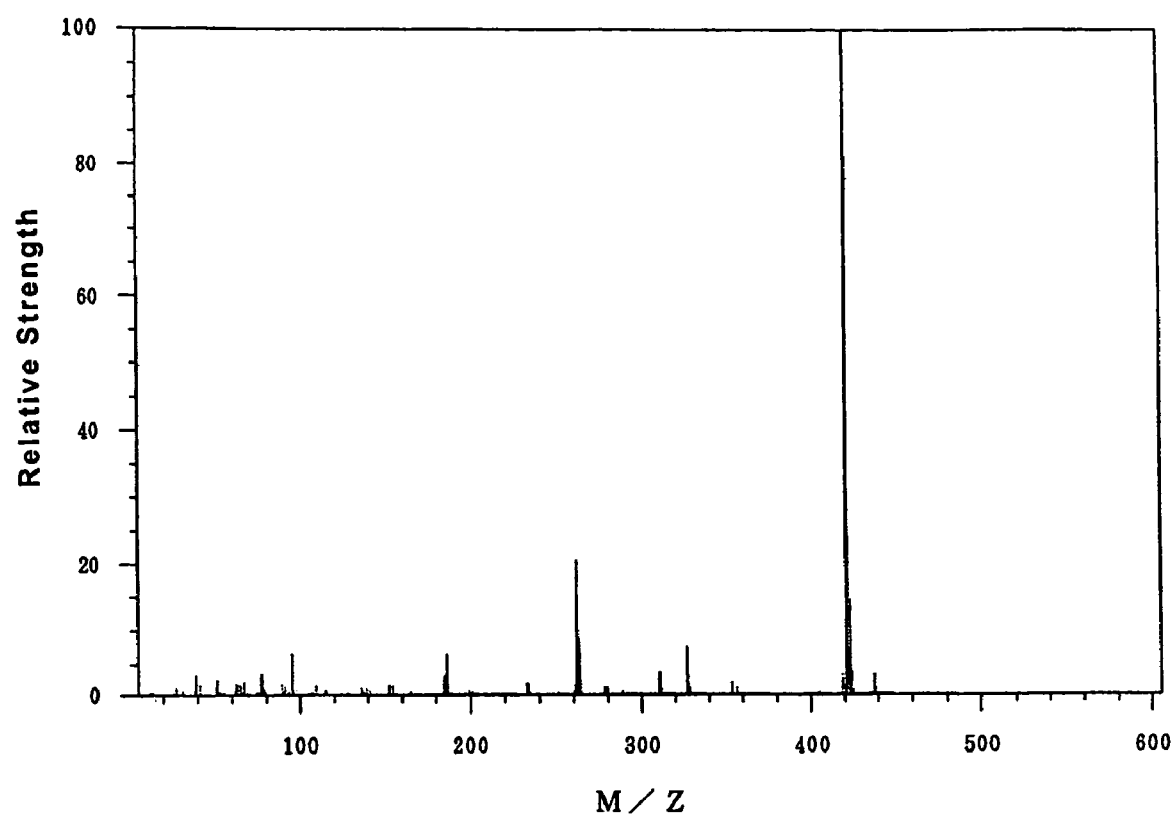
FIG. 12 shows a mass spectrometry spectrum in the cation moiety of the acid generator (A-12).
Figure 13:
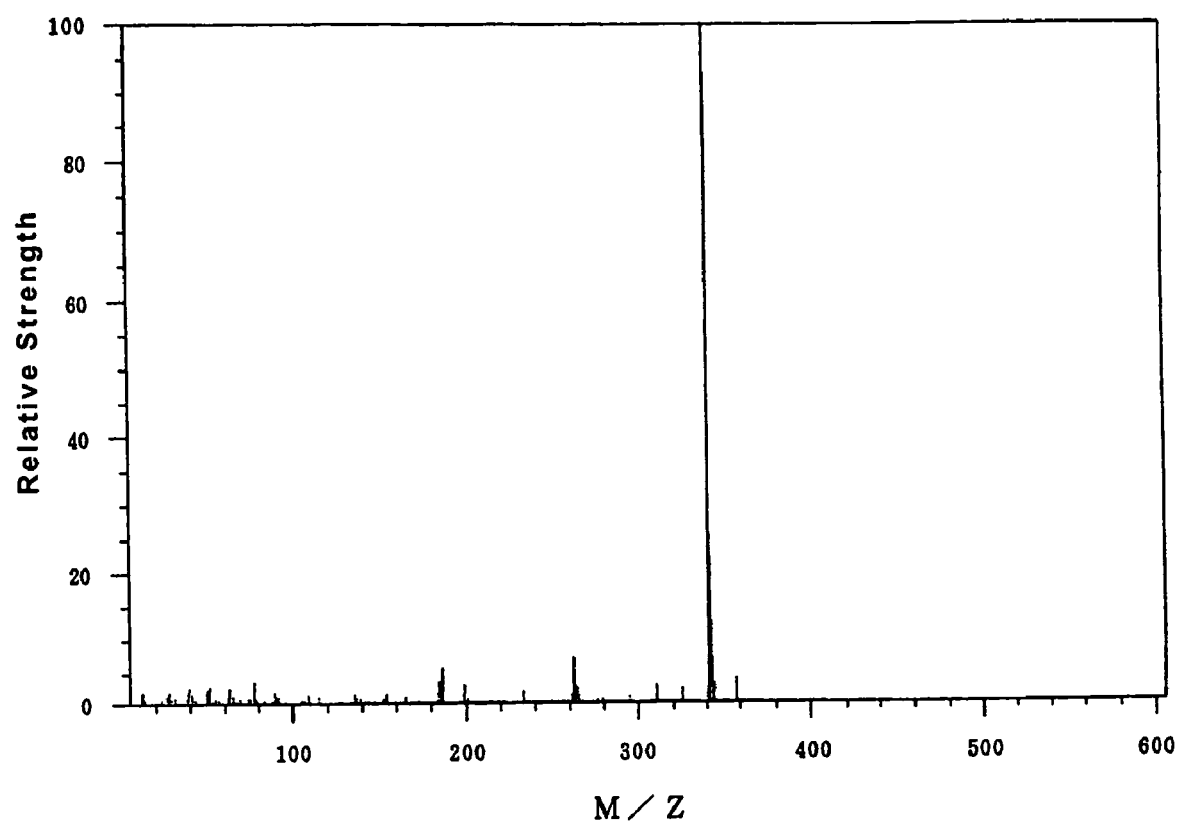
FIG. 13 shows a mass spectrometry spectrum in the cation moiety of the acid generator (A-13).
Figure 14:
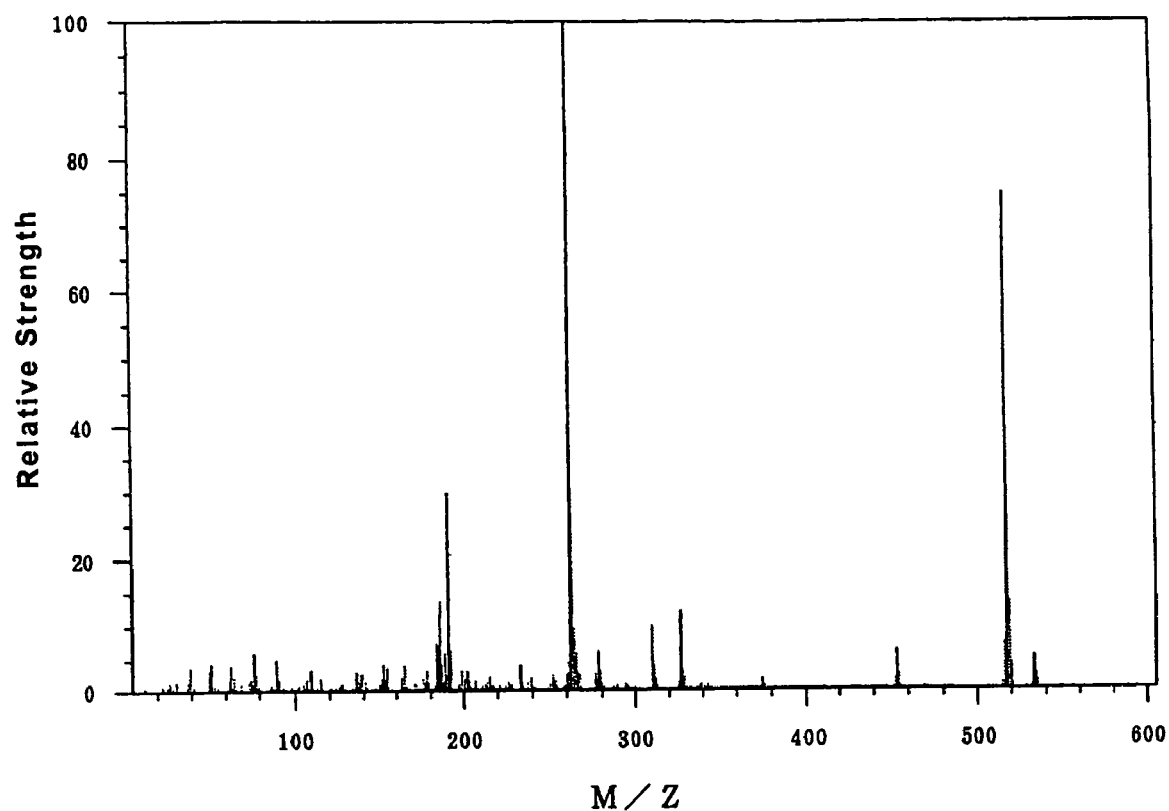
FIG. 14 shows a mass spectrometry spectrum in the cation moiety of the acid generator (A-14).
Figure 15:
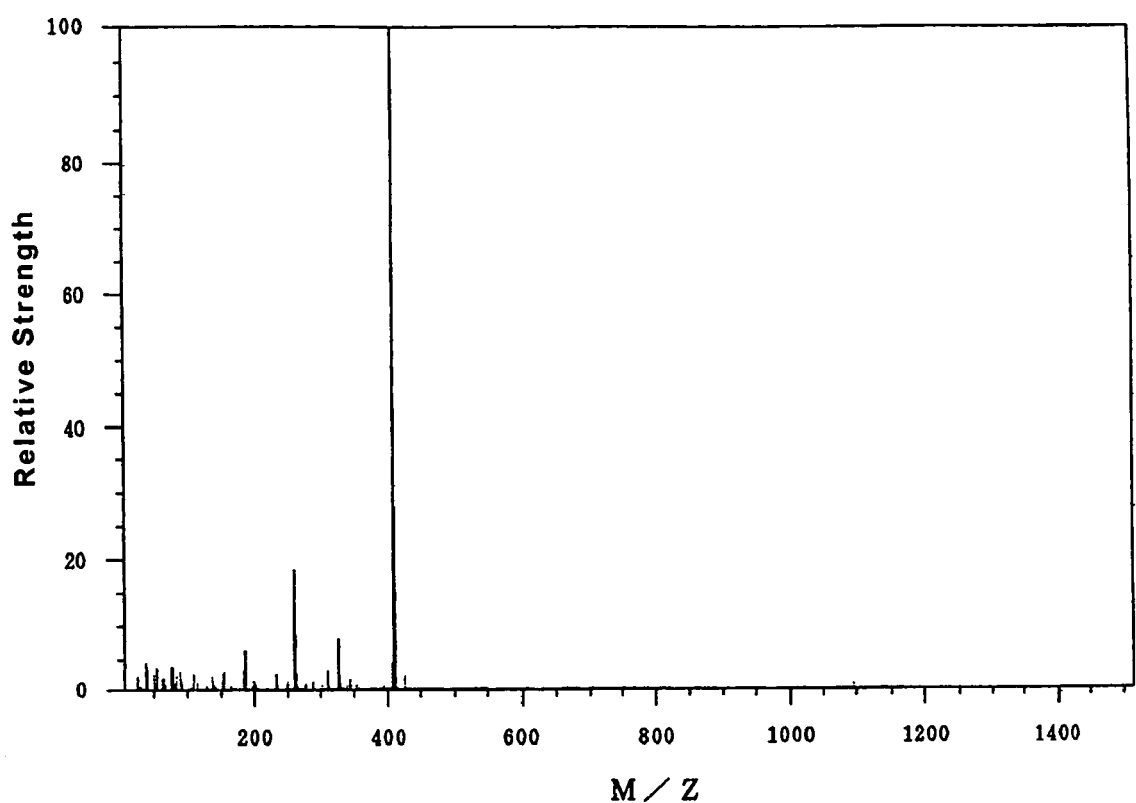
FIG. 15 shows a mass spectrometry spectrum in the cation moiety of the acid generator (A-15).
Figure 16:
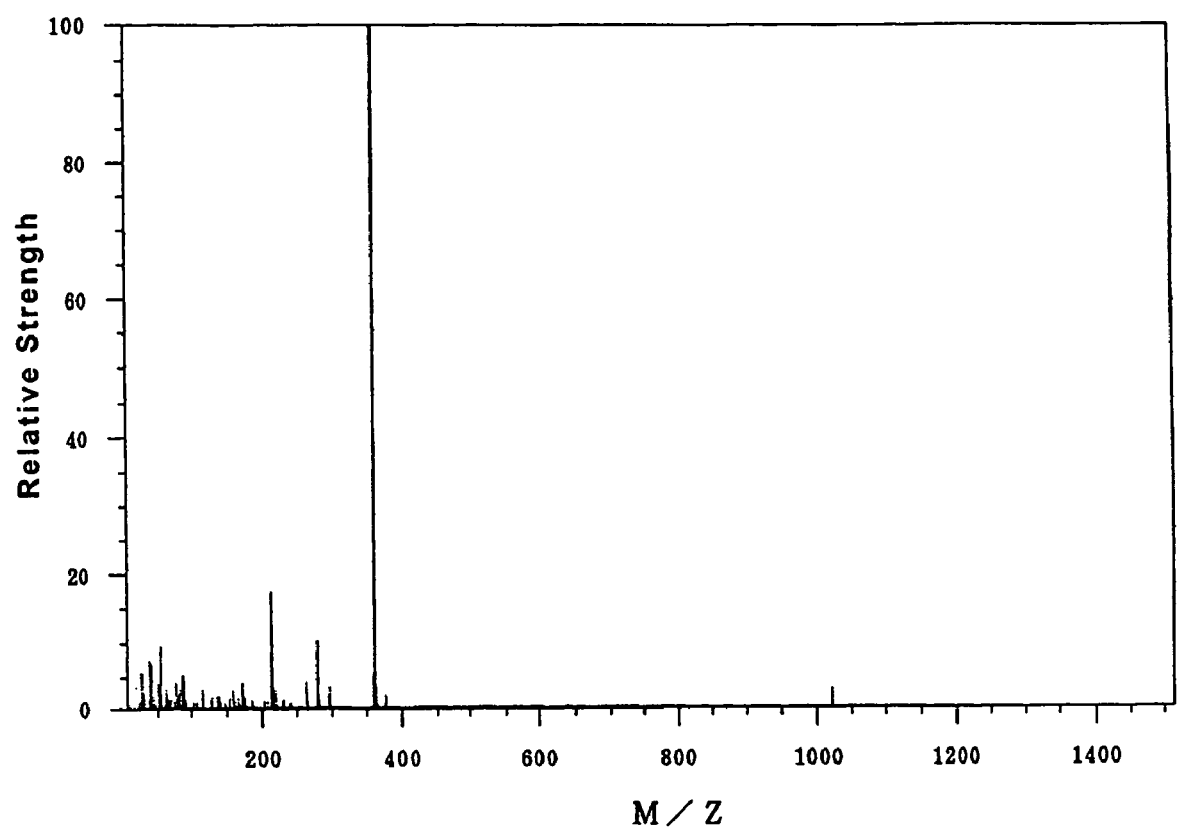
FIG. 16 shows a mass spectrometry spectrum in the cation moiety of the acid generator (A-16).
Figure 17:
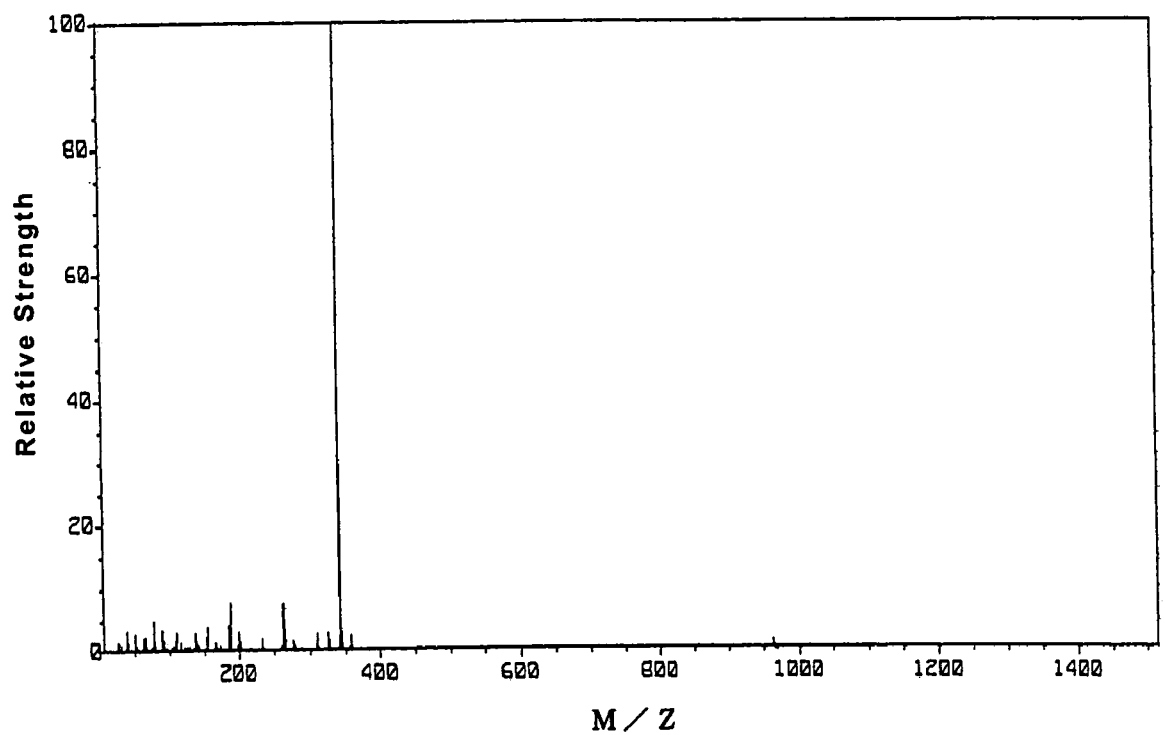
FIG. 17 shows a mass spectrometry spectrum in the cation moiety of the acid generator (A-17).
Figure 18:
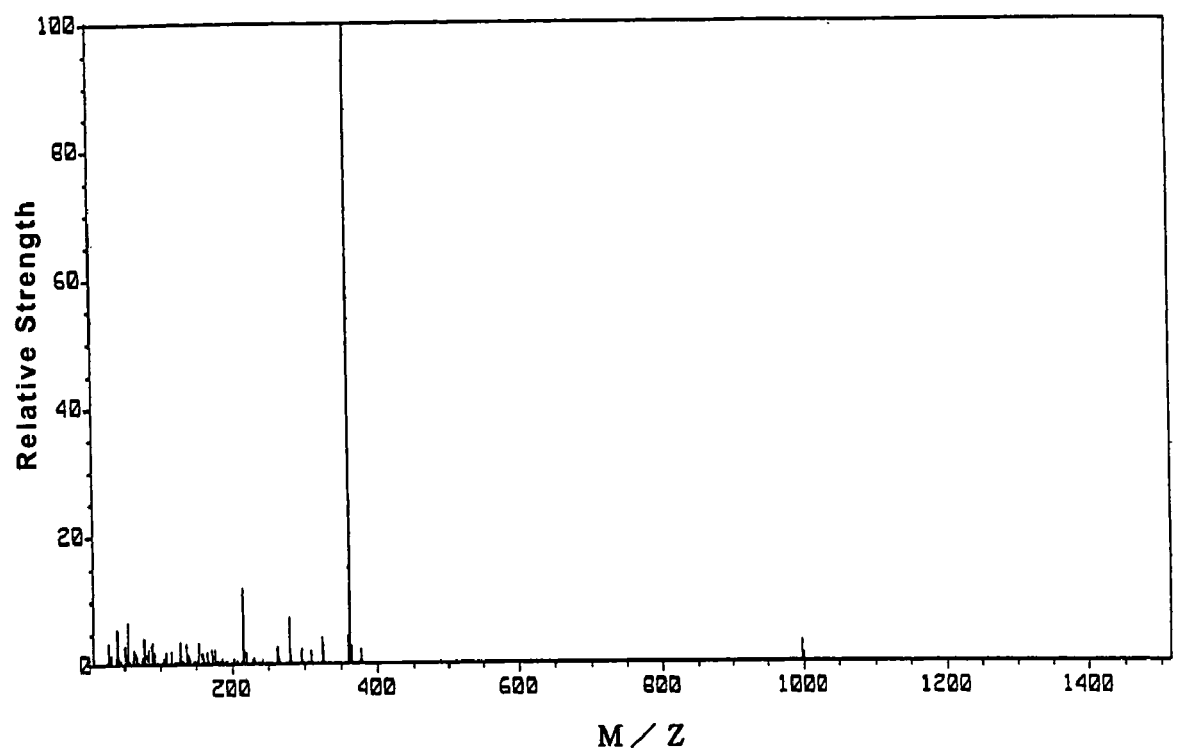
FIG. 18 shows a mass spectrometry spectrum in the cation moiety of the acid generator (A-18).

The acid generators (A-1) to (A-18) were subjected to mass spectrometry analysis using JMS-AX505W mass spectrometer manufactured by JEOL Ltd. The analysis conditions were as follows. The spectra obtained for cationic moieties of the acid generators are shown in FIGS. 1–18.

Emitter current: 5 mA (used gas: Xe)

Acceleration voltage: 3.0 kV

10 N MULTI: 1.3

Ionization method: Fast atom bombardment (FAB) method

Detected ion: cation (+)

Measured mass range: 20–1,500 m/z

Scanning: 30 sec

Resolving power: 1,500

Matrix: 3-Nitrobenzyl alcohol

¹H-NMR Analysis

Figure 19:
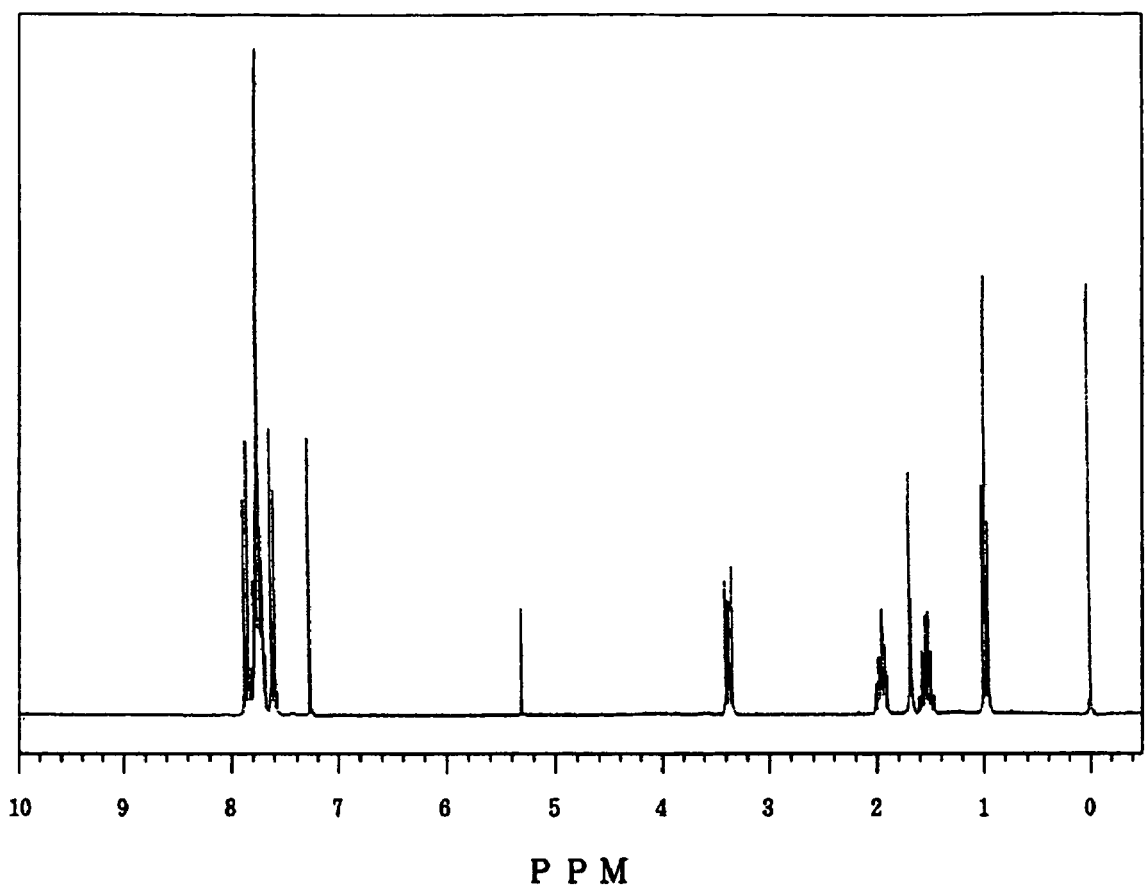
FIG. 19 shows a $^1$H-NMR spectrometry spectrum of the acid generator (A-1).
Figure 20:
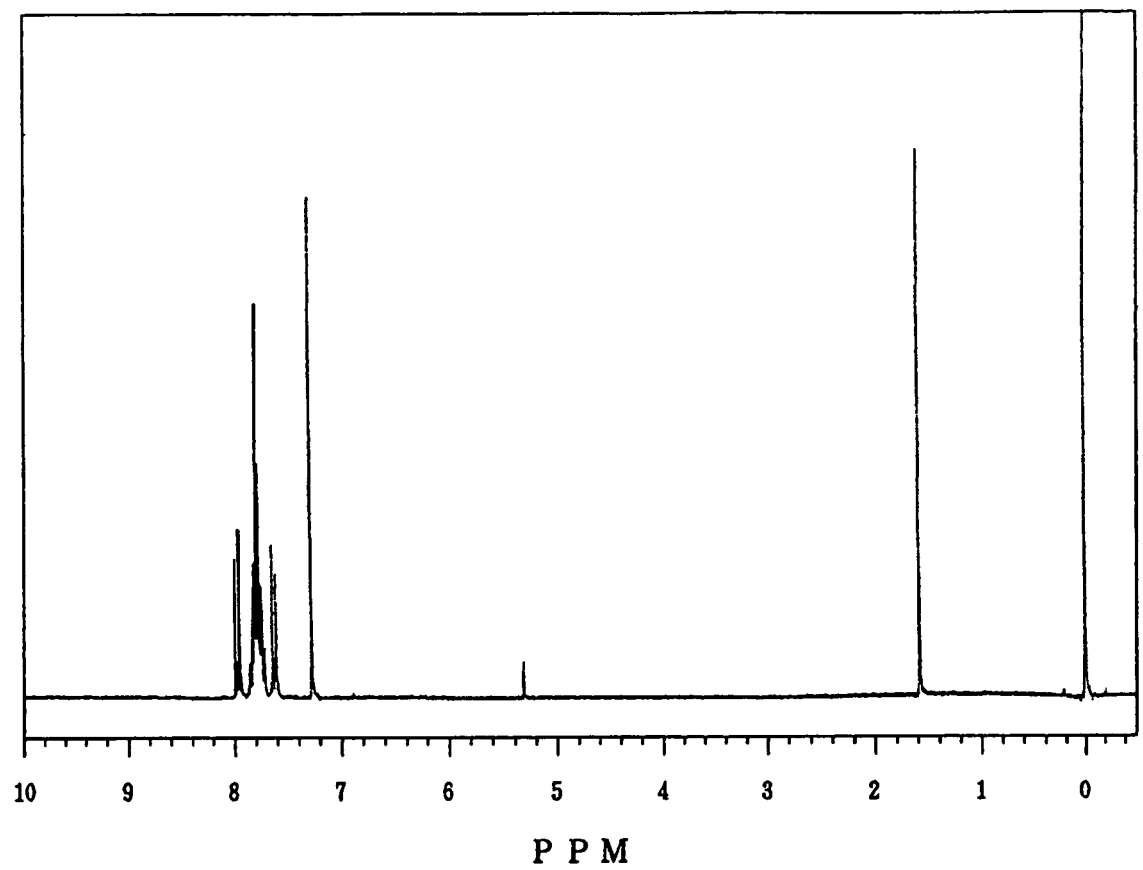
FIG. 20 shows a $^1$H-NMR spectrometry spectrum of the acid generator (A-2).
Figure 21:
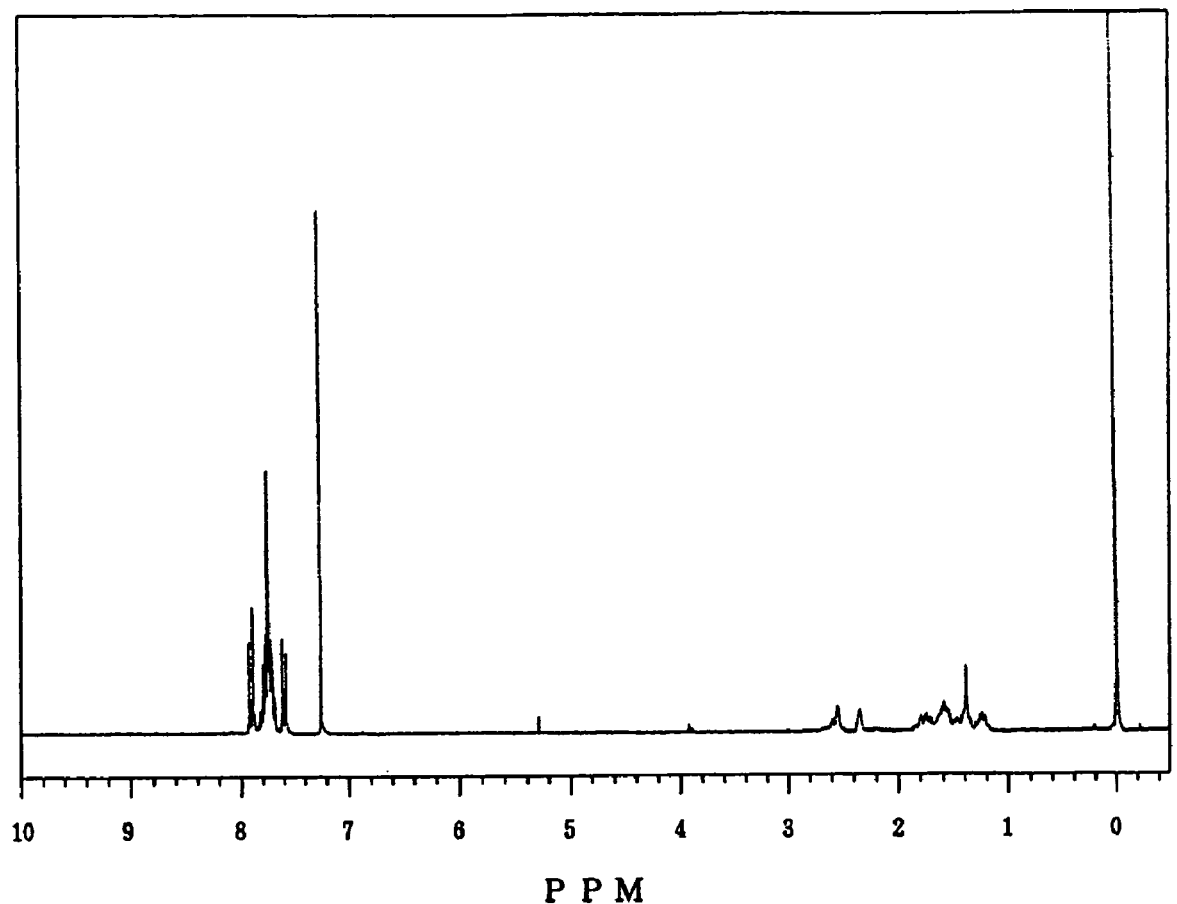
FIG. 21 shows a $^1$H-NMR spectrometry spectrum of the acid generator (A-3).
Figure 22:
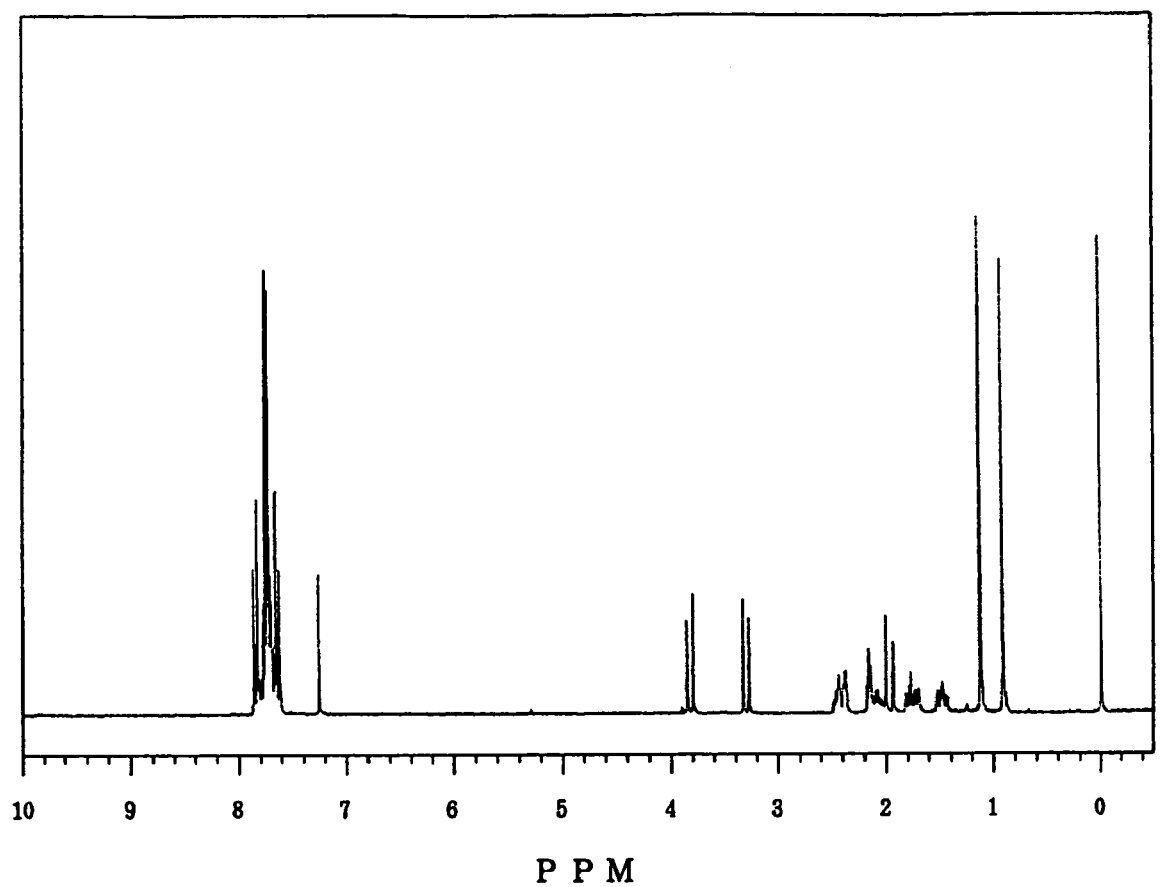
FIG. 22 shows a $^1$H-NMR spectrometry spectrum of the acid generator (A-4).
Figure 23:
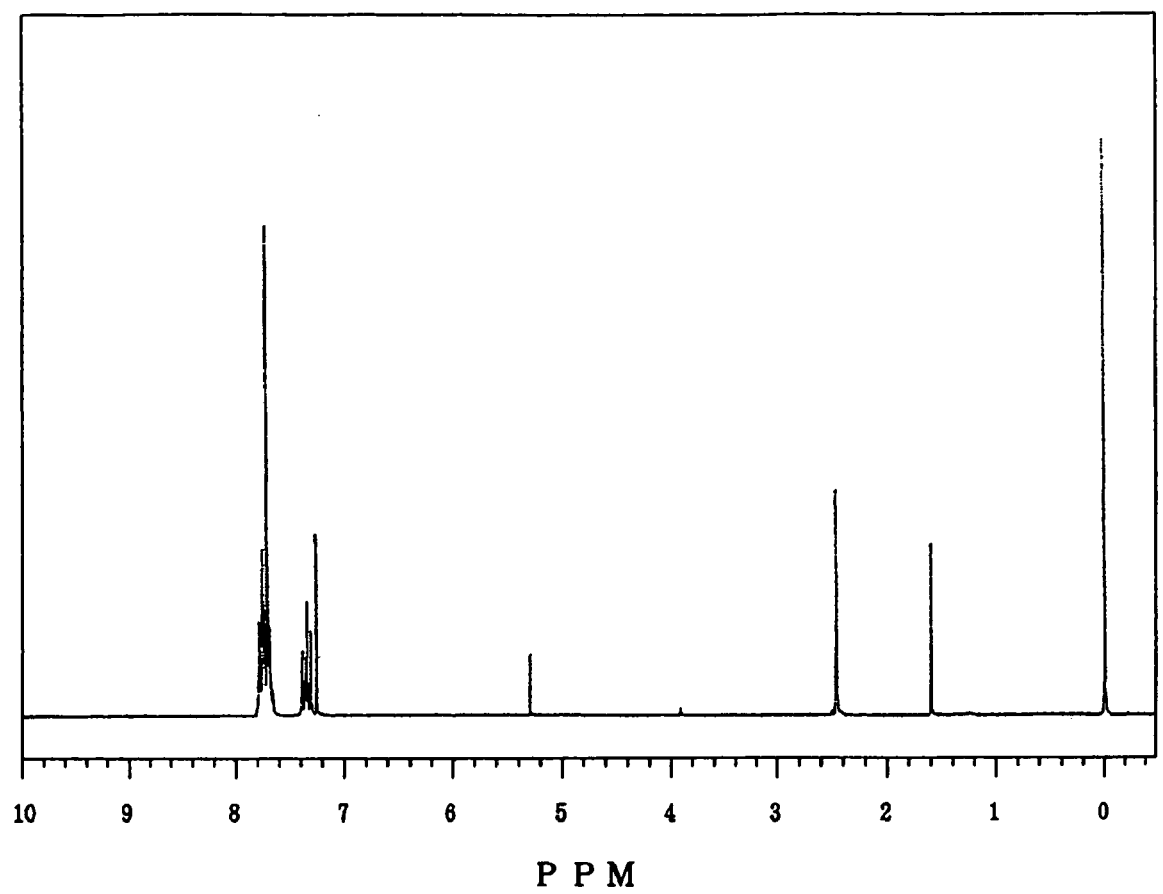
FIG. 23 shows a $^1$H-NMR spectrometry spectrum of the acid generator (A-5).
Figure 24:
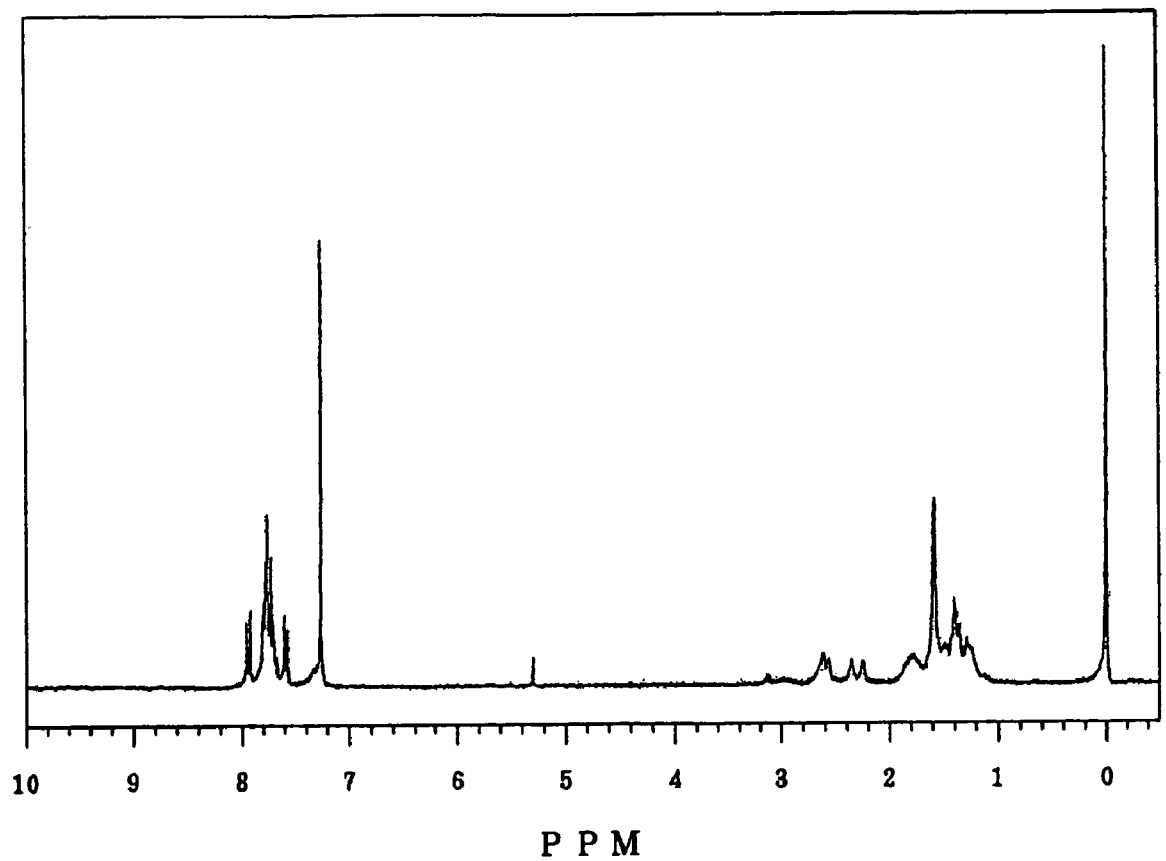
FIG. 24 shows a $^1$H-NMR spectrometry spectrum of the acid generator (A-6).
Figure 25:
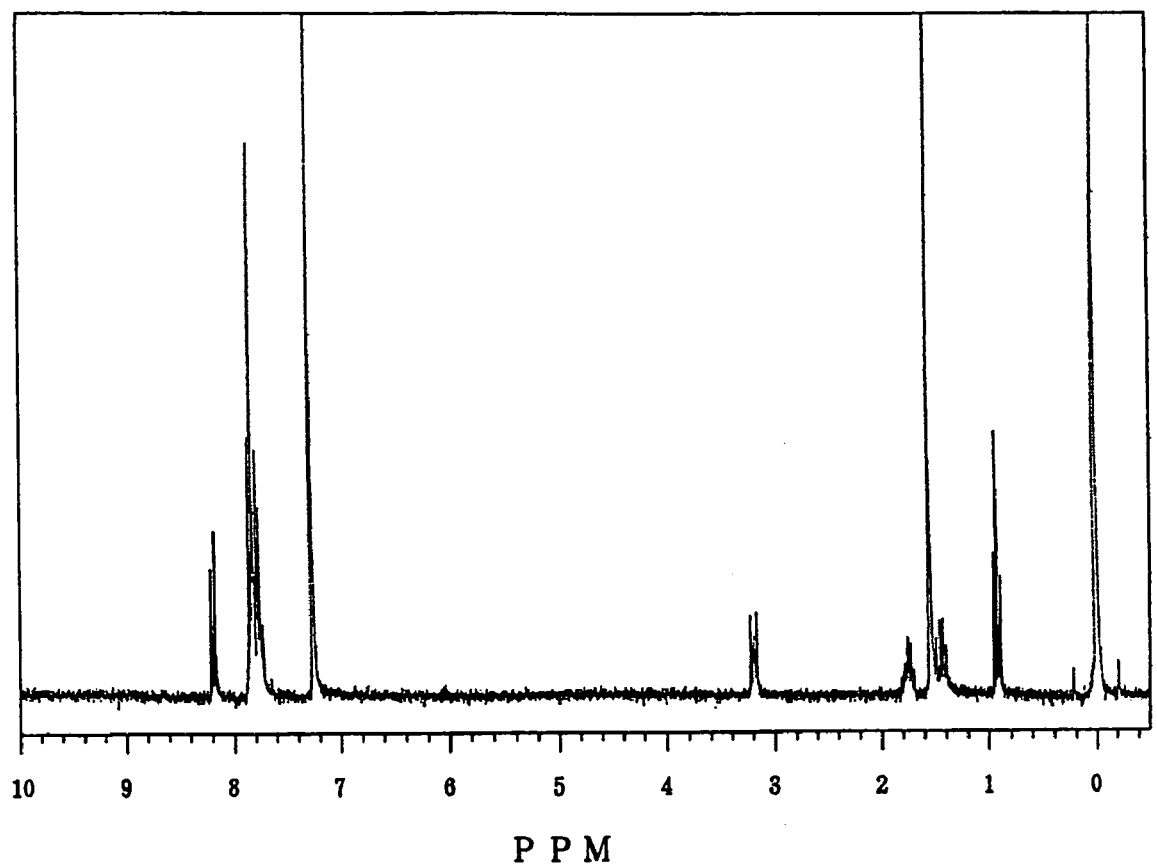
FIG. 25 shows a $^1$H-NMR spectrometry spectrum of the acid generator (A-7).
Figure 26:
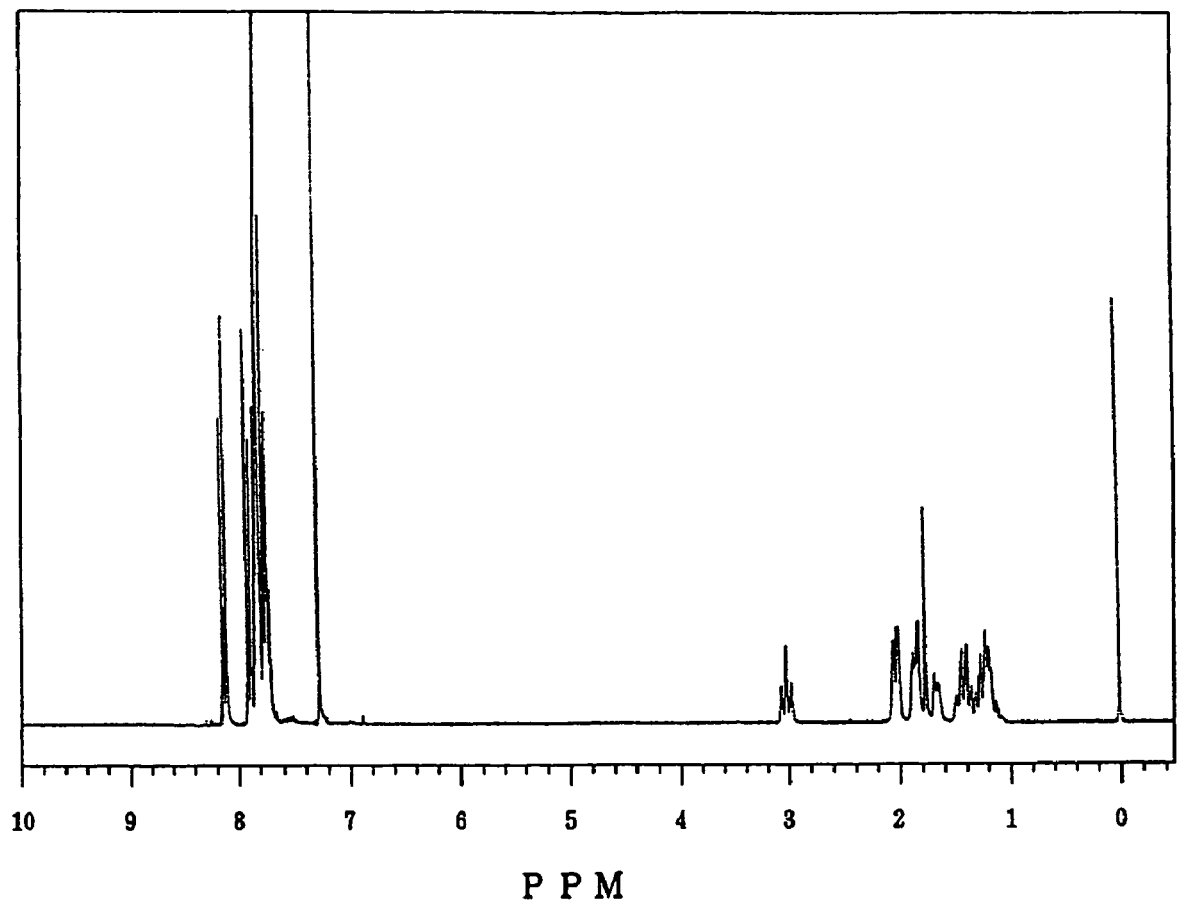
FIG. 26 shows a $^1$H-NMR spectrometry spectrum of the acid generator (A-8).
Figure 27:
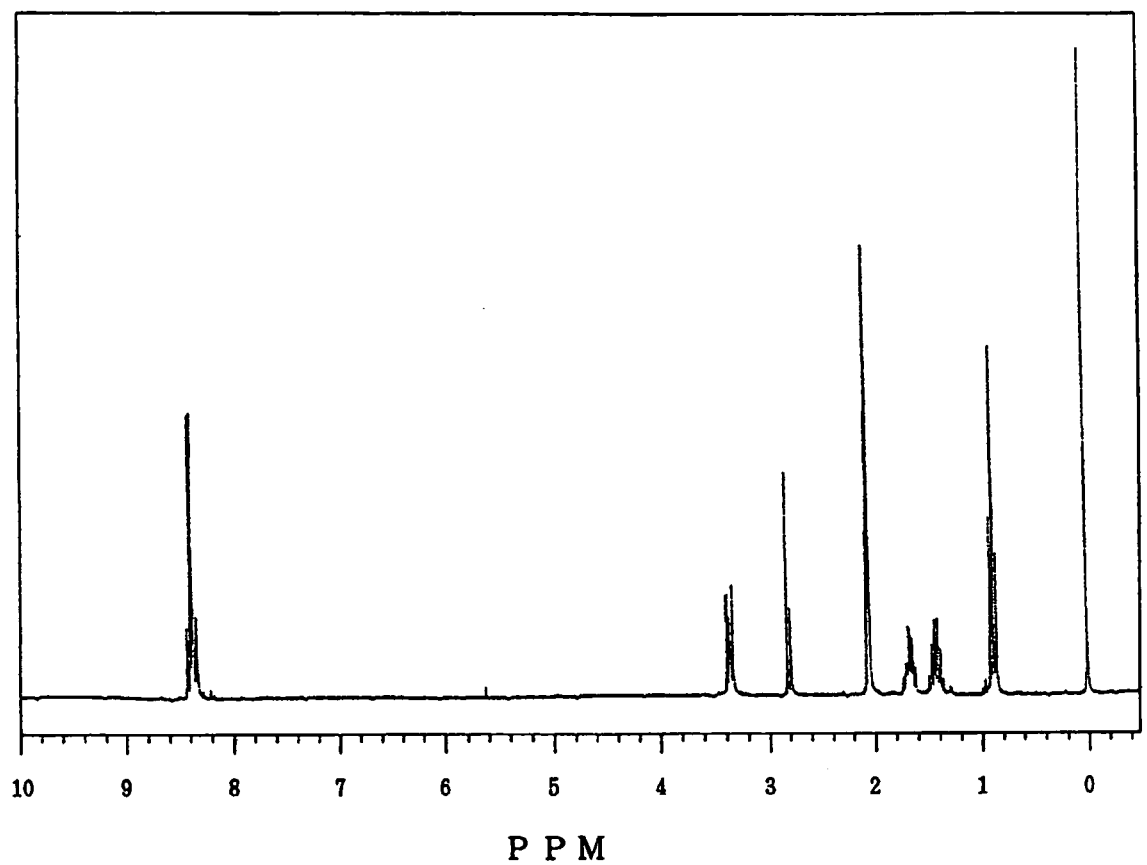
FIG. 27 shows a $^1$H-NMR spectrometry spectrum of the acid generator (A-9).
Figure 28:
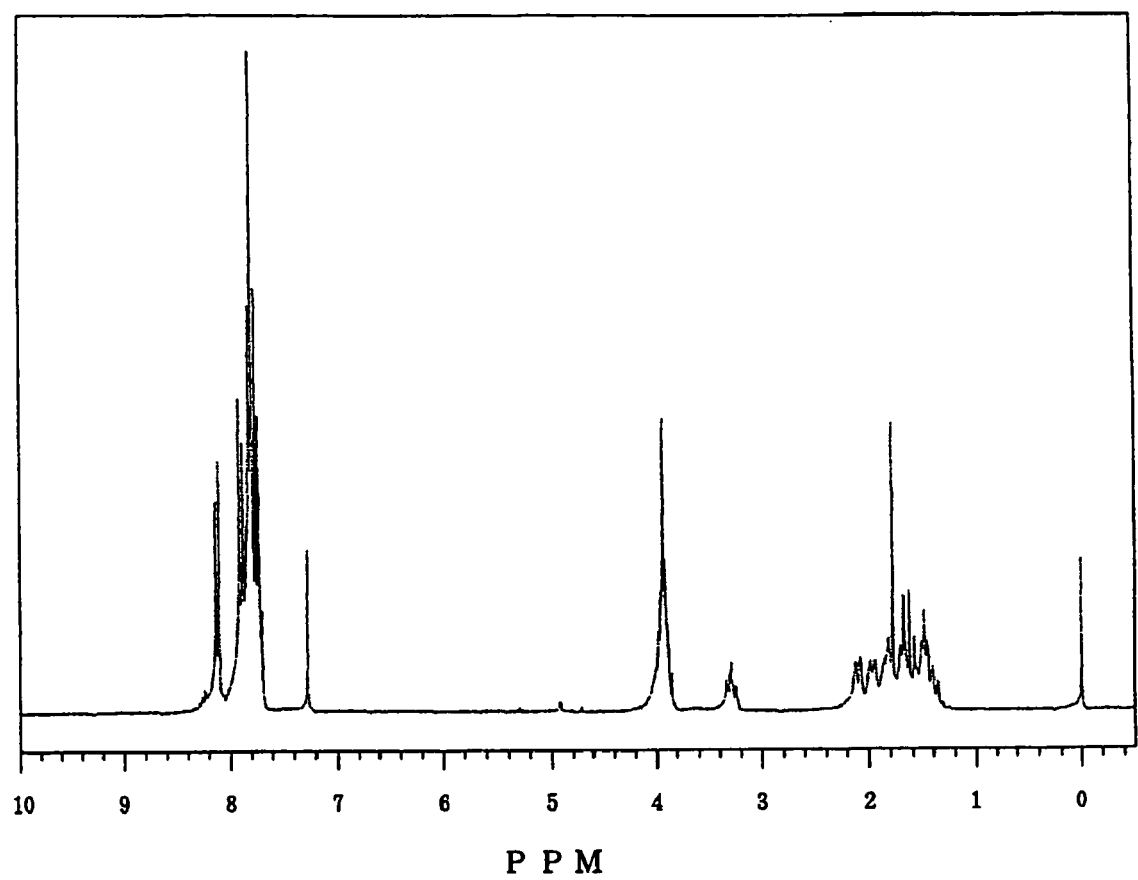
FIG. 28 shows a $^1$H-NMR spectrometry spectrum of the acid generator (A-10).
Figure 29:
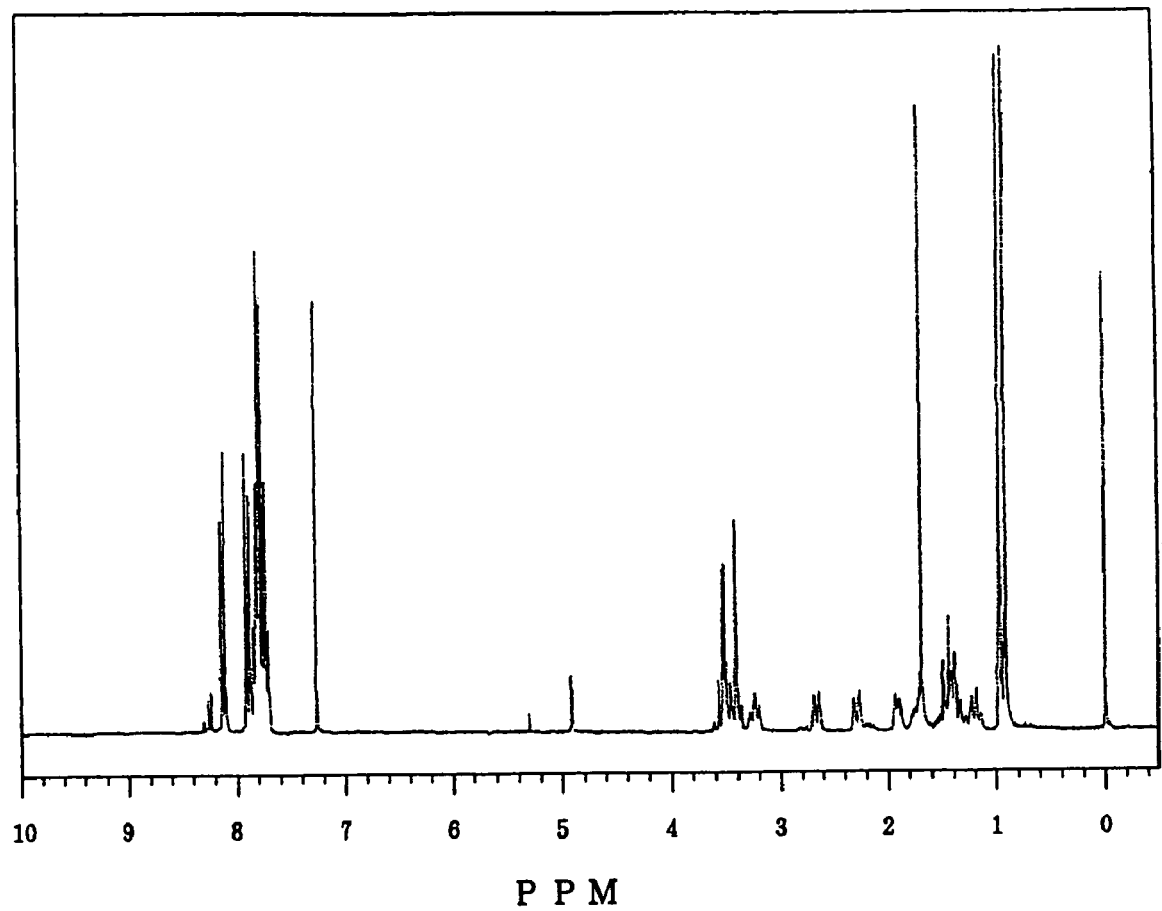
FIG. 29 shows a $^1$H-NMR spectrometry spectrum of the acid generator (A-11).
Figure 30:
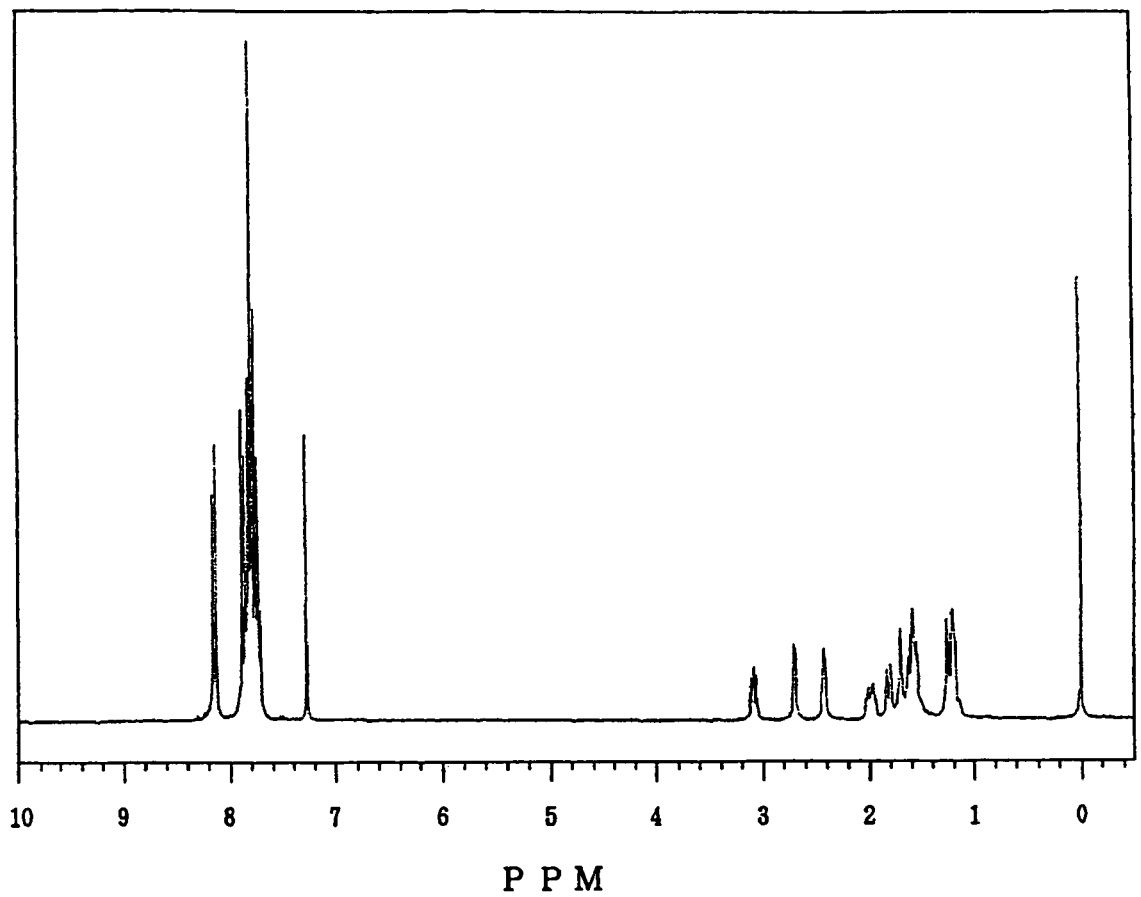
FIG. 30 shows a $^1$H-NMR spectrometry spectrum of the acid generator (A-12).
Figure 31:
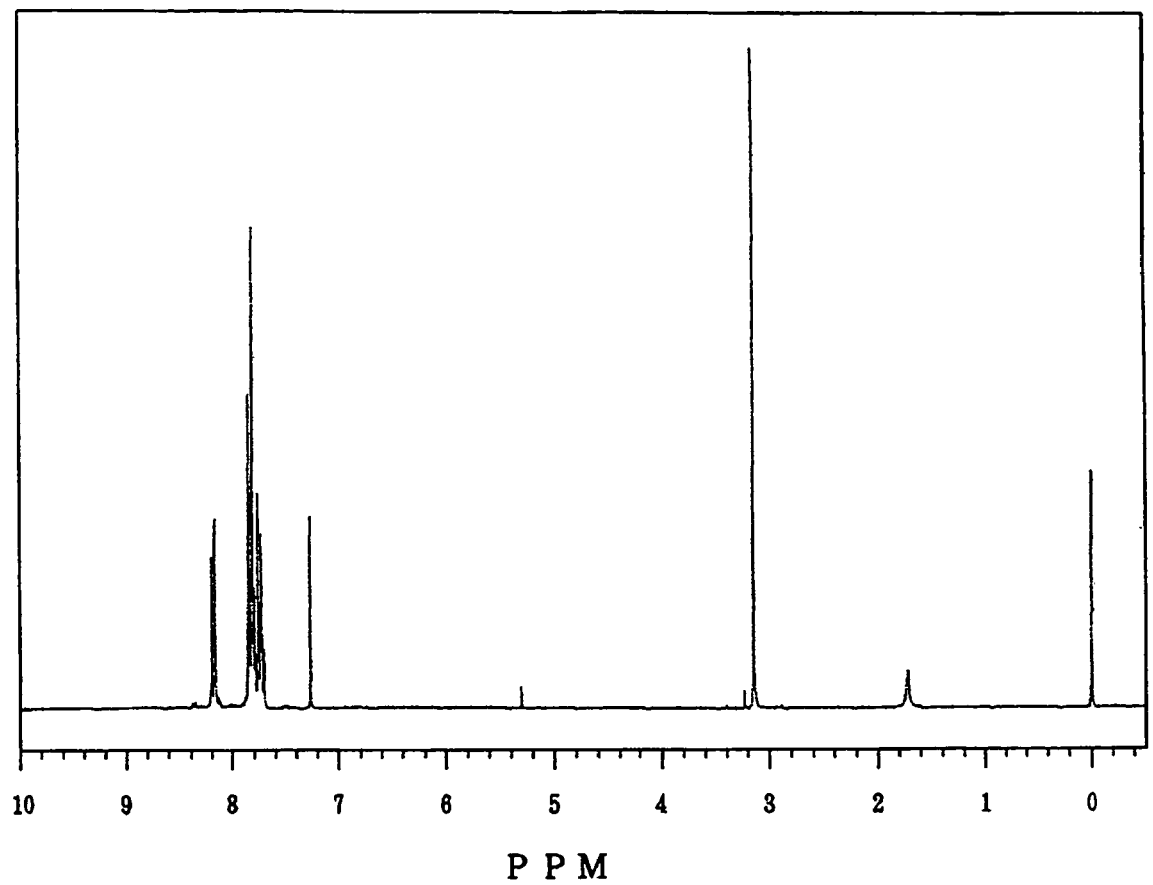
FIG. 31 shows a $^1$H-NMR spectrometry spectrum of the acid generator (A-13).
Figure 32:
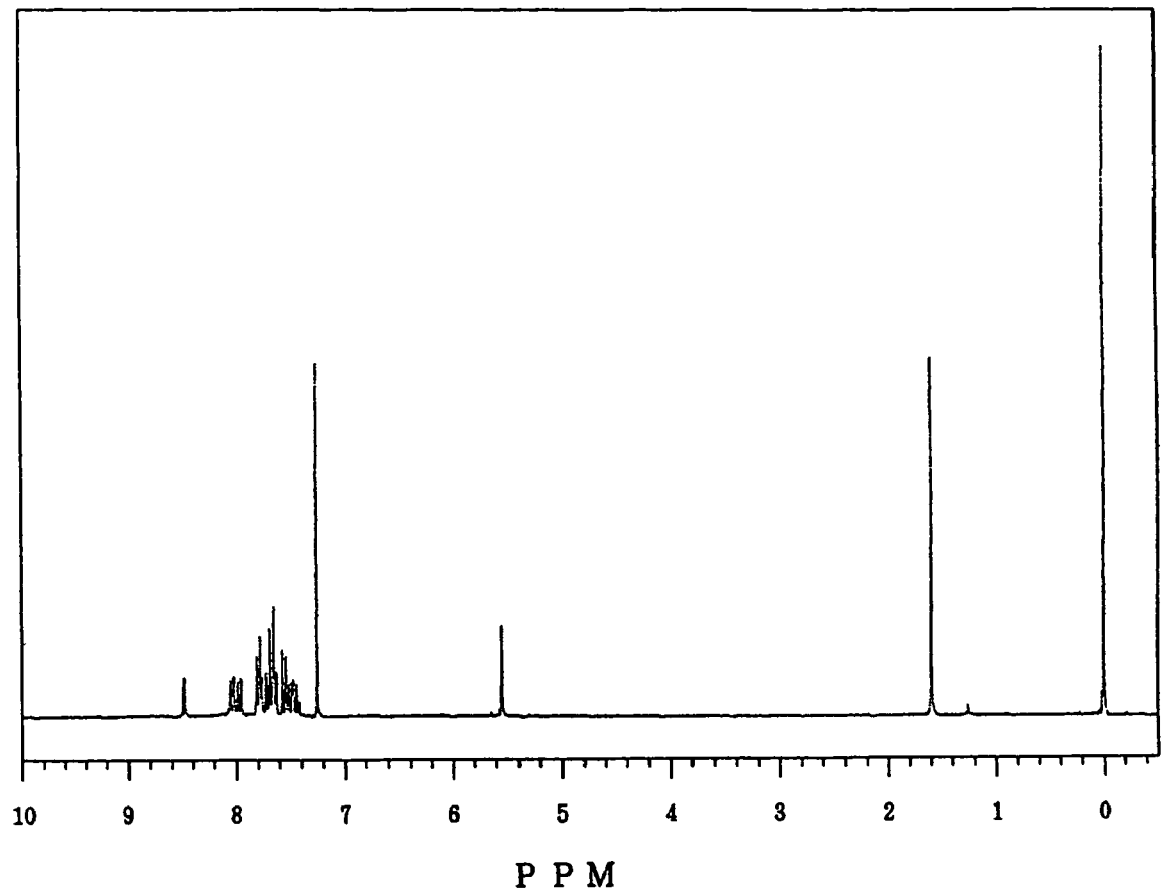
FIG. 32 shows a $^1$H-NMR spectrometry spectrum of the acid generator (A-14).
Figure 33:
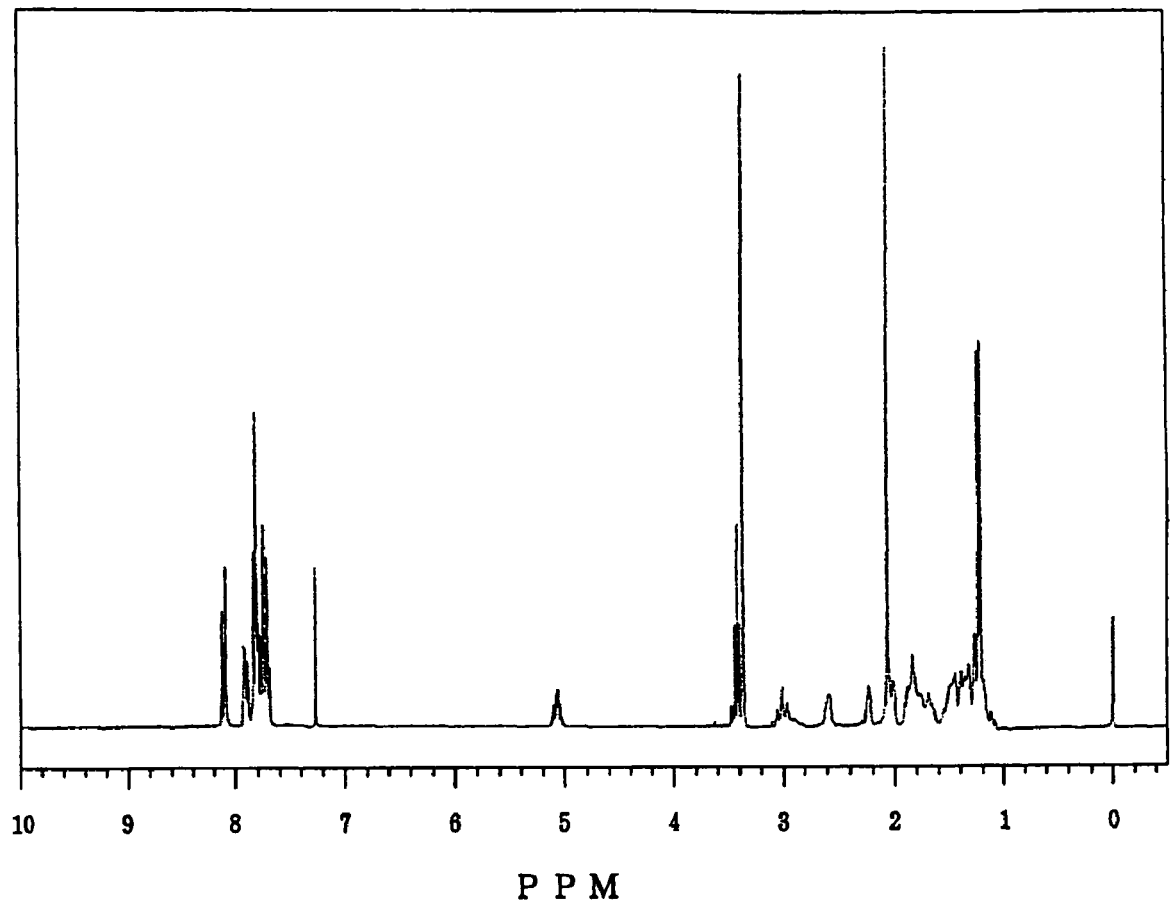
FIG. 33 shows a $^1$H-NMR spectrometry spectrum of the acid generator (A-15).
Figure 34:
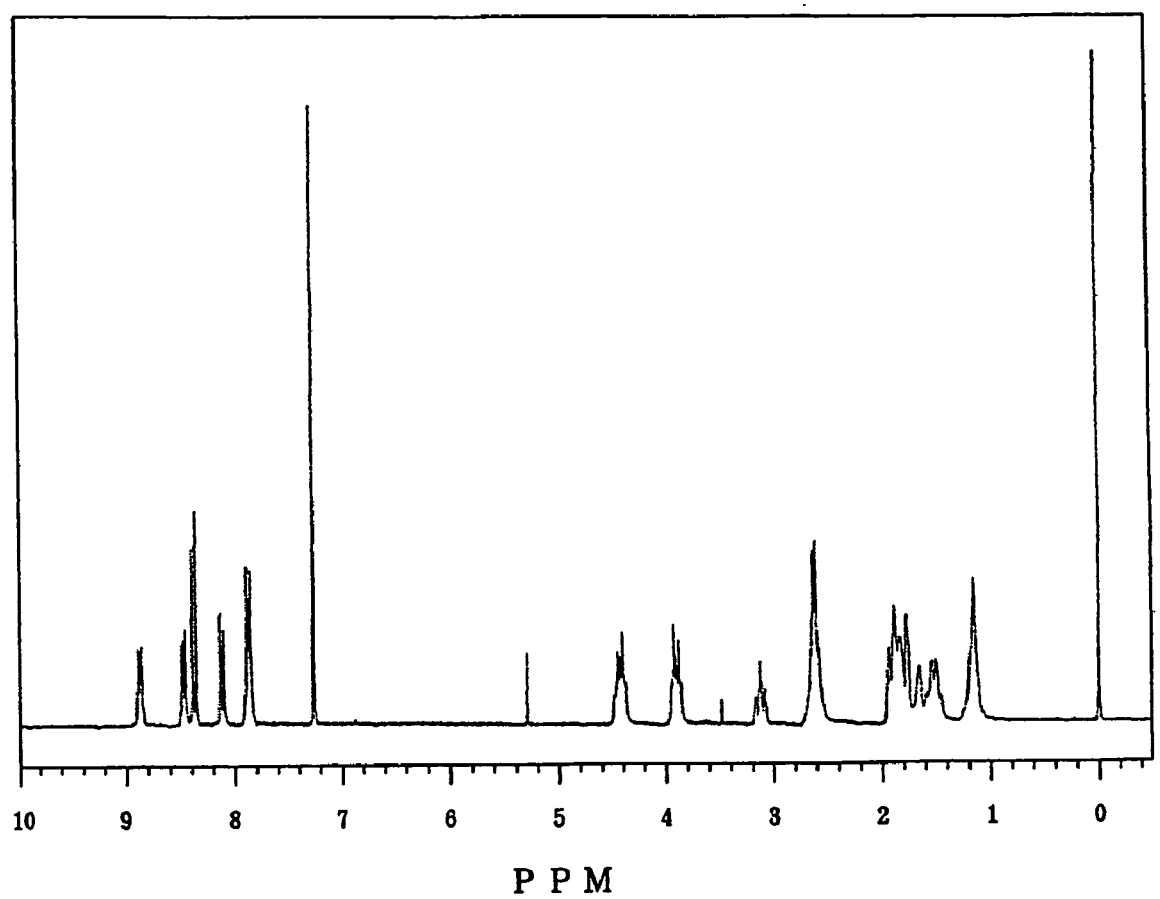
FIG. 34 shows a $^1$H-NMR spectrometry spectrum of the acid generator (A-16).
Figure 35:
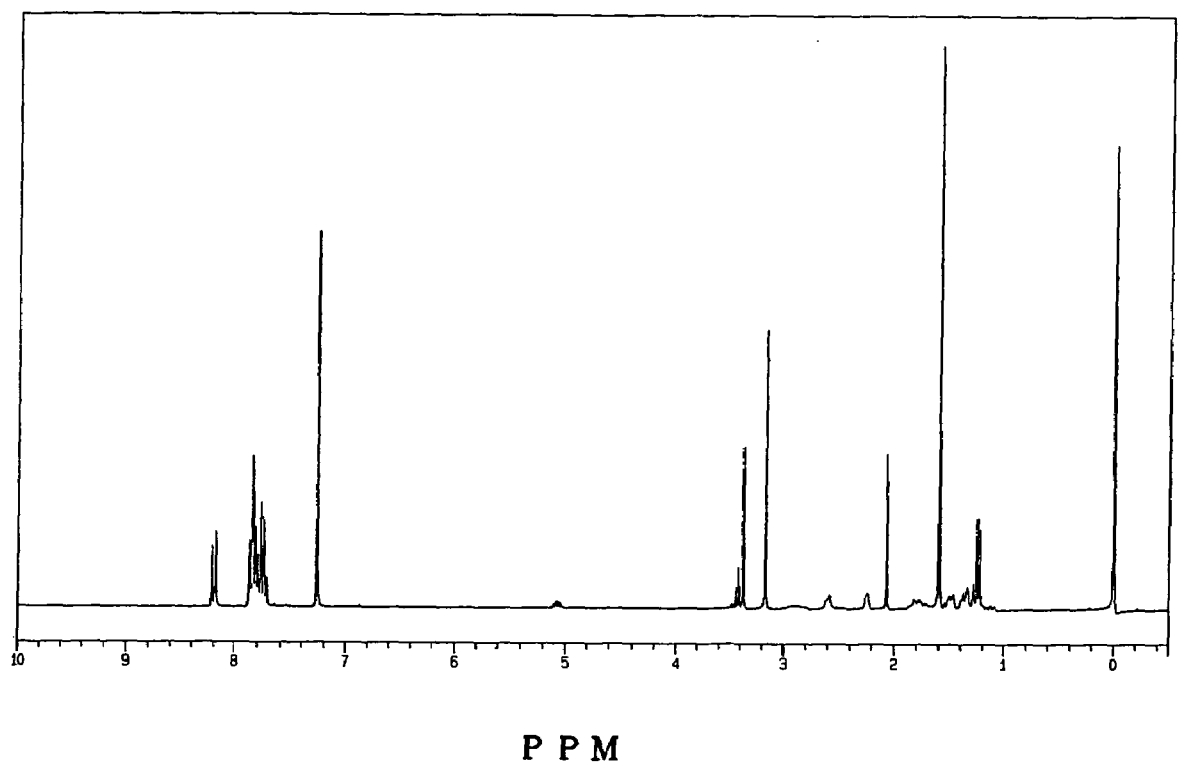
FIG. 35 shows a $^1$H-NMR spectrometry spectrum of the acid generator (A-17).
Figure 36:
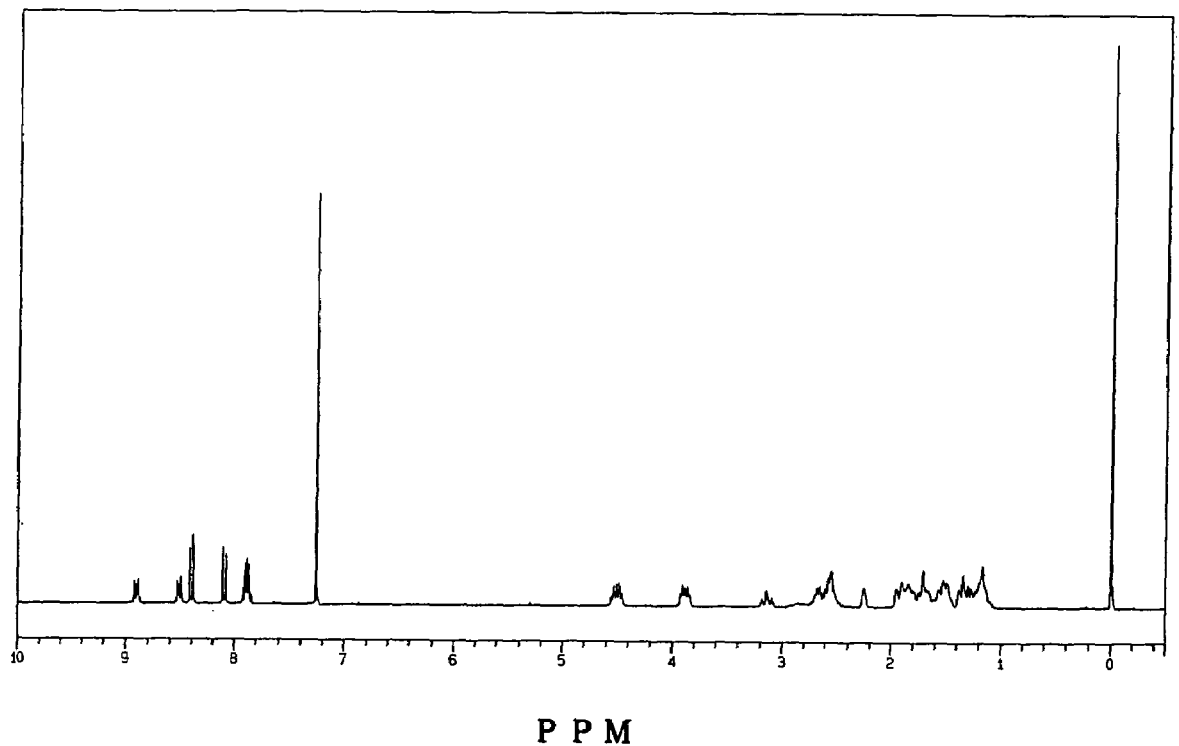
FIG. 36 shows a $^1$H-NMR spectrometry spectrum of the acid generator (A-18).

The acid generators (A-1) to (A-18) were subjected to ¹H-NMR analysis using JNM-EX270 manufactured by JEOL Ltd. The solvent used for the measurement was deuterated chloroform. The spectra obtained are shown in FIGS. 19–36.

<Synthesis of Acid-Dissociable Group-Containing Resin (B)>

Acid-dissociable group-containing resins (B) were synthesized according to the following method.

Mw and Mn of the acid-dissociable group-containing resins (B) were measured by gel permeation chromatography (GPC) using GPC columns (manufactured by Tosoh Corp., G2000HXL×2, G3000HXL×1, G4000HXL×1) under the following conditions. Flow rate: 1.0 ml/minute, eluate: tetrahydrofuran, column temperature: 40° C., standard reference material: monodispersed polystyrene Synthesis Example 19

101 g of p-acetoxystyrene, 5 g of styrene, 42 g of p-t-butoxystyrene, 6 g of azobisisobutylonitrile, and 1 g of t-dodecylmercaptan were dissolved in 160 g of propylene glycol monomethyl ether. The mixture was polymerized for 16 hours while maintaining the reaction temperature at 70° C. in a nitrogen atmosphere. After polymerization, the reaction solution was added dropwise to a large quantity of n-hexane to coagulate and purify the resulting resin. After the addition of 150 g of propylene glycol monomethyl ether to the purified resin, 300 g of methanol, 80 g of triethylamine, and 15 g of water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of water to coagulate the resin. The resulting white powder was filtered and dried overnight at 50° C. under reduced pressure.

The resin was found to have Mw and Mw/Mn of 16,000 and 1.7 respectively. The result of ¹³C-NMR analysis confirmed that the copolymerization molar ratio of p-hydroxystyrene, styrene, and p-t-butoxystyrene of the copolymer was 72:5:23. This resin is indicated as a "resin (B-1)".

Synthesis Example 20

100 g of p-acetoxystyrene, 25 g of t-butyl acrylate, 18 g of styrene, 6 g of azobisisobutyronitrile, and 1 g of t-dodecylmercaptan were dissolved in 230 g of propylene glycol monomethyl ether. The mixture was polymerized for 16 hours while maintaining the reaction temperature at 70° C. in a nitrogen atmosphere. After polymerization, the reaction solution was added dropwise to a large quantity of n-hexane to coagulate and purify the resulting resin. After the addition of 150 g of propylene glycol monomethyl ether to the purified resin, 300 g of methanol, 80 g of triethylamine, and 15 g of water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of water to coagulate the resin. The resulting white powder was filtered and dried overnight at 50° C. under reduced pressure.

The resin was found to have Mw and Mw/Mn of 11,500 and 1.6 respectively. The result of ¹³C-NMR analysis confirmed that the copolymerization molar ratio of p-hydroxystyrene, t-butyl acrylate, and styrene of the copolymer was 61:19:20. This resin is indicated as a "resin (B-2)".

Synthesis Example 21

97 g of p-acetoxystyrene, 51 g of p-t-butoxystyrene, 6 g of azobisisobutyronitrile, and 1 g of t-dodecylmercaptan were dissolved in 160 g of propylene glycol monomethyl ether. The mixture was polymerized for 16 hours while maintaining the reaction temperature at 70° C. in a nitrogen atmosphere. After polymerization, the reaction solution was added dropwise to a large quantity of n-hexane to coagulate and purify the resulting resin. After the addition of 150 g of propylene glycol monomethyl ether to the purified resin, 300 g of methanol, 80 g of triethylamine, and 15 g of water were added. The mixture was hydrolyzed for eight hours while refluxing at the boiling point. After the reaction, the solvent and triethylamine were evaporated under reduced pressure. The resulting resin was dissolved in acetone and added dropwise to a large quantity of water to coagulate the resin. The resulting white powder was filtered and dried overnight at 50° C. under reduced pressure. The resin was found to have Mw and Mw/Mn of 16,500 and 1.7 respectively. The result of ¹³C-NMR analysis confirmed that the copolymerization molar ratio of p-hydroxystyrene and p-t-butoxystyrene of the copolymer was 67:33. This resin is indicated as a "resin (B-3)".

Synthesis Example 22

25 g of poly(p-hydroxystyrene) was dissolved in 80 g of n-butyl acetate, and nitrogen gas was bubbled through the solution for 30 minutes. After the addition of 49 g of di-t-butyl dicarbonate and 25 g of triethylamine as a catalyst, the mixture was reacted for 7 hours at 60° C. After the reaction, n-butyl acetate was evaporated under reduced pressure. The resulting resin was dissolved in acetone and added dropwise to a large quantity of water to coagulate the resin. The resulting white powder was filtered and dried overnight at 50° C. under reduced pressure.

Mw and Mw/Mn of this resin were respectively 12,000 and 1.7. As a result of ¹³C-NMR analysis, the resin was found to have a structure in which 26 mol % of hydrogen atoms of a phenolic hydroxyl group in poly(p-hydroxystyrene) was replaced by t-butoxycarbonyl groups. This resin is indicated as a "resin (B-4)".

Synthesis Example 23

25 g of poly(p-hydroxystyrene) was dissolved in 100 g of propylene glycol monomethyl acetate, and nitrogen gas was bubbled through the solution for 30 minutes. After the addition of 4.8 g of ethyl vinyl ether and, as a catalyst, 1 g of pyridinium p-toluenesulfonate, the mixture was reacted for 12 hours at room temperature. The reaction solution was dropped into 1 wt % ammonium aqueous solution to coagulate the resin. The precipitated resin was filtered and dried overnight at 50° C. under reduced pressure.

Mw and Mw/Mn of this resin were respectively 13,000 and 1.7. As a result of ¹H-NMR analysis, the resin was found to have a structure in which 34 mol % of hydrogen atoms of a phenolic hydroxyl group in poly(p-hydroxystyrene) was replaced by ethoxyethyl groups. This resin is indicated as a "resin (B-5)".

Synthesis Example 24

25 g of a copolymer of 92:8 p-hydroxystyrene and p-t-butoxycarbonyloxystyrene was dissolved in 100 g of propylene glycol monomethyl acetate, and nitrogen gas was bubbled through the solution for 30 minutes. After the addition of 3.3 g of ethyl vinyl ether and, as a catalyst, 1 g of pyridinium p-toluenesulfonate, the mixture was reacted for 12 hours at room temperature. The reaction solution was dropped into 1 wt % ammonium aqueous solution to coagulate the resin. The precipitated white powder was filtered and dried overnight at 50° C. under reduced pressure.

Mw and Mw/Mn of this resin were respectively 13,000 and 1.8. As a result of $^{13}$C-NMR analysis, the resin was found to have a structure in which 23 mol % of hydrogen atoms of the phenolic hydroxyl group in poly (p-hydroxystyrene) was replaced by ethoxyethyl groups, and 8 mol % by t-butyl groups. This resin is indicated as a "resin (B-6)".

Synthesis Example 25

25 g of a copolymer of 90:10 p-hydroxystyrene and p-t-butoxystyrene was dissolved in 100 g of propylene glycol monomethyl acetate, and nitrogen gas was bubbled through the solution for 30 minutes. After the addition of 3.3 g of ethyl vinyl ether and, as a catalyst, 1 g of pyridinium p-toluenesulfonate, the mixture was reacted for 12 hours at room temperature. The reaction solution was dropped into 1 wt % ammonium aqueous solution to coagulate the resin. The precipitated white powder was filtered and dried overnight at 50° C. under reduced pressure.

Mw and Mw/Mn of this resin were respectively 13, 000 and 1.01. As a result of $^{13}$C-NMR analysis, the resin was found to have a structure in which 23 mol % of hydrogen atoms of the phenolic hydroxyl group in poly (p-hydroxystyrene) was replaced by 1-ethoxyethyl groups, and 10 mol % by t-butyl groups. This resin is referred to as a "resin (B-7)".

Synthesis Example 26

A monomer solution was prepared by dissolving 53.69 g of 5-oxo-4-oxatricyclo[4.2.1.0$^{3,7}$]nonan-2-yl methacrylate and 46.31 g of 2-methyladamantan-2-yl methacrylate in 200 g of 2-butanone, and further adding 4.04 g of dimethylazobisisobutyrate.

A 1,000 ml three-necked flask containing 100 g of 2-butanone was purged with nitrogen for 30 minutes and heated to 80° C. while stirring. Then, the above monomer solution was added to the flask using a dripping funnel in four hours. The polymerization reaction was carried out for six hours after initiation of dripping. After the polymerization, the polymer solution was cooled with water to 30° C. or lower and poured into 2,000 g of methanol. White precipitate produced was collected by filtration. The resulting white powder was washed twice with 400 g of methanol, filtered, and dried for 17 hours at 50° C. to obtain a white resin powder.

The resin was found to have Mw and Mw/Mn of 9,700 and 1.91 respectively. The result of $^{13}$C-NMR analysis confirmed that the resin was a copolymer of 5-oxo-4-oxatricyclo[4.2.1.0$^{3,7}$]nonan-2-yl methacrylate and 2-methyladamantan-2-yl methacrylate at a copolymerization molar ratio of 59.6:40.4. This resin is indicated as a "resin (B-8)".

Synthesis Example 27

A monomer solution was prepared by dissolving 40.90 g of 2-methyladamantan-2-yl methacrylate, 15.47 g of 3-hydroxyadamantan-1-yl methacrylate, and 43.64 g of 5-oxo-4-oxatricyclo[4.2.1.0$^{3,7}$]nonan-2-yl methacrylate in 200 g of 2-butanone, and further adding 4.02 g of dimethylazobisbutyrate.

A 1,000 ml three-necked flask containing 100 g of 2-butanone was purged with nitrogen for 30 minutes and heated to 80° C. while stirring. Then, the above monomer solution was added to the flask using a dripping funnel in four hours. The polymerization reaction was carried out for six hours after initiation of dripping. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried for 17 hours at 50° C. to obtain a white resin powder. The resin was found to have Mw and Mw/Mn of 9,200 and 2.02 respectively. The result of $^{13}$C-NMR analysis confirmed that the resin was a copolymer of 2-methyladamantan-2-yl methacrylate, 3-hydroxyadamantan-1-yl methacrylate, and 5-oxo-4-oxatricyclo [4.2.1.0$^{3,7}$]nonan-2-yl methacrylate at a copolymerization molar ratio of 36.2:15.2:48.6. This resin is indicated as a "resin (B-9)".

Synthesis Example 28

A monomer solution was prepared by dissolving 43.66 g of 1-(adamantan-1-yl)-1-methylethyl methacrylate, 14.74 g of 3-hydroxyadamantan-1-yl methacrylate, and 43.66 g of 5-oxo-4-oxatricyclo[4.2.1.0$^{3,7}$]nonan-2-yl methacrylate in 200 g of 2-butanone, and further adding 3.83 g of dimethylazobisbutyrate.

A 1,000 ml three-necked flask containing 100 g of 2-butanone was purged with nitrogen for 30 minutes and heated to 80° C. while stirring. Then, the above monomer solution was added dropwise to the flask using a dripping funnel in four hours. The polymerization reaction was carried out for six hours after initiation of dripping. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried for 17 hours at 50° C. to obtain a white resin powder.

The resin was found to have Mw and Mw/Mn of 9, 600 and 1.85 respectively. The result of $^{13}$C-NMR analysis confirmed that the resin was a copolymer of 1-(adamantan-1-yl)-1-methylethyl methacrylate, 3-hydroxyadamantan-1-yl methacrylate, and 5-oxo-4-oxatricyclo[4.2.1.0$^{3,7}$]nonan-2-yl methacrylate at a copolymerization molar ratio of 35.6:15.1:49.3. This resin is indicated as a "resin (B-10)".

Synthesis Example 29

A monomer solution was prepared by dissolving 16.13 g of 2-ethyladamantan-2-yl methacrylate, 40.58 g of 2-methyladamantan-2-yl methacrylate, and 43.29 g of 5-oxo-4-oxatricyclo[4.2.1.0$^{3,7}$]nonan-2-yl methacrylate (45 mol %) in 200 g of 2-butanone, and further adding 3.99 g of dimethylazobisisobutyrate.

A 1,000 ml three-necked flask containing 100 g of 2-butanone was purged with nitrogen for 30 minutes and heated to 80° C. while stirring. Then, the above monomer solution was added dropwise to the flask using a dripping funnel in four hours. The polymerization reaction was carried out for six hours after initiation of dripping. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried for 17 hours at 50° C. to obtain a white resin powder.

The resin was found to have Mw and Mw/Mn of 8,900 and 1.88 respectively. The result of $^{13}$C-NMR analysis confirmed that the resin was a copolymer of 2-ethyladamantan-2-yl methacrylate, 2-methyladamantan-2-yl methacrylate, and 5-oxo-4-oxatricyclo[4.2.1.0$^{3,7}$]nonan-2-yl methacrylate at a copolymerization molar ratio of 13.7:38.2:48.1. This resin is indicated as a "resin (B-11)".

Synthesis Example 30

A monomer solution was prepared by dissolving 42.44 g of 5-oxo-4-oxatricyclo[4.2.1.0$^{3,7}$]nonan-2-yl acrylate, 15.10 g of 3-hydroxyadamantan-1-yl acrylate, and 42.46 g of 2-ethyladamantan-2-yl acrylate in 200 g of 2-butanone, and further adding 4.17 g of dimethylazobisbutyrate.

A 1,000 ml three-necked flask containing 100 g of 2-butanone was purged with nitrogen for 30 minutes and heated to 80° C. while stirring. Then, the above monomer solution was added dropwise to the flask using a dripping funnel in four hours. The polymerization reaction was carried out for six hours after initiation of dripping. After the polymerization, the polymer solution was cooled with water to 30° C. or lower and poured into 2, 000 g of methanol. White precipitate produced was collected by filtration. The resulting white powder was washed twice with 400 g of methanol in the form of a slurry, filtered, and dried for 17 hours at 50° C. to obtain a white resin powder.

The resin was found to have Mw and Mw/Mn of 10,200 and 2.05 respectively. The result of $^{13}$C-NMR analysis confirmed that the resin was a copolymer of 5-oxo-4-oxatricyclo[4.2.1.0$^{3,7}$]nonan-2-yl acrylate, 3-hydroxyadamantan-1-yl acrylate, and 2-ethyladamantan-2-yl acrylate at a copolymerization molar ratio of 49.2:15.3:35.5. This resin is indicated as a "resin (B-12)".

Synthesis Example 31

A monomer solution was prepared by dissolving 55.00 g of 5-oxo-4-oxatricyclo[4.2.1.0$^{3,7}$]nonan-2-yl methacrylate, 11.70 g of 3-hydroxyadamantan-1-yl methacrylate, and 33.31 g of 1-ethylcyclopentyl acrylate in 200 g of 2-butanone, and further adding 4.56 g of dimethylazobisbutyrate.

A 1,000 ml three-necked flask containing 100 g of 2-butanone was purged with nitrogen for 30 minutes and heated to 80° C. while stirring. Then, the above monomer solution was added dropwise to the flask using a dripping funnel in four hours. The polymerization reaction was carried out for six hours after initiation of dripping. After the polymerization, the polymer solution was cooled with water to 30° C. or lower and poured into 2,000 g of a mixed solvent of 2-propanol/n-heptane at a weight ratio of 1:2 in the form of a slurry. White precipitate produced was collected by filtration. The resulting white powder was washed twice with 400 g of a mixed solvent of 2-propanol/n-heptane at a weight ratio of 1:2, filtered, and dried for 17 hours at 50° C. to obtain a white resin powder.

The resin was found to have Mw and Mw/Mn of 8, 500 and 1.99 respectively. The result of $^{13}$C-NMR analysis confirmed that the resin was a copolymer of 5-oxo-4-oxatricyclo[4.2.1.0$^{3,7}$]nonan-2-yl methacrylate, 3-hydroxyadamantan-1-yl methacrylate, and 1-ethylcyclopentyl acrylate at a copolymerization molar ratio of 53.7:11.1:35.2. This resin is indicated as a "resin (B-13)".

Synthesis Example 32

A three-necked flask equipped with a stirrer, a cold current condenser, and a thermometer was charged with 1.52 g of a triethoxysilane compound providing the recurring unit of the above formula (22-2), 1.57 g of a triethoxysilane compound providing the recurring unit of the above formula (24-2), 1.91 g of methyltriethoxysilane, 15 g of 4-methyl-2-pentanone, and 1.31 g of a 1.75 wt % aqueous solution of oxalic acid. The mixture was reacted for six hours at 80° C. while stirring, followed by cooling to terminate the reaction. The reaction mixture was poured into a separating funnel to remove the water layer. The organic layer was repeatedly washed with ion-exchanged water until the reaction solution becomes neutral. The organic layer was evaporated under reduced pressure.

The resin obtained was found to have Mw and Mw/Mn of 2,000 and 2.32 respectively. The result of $^{13}$C-NMR analysis confirmed that the resin possessed the recurring unit of the formula (22-2) and the recurring unit of the formula (24-1) at a molar ratio of 60:40. This resin is indicated as a "resin (B-14)".

Preparation of Composition Solution

Components shown in Table 1-1 and Table 1-2 (wherein part(s) indicates part(s) by weight) were mixed to prepare homogeneous solutions. The solutions were filtered through a membrane filter with a pore diameter of 0.2 mm to prepare the solution compositions of Examples 1–22 and Comparative Examples 1–2.

In addition to the acid generators (A-1) to (A-6) and resins (B-1) to (B-14) of the Examples and Comparative Examples, the following components were used.

Other Acid Generators
a-1: Triphenylsulfonium trifluoromethanesulfonate
a-2: bis(4-t-butylphenyl)iodoniumtrifluoromethane sulfonate
a-3: N-(trifluoromethanesulfonyloxy)bicyclo[2.2.1]hept-5-ene-2,3-dicarboxyimide Acid Diffusion Controller
C-1: Tri-n-hexylamine
C-2: Triethanolamine
C-3: 2-Phenylbenzimidazole
C-4: 1,2-dimethylimidazole
C-5: 3-Pyperidino-1,2-propanediol Dissolution Controller
D-1: t-Butoxycarbonylmethylester deoxycholate Solvent
S-1: ethyl lactate
S-2: propylene glycol monomethyl ether acetate
S-3: 2-heptanone
S-4: g-Butyrolacton Evaluation The solution compositions of Examples 1–22 and Comparative Examples 1–2 were spin-coated on a silicon wafer. PB was then performed under the conditions shown in Table 2 to form resist coatings with a thickness indicated in Table 2. In accordance with the conditions shown in Table 2, exposure and PEB was conducted. The resist patterns were obtained by developing the resist at 23° C. for one minute by a paddle method using a 2.38 wt % tetramethylammonium hydroxide aqueous solution, followed by washing with purified water and drying.

The following were used as the exposure equipment: Stepper NSR2205 EX12B (numerical aperture: 0.55, manufactured by Nikon Corp.) as the KrF excimer laser (indicated by "KrF" in Table 2); ArF excimer laser photolithography machine (numerical aperture: 0.55, manufactured by Nikon Corp.) as the ArF excimer laser (indicated by "ArF" in Table 2); $F_2$ excimer laser photolithography machine XLS (numerical aperture: 0.60, manufactured by Ultratech) as the $F_2$ excimer laser; Electron Beam Direct Writing System HL700 (acceleration voltage: 30 KeV, manufactured by Hitachi, Ltd.) improved in acceleration voltage to 50 KeV as the electron beam.

Performance evaluations were conducted to the obtained resist patterns by the following means. Evaluation results are shown in Table 3.

Sensitivity

Sensitivity was evaluated based on an optimum exposure dose which is a dose capable of forming a 1:1 line and space pattern (1L1S) with a line width of 0.25 mm, when a resist film formed on a silicon wafer is exposed to light at a varied dose, immediately followed by PEB, development, washing with water, and drying.

Resolution

The minimum dimension of a resist pattern resolved at the optimum dose was taken as the resolution of the resist film.

Pattern Shape

The dimensions of the lower side $L_a$ and the upper side $L_b$ of the rectangular cross-section of a line and space pattern (1L1S) with a line width of 0.25 μm were measured using a scanning electron microscope. A pattern profile which satisfied a formula "$0.85 \leq L_b/L_a \leq 1$" was evaluated as "Good", and otherwise evaluated as "Bad".

Storage Stability

The sensitivity of each liquid composition was evaluated immediately after preparation and after standing at room temperature for one month. After standing for one month, the compositions exhibiting a change in sensitivity of less than 10% as compared with immediately after preparation were evaluated as "Good" and those exhibiting a change of 10% or more were evaluated as "Bad".

TABLE 1-1

|  | Photoacid generator (Parts by weight) | Acid-dissociable group-containing resin (B) (Parts by weight) | Acid diffusion controller (Parts by weight) | Dissolution controller (Parts by weight) | Solvent (Parts by weight) |
|---|---|---|---|---|---|
| Example 1 | A-1 (3) | B-5 (65) B-4 (35) | C-2 (0.3) | — | S-1 (250) S-2 (550) |
| Example 2 | A-2 (2) a-3 (2) | B-5 (70) B-3 (30) | C-1 (0.25) | — | S-2 (800) |
| Example 3 | A-1 (2) a-3 (2) | B-7 (100) | C-1 (0.3) | — | S-1 (250) S-2 (550) |
| Example 4 | A-2 (2) a-3 (2) | B-1 (100) | C-4 (0.4) | — | S-1 (800) |
| Example 5 | A-2 (2) a-2 (1) | B-2 (100) | C-2 (0.3) | — | S-1 (400) S-2 (400) |
| Example 6 | A-2 (2) a-3 (1) | B-6 (100) | C-2 (0.1) C-4 (0.2) | — | S-1 (250) S-2 (550) |
| Example 7 | A-6 (1) a-3 (12) | B-7 (100) | C-1 (0.3) | — | S-4 (600) |
| Example 8 | A-6 (1) a-3 (12) | B-2 (100) | C-1 (0.3) | — | S-4 (600) |
| Example 9 | A-1 (3) | B-8 (100) | C-5 (0.25) | D-1 (8) | S-2 (550) S-4 (50) |
| Example 10 | A-2 (4) | B-8 (100) | C-2 (0.25) | — | S-2 (550) S-4 (50) |
| Example 11 | A-3 (3) | B-8 (100) | C-5 (0.25) | D-1 (8) | S-2 (550) S-4 (50) |
| Example 12 | A-4 (4) | B-8 (100) | C-2 (0.25) | — | S-2 (550) S-4 (50) |

TABLE 1-2

|  | Photoacid generator (Parts by weight) | Acid-dissociable group-containing resin (B) (Parts by weight) | Acid diffusion controller (Parts by weight) | Dissolution controller (Parts by weight) | Solvent (Parts by weight) |
|---|---|---|---|---|---|
| Example 13 | A-5 (3) | B-8 (100) | C-5 (0.25) | D-1 (8) | S-2 (550) S-4 (50) |
| Example 14 | A-2 (4) | B-9 (100) | C-5 (0.25) | — | S-4 (550) S-2 (50) |
| Example 15 | A-2 (4) | B-10 (100) | C-5 (0.25) | — | S-4 (550) S-2 (50) |

TABLE 1-2-continued

|  | Photoacid generator (Parts by weight) | Acid-dissociable group-containing resin (B) (Parts by weight) | Acid diffusion controller (Parts by weight) | Dissolution controller (Parts by weight) | Solvent (Parts by weight) |
|---|---|---|---|---|---|
| Example 16 | A-2 (4) | B-11 (100) | C-5 (0.25) | D-1 (8) | S-4 (550) S-2 (50) |
| Example 17 | A-2 (4) | B-12 (100) | C-2 (0.25) | — | S-4 (600) |
| Example 18 | A-2 (4) | B-13 (100) | C-2 (0.25) | — | S-4 (550) |
| Example 19 | A-6 (4) | B-8 (100) | C-3 (0.1) | — | S-4 (900) |
| Example 20 | A-2 (3) | B-1 (100) | C-4 (0.3) | — | S-1 (400) S-2 (400) |
| Example 21 | A-6 (4) | B-1 (100) | C-4 (0.3) | — | S-1 (400) S-3 (400) |
| Example 22 | A-1 (1.5) | B-14 (100) | C-3 (0.1) | — | S-3 (900) |
| Comparative Example 1 | a-1 (5) | B-5 (65) B-4 (35) | C-1 (0.2) | — | S-1 (250) S-2 (550) |
| Comparative Example 2 | a-1 (4) | B-9 (100) | C-1 (0.3) | — | S-3 (600) |

TABLE 2

|  | Thickness (Å) | PB Temperature (°C.) | PB Time (second) | Exposure source | PEB Temperature (°C.) | PEB Time (second) |
|---|---|---|---|---|---|---|
| Example 1 | 5000 | 100 | 90 | KrF | 110 | 90 |
| Example 2 | 5000 | 100 | 90 | KrF | 110 | 90 |
| Example 3 | 5000 | 100 | 90 | KrF | 100 | 90 |
| Example 4 | 5000 | 120 | 90 | KrF | 130 | 90 |
| Example 5 | 5000 | 120 | 90 | KrF | 140 | 90 |
| Example 6 | 5000 | 100 | 90 | KrF | 110 | 90 |
| Example 7 | 2300 | 130 | 60 | KrF | 130 | 90 |
| Example 8 | 2300 | 130 | 60 | KrF | 130 | 90 |
| Example 9 | 3300 | 130 | 90 | ArF | 130 | 90 |
| Example 10 | 3300 | 130 | 90 | ArF | 130 | 90 |
| Example 11 | 3300 | 130 | 90 | ArF | 130 | 90 |
| Example 12 | 3300 | 120 | 90 | ArF | 130 | 90 |
| Example 13 | 3300 | 130 | 90 | ArF | 130 | 90 |
| Example 14 | 3300 | 130 | 90 | ArF | 130 | 90 |
| Example 15 | 3300 | 130 | 90 | ArF | 120 | 90 |
| Example 16 | 3300 | 120 | 90 | ArF | 100 | 90 |
| Example 17 | 3300 | 130 | 90 | ArF | 100 | 90 |
| Example 18 | 3300 | 130 | 90 | ArF | 110 | 90 |
| Example 19 | 4000 | 130 | 90 | ArF | 110 | 90 |
| Example 20 | 3000 | 120 | 90 | Electron beam | 130 | 90 |
| Example 21 | 3000 | 120 | 90 | Electron beam | 130 | 90 |
| Example 22 | 1000 | 130 | 90 | F2 | 110 | 90 |
| Comparative Example 1 | 5000 | 100 | 90 | KrF | 110 | 90 |
| Comparative Example 2 | 5000 | 130 | 90 | ArF | 140 | 90 |

TABLE 3

|  | Sensitivity | Resolution (μm) | Pattern shape | Storage stability |
|---|---|---|---|---|
| Example 1 | 300 J/m$^2$ | 0.15 | Good | Good |
| Example 2 | 310 J/m$^2$ | 0.15 | Good | Good |
| Example 3 | 290 J/m$^2$ | 0.15 | Good | Good |
| Example 4 | 330 J/m$^2$ | 0.14 | Good | Good |
| Example 5 | 320 J/m$^2$ | 0.16 | Good | Good |
| Example 6 | 320 J/m$^2$ | 0.15 | Good | Good |
| Example 7 | 330 J/m$^2$ | 0.13 | Good | Good |
| Example 8 | 330 J/m$^2$ | 0.13 | Good | Good |
| Example 9 | 375 J/m$^2$ | 0.14 | Good | Good |
| Example 10 | 382 J/m$^2$ | 0.14 | Good | Good |
| Example 11 | 385 J/m$^2$ | 0.14 | Good | Good |
| Example 12 | 370 J/m$^2$ | 0.14 | Good | Good |
| Example 13 | 375 J/m$^2$ | 0.14 | Good | Good |
| Example 14 | 428 J/m$^2$ | 0.13 | Good | Good |
| Example 15 | 419 J/m$^2$ | 0.13 | Good | Good |
| Example 16 | 319 J/m$^2$ | 0.14 | Good | Good |
| Example 17 | 296 J/m$^2$ | 0.13 | Good | Good |
| Example 18 | 323 J/m$^2$ | 0.13 | Good | Good |
| Example 19 | 450 J/m$^2$ | 0.13 | Good | Good |
| Example 20 | 0.03 C/m$^2$ | 0.14 | Good | Good |
| Example 21 | 0.035 C/m$^2$ | 0.14 | Good | Good |
| Example 22 | 210 J/m$^2$ | 0.13 | Good | Good |
| Comparative Example 1 | 360 J/m$^2$ | 0.16 | Bad | Bad |
| Comparative Example 2 | 700 J/m$^2$ | 0.16 | Bad | Bad |

TABLE 4-1

|  | Photoacid generator (Parts by weight) | Acid-dissociable group-containing resin (B) (Parts by weight) | Acid diffusion controller (Parts by weight) | Dissolution controller (Parts by weight) | Solvent (Parts by weight) |
| --- | --- | --- | --- | --- | --- |
| Example 23 | A-7 (3) | B-5 (65) B-4 (35) | C-2 (0.3) | — | S-1 (250) S-2 (550) |
| Example 24 | A-8 (2) a-3 (2) | B-5 (70) B-3 (30) | C-1 (0.25) | — | S-2 (800) |
| Example 25 | A-7 (2) a-3 (2) | B-7 (100) | C-1 (0.3) | — | S-1 (250) S-2 (550) |
| Example 26 | A-9 (2) a-3 (2) | B-1 (100) | C-1 (0.4) | — | S-1 (800) |
| Example 27 | A-9 (2) a-2 (1) | B-2 (100) | C-1 (0.3) | — | S-1 (400) S-2 (400) |
| Example 28 | A-8 (2) A-3 (1) | B-6 (100) | C-1 (0.1) C-4 (0.2) | — | S-1 (250) S-2 (550) |
| Example 29 | A-7 (3) | B-8 (100) | C-5 (0.25) | D-1 (8) | S-2 (550) S-4 (50) |
| Example 30 | A-8 (3) | B-8 (100) | C-2 (0.25) | — | S-2 (550) S-4 (50) |
| Example 31 | A-9 (5) | B-8 (100) | C-2 (0.25) | — | S-2 (550) S-4 (50) |
| Example 32 | A-8 (4) | B-9 (100) | C-5 (0.25) | — | S-2 (550) S-4 (50) |
| Example 33 | A-8 (4) | B-10 (100) | C-5 (0.25) | — | S-2 (550) S-4 (50) |
| Example 34 | A-8 (4) | B-11 (100) | C-5 (0.25) | D-1 (8) | S-2 (550) S-4 (50) |
| Example 35 | A-8 (4) | B-12 (100) | C-2 (0.25) | — | S-2 (600) |
| Example 36 | A-8 (4) | B-13 (100) | C-2 (0.25) | — | S-2 (550) |
| Example 37 | A-8 (3) | B-1 (100) | C-4 (0.25) | — | S-1 (400) S-2 (400) |

TABLE 4-2

|  | Photoacid generator (Parts by weight) | Acid-dissociable group-containing resin (B) (Parts by weight) | Acid diffusion controller (Parts by weight) | Dissolution controller (Parts by weight) | Solvent (Parts by weight) |
| --- | --- | --- | --- | --- | --- |
| Example 38 | A-9 (1.5) | B-14 (100) | C-3 (0.1) | — | S-3 (900) |
| Example 39 | A-10 (3) | B-8 (100) | C-5 (0.25) | — | S-2 (550) S-4 (50) |
| Example 40 | A-11 (3) | B-8 (100) | C-5 (0.25) | — | S-2 (550) S-4 (50) |
| Example 41 | A-12 (3) | B-8 (100) | C-5 (0.25) | — | S-2 (550) S-4 (50) |
| Example 42 | A-13 (4) | B-8 (100) | C-5 (0.25) | — | S-2 (550) S-4 (50) |
| Example 43 | A-14 (3) | B-8 (100) | C-5 (0.25) | — | S-2 (550) S-4 (50) |
| Example 44 | A-15 (2) | B-8 (100) | C-5 (0.25) | — | S-2 (550) S-4 (50) |
| Example 45 | A-16 (6) | B-8 (100) | C-5 (0.25) | — | S-2 (550) S-4 (50) |
| Example 46 | A-16 (3) | B-12 (100) | C-4 (0.20) | — | S-2 (550) S-4 (50) |
| Example 47 | A-17 (6) | B-8 (100) | C-5 (0.25) | — | S-2 (550) S-4 (50) |
| Example 48 | A-18 (6) | B-8 (100) | C-5 (0.25) | — | S-2 (550) S-4 (50) |

TABLE 5

|  | Thickness (Å) | PB | | | PEB | |
| --- | --- | --- | --- | --- | --- | --- |
|  |  | Temperature (° C.) | Time (second) | Exposure source | Temperature (° C.) | Time (second) |
| Example 23 | 5000 | 100 | 90 | KrF | 110 | 90 |
| Example 24 | 5000 | 100 | 90 | KrF | 110 | 90 |
| Example 25 | 5000 | 100 | 90 | KrF | 100 | 90 |
| Example 26 | 5000 | 120 | 90 | KrF | 130 | 90 |

TABLE 5-continued

| | Thick-ness (Å) | PB Temperature (° C.) | PB Time (second) | Exposure source | PEB Temperature (° C.) | PEB Time (second) |
|---|---|---|---|---|---|---|
| Example 27 | 5000 | 120 | 90 | KrF | 140 | 90 |
| Example 28 | 5000 | 100 | 90 | KrF | 110 | 90 |
| Example 29 | 3300 | 130 | 90 | ArF | 130 | 90 |
| Example 30 | 3300 | 130 | 90 | ArF | 130 | 90 |
| Example 31 | 3300 | 130 | 90 | ArF | 130 | 90 |
| Example 32 | 3300 | 130 | 90 | ArF | 130 | 90 |
| Example 33 | 3300 | 130 | 90 | ArF | 120 | 90 |
| Example 34 | 3300 | 120 | 90 | ArF | 100 | 90 |
| Example 35 | 3300 | 130 | 90 | ArF | 100 | 90 |
| Example 36 | 3300 | 130 | 90 | ArF | 110 | 90 |
| Example 37 | 3000 | 120 | 90 | Electron beam | 130 | 90 |
| Example 38 | 1000 | 130 | 90 | F2 | 110 | 90 |
| Example 39 | 3300 | 130 | 90 | ArF | 130 | 90 |
| Example 40 | 3300 | 130 | 90 | ArF | 130 | 90 |
| Example 41 | 3300 | 130 | 90 | ArF | 130 | 90 |
| Example 42 | 3300 | 130 | 90 | ArF | 130 | 90 |
| Example 43 | 3300 | 130 | 90 | ArF | 130 | 90 |
| Example 44 | 3300 | 130 | 90 | ArF | 130 | 90 |
| Example 45 | 3300 | 130 | 90 | ArF | 130 | 90 |
| Example 46 | 3300 | 130 | 90 | ArF | 130 | 90 |
| Example 47 | 3300 | 130 | 90 | ArF | 130 | 90 |
| Example 48 | 3300 | 130 | 90 | ArF | 130 | 90 |

TABLE 6

| | Sensitivity | Resolution (μm) | Pattern shape | Storage stability |
|---|---|---|---|---|
| Example 23 | 320 J/m² | 0.15 | Good | Good |
| Example 24 | 330 J/m² | 0.15 | Good | Good |
| Example 25 | 350 J/m² | 0.15 | Good | Good |
| Example 26 | 350 J/m² | 0.14 | Good | Good |
| Example 27 | 370 J/m² | 0.16 | Good | Good |
| Example 28 | 320 J/m² | 0.15 | Good | Good |
| Example 29 | 382 J/m² | 0.14 | Good | Good |
| Example 30 | 403 J/m² | 0.14 | Good | Good |
| Example 31 | 582 J/m² | 0.13 | Good | Good |
| Example 32 | 443 J/m² | 0.13 | Good | Good |
| Example 33 | 452 J/m² | 0.13 | Good | Good |
| Example 34 | 352 J/m² | 0.14 | Good | Good |
| Example 35 | 337 J/m² | 0.13 | Good | Good |
| Example 36 | 368 J/m² | 0.13 | Good | Good |
| Example 37 | 0.03 C/m² | 0.14 | Good | Good |
| Example 38 | 190 J/m² | 0.13 | Good | Good |
| Example 39 | 452 J/m² | 0.14 | Good | Good |
| Example 40 | 520 J/m² | 0.13 | Good | Good |
| Example 41 | 535 J/m² | 0.13 | Good | Good |
| Example 42 | 485 J/m² | 0.14 | Good | Good |
| Example 43 | 449 J/m² | 0.15 | Good | Good |
| Example 44 | 475 J/m² | 0.16 | Good | Good |
| Example 45 | 550 J/m² | 0.14 | Good | Good |
| Example 46 | 525 J/m² | 0.13 | Good | Good |
| Example 47 | 550 J/m² | 0.13 | Good | Good |
| Example 48 | 550 J/m² | 0.14 | Good | Good |

Tables 3 and 6 clearly show that the positive-tone radiation sensitive resin composition using the acid generator (A) of the present invention excels in storage stability and base resistance, is highly sensitive, and has a high resolution as compared with the positive-tone radiation sensitive resin compositions of the Comparative Examples.

The onium salt compound (1) and onium salt compound (2) of the present invention, excelling in storage stability and being highly sensitive to active rays, particularly deep ultraviolet rays represented, for example, by a KrF excimer laser, ArF excimer laser, and F$_2$ excimer laser and electron beams, is useful as a chemically-amplified photoresist for a photoacid generator used in microfabrication represented by the manufacture of integrated circuit devices. Furthermore, the positive-tone radiation sensitive resin composition of the present invention using the acid generator (A) comprising these onium salt compounds as essential components excels in storage stability, is highly sensitive, has a high resolution, and is very useful as a chemically amplified resist in the manufacture of integrated circuit elements of which downsizing is anticipated to proceed in the future.

What is claimed is:

1. An onium salt compound having a cation moiety of the following formula (1),

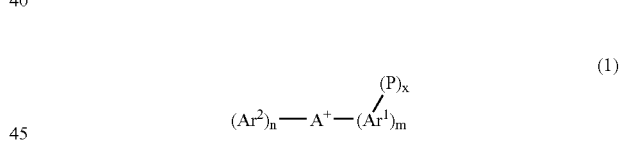

(1)

wherein A represents an iodine atom or a sulfur atom, when A is an iodine atom, m is 1 or 2 and n is 0 or 1, provided that (m+n)=2, and x is an integer of 1–10, and when A is a sulfur atom, m is 1–3 and n is 0–2, provided that (m+n)=3, and x is an integer of 1–15; Ar$^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), Ar$^2$ represents a substituted or unsubstituted monovalent aromatic hydrocarbon group having 6–20 carbon atoms or a substituted or unsubstituted monovalent heterocyclic group having 3–20 atoms, or Ar$^1$ and Ar$^2$ mutually bond together with A$^+$ in the formula to form a group possessing a cyclic structure with 3–8 atoms; and the x-number of P groups bonding to one or more of the m-number of Ar$^1$ groups individually represent —O—SO$_2$R$^1$, —O—S(O)R$^2$, or —SO$_2$R$^3$, wherein R$^1$, R$^2$, and R$^3$ individually represent a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group —N(R')$_2$, wherein R' individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or two R' groups form, in combination and together with the nitrogen atom in the formula, a group having a cyclic structure with 3–8 atoms and wherein R$^3$ represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, or a substituted or unsubstituted monovalent heterocyclic group having 3–20 atoms, or a group —N(R')$_2$, wherein R' individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or two R' groups form, in combination and together with the nitrogen atom in the formula, a group having a cyclic structure with 3–8 atoms.

2. The onium salt compound according to claim 1, wherein A in formula (1) is a sulfur atom.

3. An onium salt compound having a cationic moiety of the following formula (2),

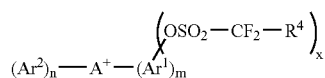

(2)

wherein A represents an iodine atom or a sulfur atom, when A is an iodine atom, m is 1 or 2 and n is 0 or 1, provided that (m+n)=2, and x is an integer of 1–10, and when A is a sulfur atom, m is 1–3 and n is 0–2, provided that (m+n)=3, and x is an integer of 1–15; Ar$^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), Ar$^2$ represents a substituted or unsubstituted monovalent aromatic hydrocarbon group having 6–20 carbon atoms or a substituted or unsubstituted monovalent heterocyclic group having 3–20 atoms, or Ar$^1$ and Ar$^2$ mutually bond together with A$^+$ in the formula to form a group possessing a cyclic structure with 3–8 atoms and R$^4$ represents a hydrogen atom, fluorine atom, nitro group, cyano group, or a monovalent organic group having 1–20 carbon atoms.

4. The onium salt compound according to claim 3, wherein A in formula (2) is a sulfur atom.

5. The onium salt compound according to claim 3, wherein R$^4$ in the formula (2) is a group of the following formula (3),

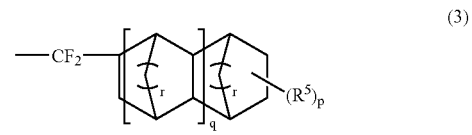

(3)

wherein R$^5$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, a substituted or unsubstituted monovalent heterocyclic group having 3–20 atoms, or a group —N(R$^{2'}$)$_2$, wherein R$^{2'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted, monovalent heterocyclic group having 3–20 atoms, or two R$^{2'}$ groups form, in combination and together with the nitrogen atom in the formula, a group having a cyclic structure with 3–8 atoms, p is an integer of 0–16, q is an integer of 0–8, and r is an integer of 1–3.

6. An onium salt compound according to claim 5, wherein both p and q are 0 and both r's are 1.

7. An onium salt compound having a cationic moiety represented by the following formula (4)

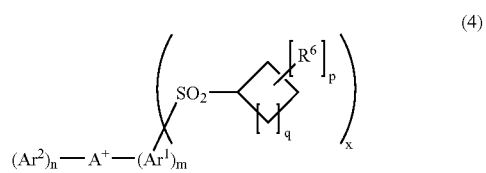

(4)

wherein A represents an iodine atom or a sulfur atom, when A is an iodine atom, m is 1 or 2 and n is 0 or 1, provided that (m+n)=2, and x is an integer of 1–10, and when A is a sulfur atom, m is 1–3 and n is 0–2, provided that (m+n)=3, and x is an integer of 1–15; Ar$^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), Ar$^2$ represents a substituted or unsubstituted monovalent aromatic hydrocarbon group having 6–20 carbon atoms or a substituted or unsubstituted monovalent heterocyclic group having 3–20 atoms, or Ar$^1$ and Ar$^2$ mutually bond together with A$^+$ in the formula to form a group possessing a cyclic structure with 3–8 atoms; p is an integer of 0–16; q is an integer of 0–8; and R$^6$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group or a group —N(R$^{3'}$)$_2$, wherein R$^{3'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted, monovalent heterocyclic group having 3–20 atoms, or two $R^{3'}$ groups form, in combination and together with the nitrogen atom in the formula, a group having a cyclic structure with 3–8 atoms.

8. An onium salt compound having a cationic moiety represented by the following formula (5),

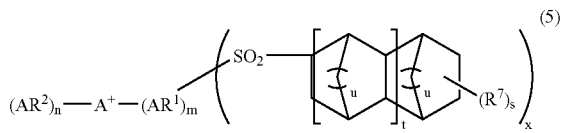

wherein A represents an iodine atom or a sulfur atom, when A is an iodine atom, m is 1 or 2 and n is 0 or 1, provided that (m+n)=2, and x is an integer of 1–10, and when A is a sulfur atom, m is 1–3 and n is 0–2, provided that (m+n)=3, and x is an integer of 1–15; $Ar^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), $Ar^2$ represents a substituted or unsubstituted monovalent aromatic hydrocarbon group having 6–20 carbon atoms or a substituted or unsubstituted monovalent heterocyclic group having 3–20 atoms, or $Ar^1$ and $Ar^2$ mutually bond together with $A^+$ in the formula to form a group possessing a cyclic structure with 3–8 atoms, or $Ar^1$ and $Ar^2$ mutually bond together with $A^+$ in the formula to form a group possessing a cyclic structure with 3–8 atoms; $R^7$ represents a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group $-N(R^{4'})_2$, wherein $R^{4'}$ individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted, monovalent heterocyclic group having 3–20 atoms, or two $R^{4'}$ groups form, in combination and together with the nitrogen atom in the formula, a group having a cyclic structure with 3–8 atoms, s is an integer of 0–6, t is an integer of 0–5, and u is an integer of 1–3.

9. An onium salt compound having a cationic moiety represented by the following formula (6),

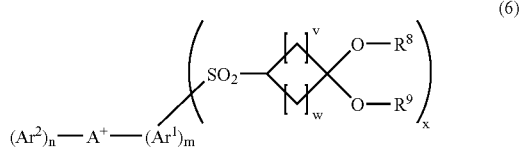

wherein A represents an iodine atom or a sulfur atom, when A is an iodine atom, m is 1 or 2 and n is 0 or 1, provided that (m+n)=2, and x is an integer of 1–10, and when A is a sulfur atom, m is 1–3 and n is 0–2, provided that (m+n)=3, and x is an integer of 1–15; $Ar^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), $Ar^2$ represents a substituted or unsubstituted monovalent aromatic hydrocarbon group having 6–20 carbon atoms or a substituted or unsubstituted monovalent heterocyclic group having 3–20 atoms, or $Ar^1$ and $Ar^2$ mutually bond together with $A^+$ in the formula to form a group possessing a cyclic structure with 3–8 atoms, or $Ar^1$ and $Ar^2$ mutually bond together with $A^+$ in the formula to form a group possessing a cyclic structure with 3–8 atoms; $R^8$ and $R^9$ individually represent a substituted or unsubstituted alkyl group having 1–20 carbon atoms or a substituted or unsubstituted monovalent alicyclic group having 3–20 carbon atoms, or $R^8$ and $R^9$ may form, in combination and together with one carbon atom and two oxygen atoms in the formula, a group having a cyclic structure with 4–10 atoms; and v and w are respectively the integers of 0–5, satisfying the formula (v+w)≧1.

10. A positive tone radiation-sensitive resin composition comprising:
(A) at least one onium salt compound having a cation moiety of the following formula (1),

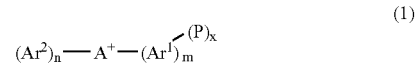

wherein A represents an iodine atom or a sulfur atom, when A is an iodine atom, m is 1 or 2 and n is 0 or 1, provided that (m+n)=2, and x is an integer of 1–10, and when A is a sulfur atom, m is 1–3 and n is 0–2, provided that (m+n)=3, and x is an integer of 1–15; $Ar^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), $Ar^2$ represents a substituted or unsubstituted monovalent aromatic hydrocarbon group having 6–20 carbon atoms or a substituted or unsubstituted monovalent heterocyclic group having 3–20 atoms, or $Ar^1$ and $Ar^2$ mutually bond together with $A^+$ in the formula to form a group possessing a cyclic structure with 3–8 atoms; and the x-number of P groups bonding to one or more of the m-number of $Ar^1$ groups individually represent $-O-SO_2R^1$, $-O-S(O)R^2$, or $-SO_2R^3$, wherein $R^1$, $R^2$, and $R^3$ individually represent a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group $-N(R')_2$, wherein R' individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or two R' groups form, in combination and together with the nitrogen atom in the formula, a group having a cyclic structure with 3–8 atoms; and (B) a resin having an acid-dissociable group and which is insoluble or scarcely soluble in alkali, but which becomes alkali soluble when the acid-dissociable group dissociates.

11. The positive tone radiation-sensitive resin composition according to claim 10, wherein the onium salt compound is selected from the onium salt compounds having —SO$_2$R$^3$ for the group P in the formula (1).

12. A positive tone radiation-sensitive resin composition comprising (A) at least one onium salt compound according to claim 3 as a photoacid generator; and (B) a resin having an acid-dissociable group and which is insoluble or scarcely soluble in alkali, but becomes alkali soluble when the acid-dissociable group dissociates.

13. A positive tone radiation-sensitive resin composition comprising: (A) at least one onium salt compound according to claim 5 as a photoacid generator; and (B) a resin having an acid-dissociable group and which is insoluble or scarcely soluble in alkali, but becomes alkali soluble when the acid-dissociable group dissociates.

14. An onium salt compound having a cation moiety of the following formula (1),

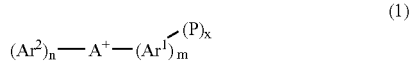

(1)

wherein A represents an iodine atom or a sulfur atom, when A is an iodine atom, m is 1 or 2 and n is 0 or 1, provided that (m+n)=2, and x is an integer of 1–10, and when A is a sulfur atom, m is 2 or 3 and n is 0 or 1, provided that (m+n)=3, and x is an integer of 1–15; Ar$^1$ represents a substituted or unsubstituted aromatic hydrocarbon group having 6–20 carbon atoms with a valence of 1 to (x+1) or a substituted or unsubstituted heterocyclic group having 3–20 atoms with a valence of 1 to (x+1), Ar$^2$ represents a substituted or unsubstituted monovalent aromatic hydrocarbon group having 6–20 carbon atoms or a substituted or unsubstituted monovalent heterocyclic group having 3–20 atoms, or Ar$^1$ and Ar$^2$ mutually bond together with A$^+$ in the formula to form a group possessing a cyclic structure with 3–8 atoms; and the x-number of P groups bonding to the m-number of Ar$^1$ groups individually represent —O—SO$_2$R$^1$, —O—S(O) R$^2$, or —SO$_2$R$^3$, wherein R$^1$, R$^2$, and R$^3$ individually represent a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or a group —N(R')$_2$, wherein R' individually represents a hydrogen atom, a substituted or unsubstituted alkyl group having 1–20 carbon atoms, a substituted or unsubstituted monovalent alicyclic hydrocarbon group having 3–20 carbon atoms, an alkenyl group having 2–20 carbon atoms, a substituted or unsubstituted monovalent aromatic hydrocarbon group having 6–20 carbon atoms, or a substituted or unsubstituted monovalent heterocyclic group having 3–20 atoms, or two R' groups form, in combination and together with the nitrogen atom in the formula, a group having a cyclic structure with 3–8 atoms.

15. A positive tone radiation-sensitive resin composition comprising:

(A) at least one onium salt compound having a cation moiety selected from the group consisting of:

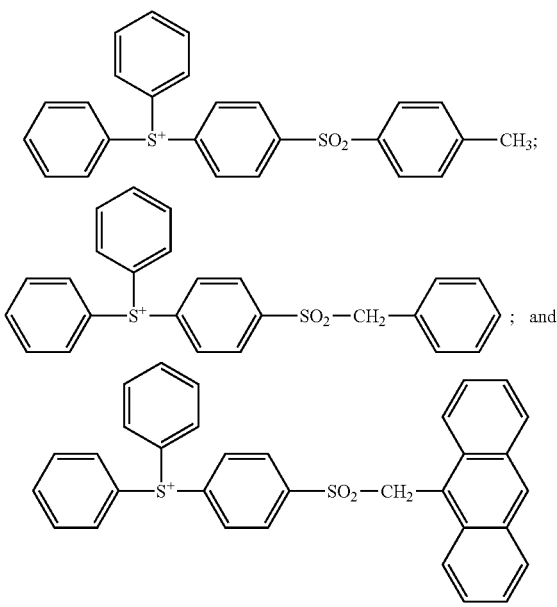

as a photoacid generator and;

(B) a resin having an acid-dissociable group and which is insoluble or scarcely soluble in alkali, but becomes alkali soluble when the acid-dissociable group dissociates.

* * * * *

UNITED STATES PATENT AND TRADEMARK OFFICE
CERTIFICATE OF CORRECTION

PATENT NO. : 7,217,492 B2  Page 1 of 1
APPLICATION NO. : 10/743809
DATED : May 15, 2007
INVENTOR(S) : Yoneda et al.

It is certified that error appears in the above-identified patent and that said Letters Patent is hereby corrected as shown below:

Column 84, line 63, "$R^1, R^2,$" should read --$R^1$ and $R^2$--

Column 84, line 64, "and $R^3$" should be deleted.

Column 86, line 64, "or a group" should be deleted.

Column 87, line 15, "$(AR^2)_n\text{-}A^+\text{-}(AR^1)_m$" should read --$(Ar^2)_n\text{-}A^+\text{-}(Ar^1)_m$--.

Column 87, line 60, "$[\ ]^v$" should read --$[\ ]_v$--.

Signed and Sealed this

Twenty-first Day of August, 2007

JON W. DUDAS
*Director of the United States Patent and Trademark Office*